(12) United States Patent
Agrawal et al.

(10) Patent No.: US 10,406,059 B2
(45) Date of Patent: Sep. 10, 2019

(54) HUMAN MOVEMENT RESEARCH, THERAPEUTIC, AND DIAGNOSTIC DEVICES, METHODS, AND SYSTEMS

(71) Applicant: The Trustees of Columbia University in the City of New York, New York, NY (US)

(72) Inventors: Sunil K. Agrawal, Newark, DE (US); Vineet Vashista, New York, NY (US); Jiyeon Kang, Changwon (KR); Xin Jin, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 134 days.

(21) Appl. No.: 15/304,147

(22) PCT Filed: Apr. 21, 2015

(86) PCT No.: PCT/US2015/026941
§ 371 (c)(1),
(2) Date: Oct. 14, 2016

(87) PCT Pub. No.: WO2015/164421
PCT Pub. Date: Oct. 29, 2015

(65) Prior Publication Data
US 2017/0027803 A1 Feb. 2, 2017

Related U.S. Application Data

(60) Provisional application No. 61/982,256, filed on Apr. 21, 2014, provisional application No. 61/984,555, (Continued)

(51) Int. Cl.
*A61B 5/00* (2006.01)
*A61B 5/11* (2006.01)
(Continued)

(52) U.S. Cl.
CPC .............. *A61H 3/008* (2013.01); *A61B 5/112* (2013.01); *A61B 5/1121* (2013.01);
(Continued)

(58) Field of Classification Search
CPC .... A61H 3/008; A61H 1/0218; A61H 1/0262; A61B 5/112
See application file for complete search history.

(56) References Cited

U.S. PATENT DOCUMENTS 5,020,790 A 6/1991 Beard et al.
5,509,894 A * 4/1996 Mason ................ A61H 1/0255
601/34
(Continued)

FOREIGN PATENT DOCUMENTS

CN 102579229 B 11/2013
EP 1716834 A2 11/2006
(Continued)

OTHER PUBLICATIONS

Extended European Search Report for European Patent Application No. 15783400.3 dated Dec. 14, 2017.
(Continued)

*Primary Examiner* — Nyca T Nguyen
(74) *Attorney, Agent, or Firm* — Potomac Law Group, PLLC; Mark A. Catan

(57) ABSTRACT

Systems for machine-based rehabilitation of movement disorders including gait therapy applications can apply controlled forces to the pelvis and/or other body parts including knee and ankle joints. Cable-driven systems for gait therapy applications can apply controlled forces to, in respective embodiments, the pelvis and the pelvis, knee and ankle joints. In further embodiments, systems for gait therapy can be treadmill-based or walker-based. In embodiments, a controlled downforce is applied to the hip with augmenta-
(Continued)

tion including supportive forces. In further embodiments, the technology is activated through cables that provide support and limb-flexing moments with low inertia and friction resistance. In further embodiments, assistance is configured for gait therapy in children. In still further embodiments, methods of rehabilitation and assist-as-needed (AAN) control of the gait therapy systems facilitate a patient's ability to coordinate movement, control balance, achieve strength, and other beneficial outcomes.

22 Claims, 31 Drawing Sheets

Related U.S. Application Data filed on Apr. 25, 2014, provisional application No. 61/984,559, filed on Apr. 25, 2014, provisional application No. 62/067,361, filed on Oct. 22, 2014, provisional application No. 62/067,722, filed on Oct. 23, 2014.

(51) Int. Cl.
  A61B 5/22 (2006.01)
  A61H 1/02 (2006.01)
  A61H 3/00 (2006.01)

(52) U.S. Cl.
  CPC .......... *A61B 5/1122* (2013.01); *A61B 5/1124* (2013.01); *A61B 5/1128* (2013.01); *A61B 5/224* (2013.01); *A61B 5/6828* (2013.01); *A61B 5/6889* (2013.01); *A61H 3/00* (2013.01); *A61B 2505/09* (2013.01); *A61H 1/0262* (2013.01); *A61H 2201/5097* (2013.01)

(56) References Cited

U.S. PATENT DOCUMENTS

| | | | |
|---|---|---|---|
| 5,961,541 A * | 10/1999 | Ferrati | A61F 5/0102 434/307 R |
| 5,961,544 A * | 10/1999 | Goldman | A43B 3/128 607/111 |
| 6,666,831 B1 * | 12/2003 | Edgerton | A61H 1/0237 600/587 |
| 6,689,075 B2 | 2/2004 | West | |
| 7,125,388 B1 | 10/2006 | Reinkensmeyer et al. | |
| 7,150,722 B1 * | 12/2006 | Tyrrell | A61H 3/008 602/23 |
| 7,462,138 B2 | 12/2008 | Shetty et al. | |
| 7,544,155 B2 | 6/2009 | Agrawal et al. | |
| 7,549,969 B2 * | 6/2009 | van den Bogert | A61F 5/0102 602/16 |
| 7,878,993 B2 | 2/2011 | Agrawal et al. | |
| 8,147,436 B2 | 4/2012 | Agrawal et al. | |
| 8,608,479 B2 | 12/2013 | Liu | |
| 8,613,691 B2 | 12/2013 | Bosecker et al. | |
| 8,684,890 B2 | 4/2014 | Bosecker et al. | |
| 9,532,916 B2 | 1/2017 | Tsui et al. | |
| 9,604,369 B2 | 3/2017 | Angold et al. | |
| 2005/0043661 A1 * | 2/2005 | Nashner | A61B 5/1038 602/26 |
| 2005/0101448 A1 * | 5/2005 | He | A61H 1/0237 482/54 |
| 2005/0239613 A1 | 10/2005 | Colombo et al. | |
| 2007/0275830 A1 | 11/2007 | Lee et al. | |
| 2008/0009771 A1 | 1/2008 | Perry et al. | |
| 2011/0251533 A1 | 10/2011 | Han et al. | |
| 2012/0004581 A1 | 1/2012 | Dinon | |
| 2012/0197168 A1 | 8/2012 | Agrawal et al. | |
| 2013/0158444 A1 | 6/2013 | Herr et al. | |
| 2014/0094345 A1 | 4/2014 | Kim et al. | |
| 2014/0190289 A1 * | 7/2014 | Zhu | B25J 9/104 74/89.22 |
| 2015/0238382 A1 | 8/2015 | Park et al. | |
| 2016/0250094 A1 * | 9/2016 | Amundson | A61H 1/024 623/24 |

FOREIGN PATENT DOCUMENTS

| | | |
|---|---|---|
| KR | 20110041154 A | 4/2011 |
| WO | 2008096210 A1 | 8/2008 |
| WO | 2012024562 A2 | 2/2012 |
| WO | 2013049658 A1 | 4/2013 |
| WO | 2015120186 A1 | 8/2015 |

OTHER PUBLICATIONS

Aoyagi et al., "An assistive robotic device that can synchronize to the pelvic motion during human gait training", Rehabilitation Robotics, 2005. ICORR 2005. 9th International Conference on Jun. 28, 2005, pp. 565-568.
Banala et al., "Robot assisted gait training with active leg exoskeleton (ALEX)", 2nd IEEE RAS & EMBS International Conference on Biomedical Robotics and Biomechatronics, Oct. 19, 2008, pp. 653-658 (Abstract).
Banala et al., "Robot assisted gait training with active leg exoskeleton (ALEX)", IEEE Transactions on Neural Systems and Rehabilitation Engineering, Feb. 1, 2009, vol. 17(1), pp. 2-8 (Abstract).
Bastian, "Understanding sensorimotor adaptation and learning for rehabilitation", Dec. 1, 2008, vol. 21(6), pp. 628-633.
Borggraefe et al., "Improved gait parameters after robotic-assisted locomotor treadmill therapy in a 6-year-old child with cerebral palsy", Movement Disorders, Jan. 30, 2008, vol. 23(2), pp. 280-283.
International Search Report and Written Opinion for International Application No. PCT/US2015/026941 dated Sep. 23, 2015.
Kleim et al., "Principles of Experience-Dependent Neural Plasticity: Implications for Rehabilitation After Brain Damage", J. Speech Lang.Hear. Res., Feb. 1, 2008, vol. 51, pp. S225-S239.
Lu et al., "Development and Learning Control of a Human Limb With a Rehabilitation Exoskeleton", IEEE transactions on industrial electronics, Jul. 1, 2014, vol. 61(7), pp. 3776-3785 (Abstract).
Martin et al., "Throwing while looking through prisms. II. Specificity and storage of multiple gaze-throw calibrations." Aug. 1, 1996, vol. 119(4), pp. 1199-1211.
Merodio et al., "Exploiting joint synergy for actuation in a lower-limb active orthosis", Industrial Robot: An International Journal, Apr. 26, 2013, vol. 40(3), pp. 224-228 (Abstract).
Olney et al., "Mechanical energy patterns in gait of cerebral palsied children with hemiplegia", Phys Ther., Sep. 1, 1987, vol. 67(9), pp. 1348-1354.
Peshkin et al., "KineAssist: A robotic overground gait and balance training device", InRehabilitation Robotics, ICORR 2005, 9th International Conference on Jun. 28, 2005, pp. 241-246.
Sanes et al., "Plasticity and primary motor cortex", Annual Review of Neuroscience, Mar. 1, 2000, vol. 23(1), pp. 393-415.
Savin et al, "Poststroke Hemiparesis Impairs the Rate but not Magnitude of Adaptation of Spatial and Temporal Locomotor Features", Neurorehabil Neural Repair, Jan. 1, 2013, vol. 27(1), pp. 24-34.
Surdilovic et al., "String-Man: a new wire robot for gait rehabilitation", Robotics and Automation, 2004. Proceedings. ICRA '04. 2004 IEEE International Conference on Apr. 26, 2004, vol. 2, pp. 2031-2036 (Abstract).
Surdilovic et al., "String-Man: Wire-robot technology for safe, flexible and human-friendly gait rehabilitation", InRehabilitation Robotics, 2007, ICORR 2007, IEEE 10th International Conference on Jun. 13, 2007, pp. 446-453.
Vallery et al., "Multidirectional transparent support for overground gait training", InRehabilitation Robotics (ICORR), 2013 IEEE International Conference on Jun. 24, 2013, pp. 1-7.
Vashista et al., "Asymmetric adaptation in human walking using the Tethered Pelvic Assist Device (TPAD)", InRehabilitation Robotics (ICORR), 2013 IEEE International Conference on Jun. 24, 2013, pp. 1-5.

(56) References Cited

OTHER PUBLICATIONS

Vashista et al., "Experimental studies on the human gait using a tethered pelvic assist device (T-PAD)", InRehabilitation Robotics (ICORR), 2011 IEEE International Conference, Jun. 29, 2011, pp. 1-6.

Vashista et al., "Force adaptation in human walking with symmetrically applied downward forces on the pelvis", 34th International Conference of the IEEE, Aug. 28, 2012, pp. 3312-3315.

Veg et al., "Walkaround: Mobile Balance Support for Therapy of Walking", Neural Systems and Rehabilitation Engineering, IEEE Transactions, Jun. 10, 2008, vol. 16(3), pp. 264-269 (Abstract).

Veneman et al., "Design and Evaluation of the LOPES Exoskeleton Robot for Interactive Gait Rehabilitation", Neural Systems and Rehabilitation Engineering, IEEE Transactions, Sep. 1, 2007, vol. 15(3), pp. 379-386.

Zanotto et al., "ALEX III: A novel robotic platform with 12 DOFs for human gait training", InRobotics and Automation (ICRA), 2013 IEEE International Conference on May 6, 2013.

Adamovich et al., "Sensorimotor training in virtual reality: A review," NeuroRehabilitation, vol. 25, No. 1, pp. 29-44, 2009.

Harbourne et al., "Nonlinear analysis of the development of sitting postural control," Dev. Psychobiol., vol. 42, No. 4, pp. 368-377, 2003.

International Preliminary Report on Patentability for International Application No. PCT/US2015/026941 dated Nov. 3, 2016.

Lee et al., "A virtual reality system for the assessment and rehabilitation of the activities of daily living.," Cyberpsychology Behav., vol. 6, No. 4, pp. 383-388, 2003.

Maciejasz et al., "A survey on robotic devices for upper limb rehabilitation", Journal of NeuroEnigneering and Rehabilitation, vol. 11, Issue 3, Jan. 9, 2014.

Mao, "Transition from mechanical arm to human arm with CAREX: A cable driven ARm EXoskeleton (CAREX) for neural rehabilitation," in Proc. IEEE Int. Conf. Robot. Autom., 2012, pp. 2457-2462.

Massion, "Postural control systems in developmental perspective," Neurosci. Biobehav. Rev., vol. 22, No. 4, pp. 465-472, 1998.

Anand K. Ojha, "An Application of Virtual Reality in Rehabilitation," IEEE Southeastcon, pp. 4-6, 1994.

Rose et al., "Virtual reality: an assistive technology in neurological rehabilitation.," Current opinion in neurology, vol. 9, No. 6. pp. 461-467, 1996.

Stuart, "Integration of posture and movement: Contributions of Sherrington, Hess, and Bernstein," Hum. Movement Sci., vol. 24, Nos. 5-6, pp. 621-643, 2005.

\* cited by examiner

Fig. 1D          Fig. 1E

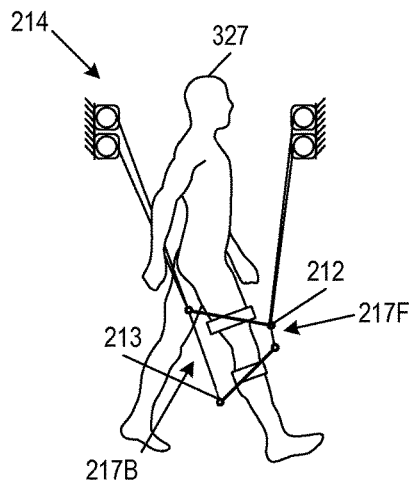
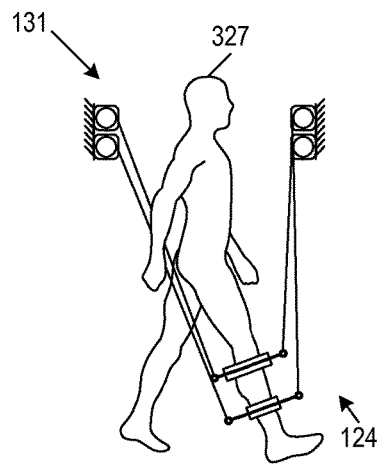
Fig. 8L     Fig. 8M
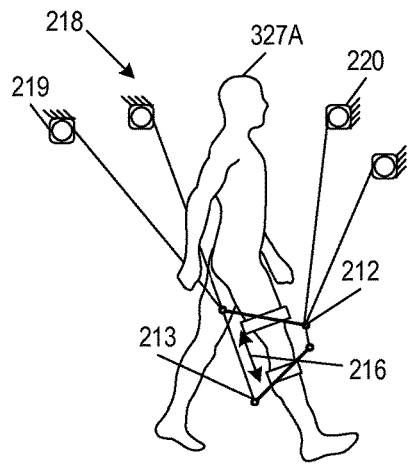
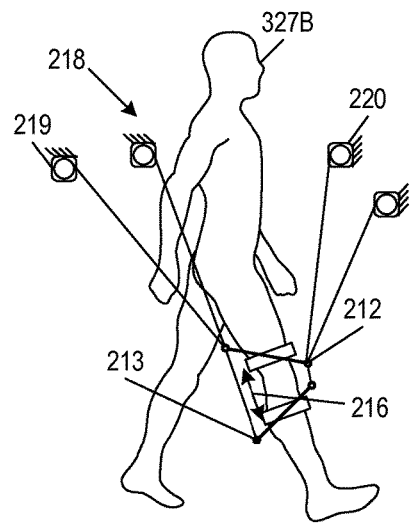
Fig. 8N     Fig. 8P

(a) Non visual feedback group (b) Visual feedback group (a) A cable motion test (b) Wire pull compensation (a) Pelvic motion over the gait cycle (b) Pelvic motion asymmetric measure

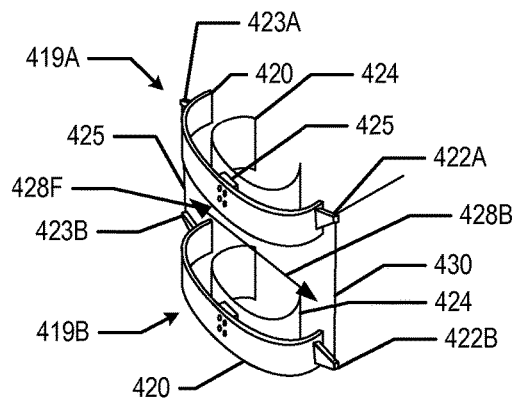
Fig. 25A
Fig. 24
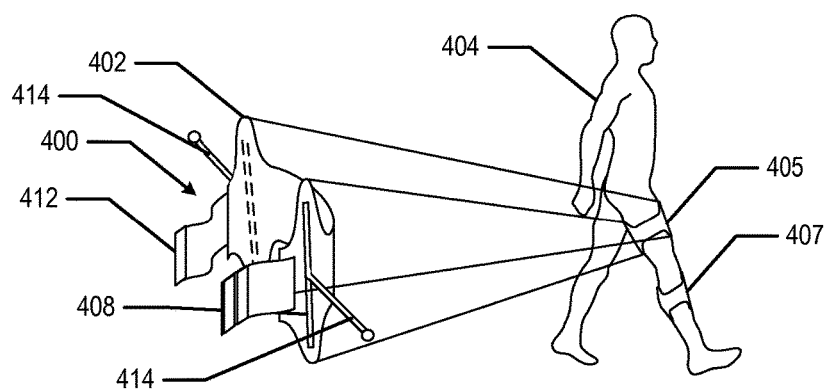
Fig. 25B

HUMAN MOVEMENT RESEARCH, THERAPEUTIC, AND DIAGNOSTIC DEVICES, METHODS, AND SYSTEMS

CROSS-REFERENCE TO RELATED APPLICATIONS

The present application is a U.S. national stage filing under 35 U.S.C. § 371 of International Application No. PCT/US2015/026941 filed Apr. 21, 2015, the content of which is hereby incorporated by reference in its entirety, which claims priority to U.S. Provisional Application Nos. 61/982,256, entitled "Pelvis Manipulation Devices Methods and Systems" filed Apr. 21, 2014; 62/067,361, entitled "Pelvis Manipulation Devices Methods and Systems" filed Oct. 22, 2014; 61/984,559, entitled "Leg Manipulation Devices Methods and Systems" filed Apr. 25, 2014; 62/067,722, entitled "Leg Manipulation Devices Methods and Systems" filed Oct. 23, 2014; and 61/984,555, entitled "Child Pelvis Assist Devices Methods and Systems" filed Apr. 25, 2014, each of which is hereby incorporated herein by reference in its entirety.

STATEMENT REGARDING FEDERALLY SPONSORED RESEARCH OR DEVELOPMENT

This invention was made with government support under 1339666 awarded by the National Science Foundation and DH038582 awarded by the National Institutes of Health. The government has certain rights in the invention.

BACKGROUND

Various populations have movement disorders. With an aging population comes the increased need for improved rehabilitation technologies for disabilities caused by brain and spinal cord injury, stroke and other neurological and orthopedic conditions. For stroke victims, intense physiotherapy is often required to regain and improve ambulatory and brain functions. Neurological conditions affecting walking and balance can also exist at any age, for example children with cerebral palsy suffer from a deficiency in their ability to control the movement of their bodies' center of mass. Patients suffering from brain and spinal cord injury, stroke or other neurological and orthopedic conditions, may benefit from mobility assistance and therapeutic devices. Current attempts at gait therapy improve function, but are labor intensive and limited by the demands and availability of physical therapists. The success of treatment is limited by the physical demands and availability of physical therapists. Robotic devices have been proposed for gait rehabilitation and other forms of movement training and rehabilitation and these can potentially reduce the physical burden on healthcare providers and the financial burden on patients.

The development of innovative movement training approaches for persons with movement disorders is important. Various patient groups demonstrate limited ability to bear body weight on their affected limbs during walking, e.g., stroke survivors with weakness on one side and kids with cerebral palsy. This results in shorter stance time on the affected side and asymmetric distribution of the ground reaction forces, affecting the overall gait symmetry. Such asymmetric gait patterns may be associated with higher energy costs and increased risks of fall, which, in turn, limits independence and quality of life of these subjects. Thus, symmetric weight bearing during walking may be important in gait rehabilitation.

Robotic rehabilitation devices can be used in physical therapy to offer more uniform training over an extended period of time and across different groups of patients. They can provide quantitative measures of the subject's performance and the required labor of physical therapists can be greatly reduced. Although various leg exoskeletons have been developed for gait training of neurologically impaired patients, many leg exoskeletons use links and mechanical joints placed in parallel with human limbs and joints, which adds extra weight and inertia to the human limbs and thereby changes the natural walking dynamics of the wearer. Furthermore, accurate alignment between the joints of the exoskeleton and the wearer is required, which may be difficult or impossible to accomplish due to the complex geometry of the human body.

SUMMARY

The disclosed subject matter includes methods, devices, and systems for machine-based rehabilitation of movement disorders including gait therapy applications that can simultaneously apply controlled forces to the pelvis and/or other body parts including knee and ankle joints. The disclosed subject matter includes cable driven systems for gait therapy applications that can simultaneously apply controlled forces to, in respective embodiments, the pelvis and the pelvis, knee and ankle joints. In further embodiments, methods, devices and systems for gait therapy are treadmill-based and walker-based, respectively. In embodiments, controlled downforce is applied to the hip with augmentation including supportive forces. In further embodiments, the technology is activated through cables that provide support and limb-flexing moments with low inertia and friction resistance. In further embodiments, assistance is configured for gait therapy in children. The disclosed subject matter also includes methods of rehabilitation and assist-as-needed (AAN) control of the gait therapy systems to facilitate patient's ability to coordinate movement, control balance, achieve strength, and other beneficial outcomes.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 1D and 1E show 3D views of embodiments of cable-driven leg manipulation devices according to one or more embodiments of the disclosed subject matter.

FIG. 8L schematically illustrates a cable driven leg manipulation device showing features including fixed winches, thigh and shank adapters with extensions that provide for clearance, features that may be used in any of the embodiments and devices that can be replicated for both legs, according to embodiments of the disclosed subject matter.

FIG. 8M schematically illustrates a cable driven leg manipulation device showing features including fixed winches, two shank adapters supporting active plantar/dorsiflexion motion and a thigh adapter for lateral displacement forces, features that may be used in any of the embodiments and devices that can be replicated for both legs, according to embodiments of the disclosed subject matter.

FIGS. 8N and 8P shows a cable driven leg manipulation device with separation between the thigh and shank adapters optimized for a fixed separation between them to accommodate subjects of different heights or proportions, features that may be used in any of the embodiments and devices that can be replicated for both legs, according to embodiments of the disclosed subject matter.

FIG. 24 is a processed photograph of a tested embodiment of a CPWD showing an adult test subject in position with respect to it, according to embodiments of the disclosed subject matter.

FIG. 25A shows limb adapter with longitudinal extensions for generating torque on the limb according to embodiments of the disclosed subject matter.

FIG. 25B shows an optional cuff with longitudinal extensions for reducing the pressure for a given torque applied to the limb, according to embodiments of the disclosed subject matter.

DETAILED DESCRIPTION

Figure 1A:
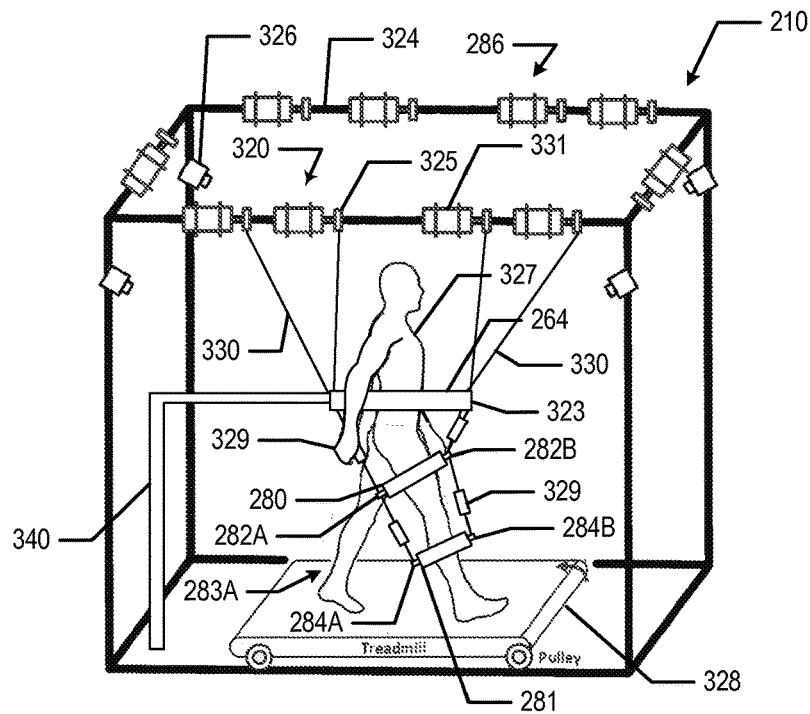
FIGS. 1A and 1B illustrate a subject walking with a cable-driven leg manipulation device, according to respective embodiments of the disclosed subject matter.

The disclosed subject matter includes cable-driven robotic rehabilitation systems (CDRR). Cable-driven systems can have many advantages including lower capital cost, lower weight, tolerance to anatomical differences among patients, tolerance to misalignment of apparatus with patient bodies, and other benefits. In embodiments, such systems may allow rehabilitation of weight-bearing competence of patients, correction of walking impairments and other rehabilitation applications. For example, embodiments may operate as an exoskeleton to apply forces to assist, load, or guide the movements of a patient walking on a treadmill by applying forces to the legs and/or body. Such embodiments are described herein in connection with a particular embodiment that was subject to testing. The embodiment is called cable-driven active leg exoskeleton (C-ALEX). Cables apply forces to adapters for one or more of the pelvis, thighs, shank, and foot. In further embodiments, a CDRR applies asymmetric external forces to the pelvis during treadmill-walking or free walking in which perturbations are applied to the pelvis to challenge, and ultimately enhance, a patient's resistance to falls. These latter two are described herein as embodiments of CDRR called active tethered pelvic assist device (A-TPAD). In embodiments, A-TPAD applies external forces on a pelvis adapter, worn by a human, via actuated cables.

CDRR embodiments manipulate the lower extremities and optionally the pelvis and are embodied in devices called cable-driven active leg exoskeleton (C-ALEX) which are presently described in applications for gait training for which experimental studies have confirmed their capabilities. The C-ALEX embodiments used in testing employed three adapters (body part adapters, collectively), for connection to the waist, the thigh and the shank of the wearer. The system can further be used with other body part adapters in combination, or in alternative embodiments, including hip adapters for manipulating the pelvis and adapters for other limbs by extending the principles discussed herein. One or both legs can be manipulated with suitable addition of body part adapters. Actuation is performed with cables routed through a frame and the body adapters. Rigid links and joints such as used within the exoskeletons can be avoided reducing concerns about precise alignment of the exoskeleton joints and human joints. The C-ALEX exoskeleton may be controlled in force mode using an assist-as-needed (AAN) control paradigm. An experiment with 6 subjects was carried out which shows that C-ALEX can effectively assist its wearer to alter his or her gait.

In A-TPAD embodiments, the pelvis adapter may include a belt worn about the hips, for example, or a harness that wraps around the upper thighs and waist. In contrast to body weight support systems, the A-TPAD is configured to apply controlled external wrenches on the human pelvis in selected directions in coordination with the gait cycle for predefined or calculated durations, including downward forces along the legs. During walking with the A-TPAD, the pelvic motion may be monitored in real-time using a motion capture system. An online optimization scheme is used to compute the selected cable tension values to be applied. In experiments, the A-TPAD has been demonstrated to be capable of control of the applied wrench during human walking.

A-TPAD can be used scientifically to treat walking abnormalities as well as study human adaptation in gait due to externally applied forces and moments on the pelvis. In clinical settings, such uses may correspond to developing custom treatment regimens for individuals with unique functional limitations. A-TPAD may also be used as a basis for a flexible or single-purpose system for rehabilitation. Studies using A-TPAD can help provide new gait rehabilitation paradigms that can potentially be used to correct gait deficits in human walking for individuals or for classes of patients. A-TPAD is configured selectively to apply external wrench on the human pelvis both during the swing phase and stance phase. A-TPAD embodiments may also be configured selectively to apply external forces on the legs only during the swing phase. Embodiments may benefit from reduced inertia of the equipment, lower levels of constraint on the subject's motion as with hinged joints, and other features apparent from the description.

In experiments, using A-TPAD, vertical downward force was applied on the pelvis of a healthy subject over a complete gait cycle, equivalent to 10% of subject's body weight. Results showed the subjects adapted in their gait patterns as a result of the externally applied forces and also show beneficial aftereffects once the forces are removed. In addition, subjects walked with higher forces transmitted through their legs both during training and once the external forces are removed during post-training. This has important consequences in terms of stance timing, gait symmetry, weight bearing and bone health of the legs.

Disclosed embodiments of therapeutic methods include the use of A-TPAD for treatment of stroke survivors, spinal cord injury patients, children with cerebral palsy, balance abnormalities, functional gait asymmetry, bone development abnormalities, amputees, brain injury survivors and other neurological or muscular impairments to mobility. In embodiments, the A-TPAD is used for such impairments in which patients exhibit poor balance during walking, gait asymmetry and reduced ability to bear weight on their legs. Treadmill walking with partial weight support is a widely adopted gait rehabilitation strategy but has not been demonstrated to be superior to home-based physical therapy. Home training with therapists requires demanding manual labor while working with the patients to move their limbs during training. A-TPAD provides a solution to these and other problems relating to gait rehabilitation strategies.

Pediatric walkers provide rolling support to keep children from falling and help them develop walking competence. A child can hold on to the handle of a walker or wear a harness to get support. These walkers can compensate for partial body weight of the child. In further embodiments of CDRR, cable drive pediatric walkers (CDPW) can actively support the pelvis to assist in gait balance. Active support by the DCPW includes the application of predefined forces/torques on the child's body in response to sensed motion of a child in the CDPW. Sensors may detect child's body position and interactive forces may be computed to facilitate balance. Walkers may include passive wheels or driven wheels according to embodiments.

Embodiments with C-ALEX Features

In one or more embodiments of the disclosed subject matter, a leg manipulation device is used for human gait training. For example, the leg manipulation device may be identified as cable-driven active leg exoskeleton (C-ALEX), embodiments of which are illustrated in FIG. 1A and indicated at 283A. An exoskeleton has three adapters: a hip adapter 264, a thigh adapter 280, and a shank adapter 281. The hip adapter 264 is positioned to engage the hips and waist, in the present embodiment, and fixedly supported by a support 340. The hip adapter 264 or its connection to the support 322 may provide compliance with sufficient compliance to permit limited motion attending walking-in-place. Additional or fewer adapters and/or different locations for the adapters are also possible as should be clear from the description herein. One or more cables are routed through respective adapters. For example, hip adapter 264 has spaced apart guides to allow the passing of respective cables connected to the thigh adapter 280 and to the shank adapter 281. Each cable has a respective tension sensor 329. Traction is applied to the cables 330 by respective winches 320, each including a motor 331 and pulley 325. The winches 320 are mounted to a frame 324. The tension sensors 329 generate signals to permit the motion of the attached limbs of the subject 327 to be detected and thereby to apply assist-as-needed (AAN) control of the motion of the subject 327 limbs. Although an exoskeleton is shown connected to a single leg of the subject 327, the elements described may be duplicated to provide a bilateral system for supporting both legs of a subject 327.

The configuration of the C-ALEX embodiment uses cable tension to apply torques to the to the thigh adapter 280 and to the shank adapter 281 through tension generated by the winches 320. The separate cable sets, each set being a pair for each of the thigh adapter 280 and shank adapter 281, are able to apply a force to facilitate or inhibit hip flexion/extension and knee flexion/extension. The hip adapter 264 has a frame portion that keeps the cables separated from the hip joints of the subject 327 throughout the range of motion of the leg of the subject 327. The hip adapter 264 may be of a rigid material that curves around the subject's waste with a pivotally-mounted pad which may also have a belt to wrap around the hips or waist of the subject 327. The thigh adapter 280 keeps the cables separated from the knee joint of the subject 327 in the same manner. The separation distance may be selected to provide balance between the selected torque and the lifting force generated by the cable 330. The use of cables in this manner avoids the need for rigid links or joints that need to be aligned with the joints of the subject 327 as in other types of exoskeleton.

Respective ones of cables 330 connect to the shank adapter 281 at terminations 284A and 284B which are in turn attached to extensions integral to the shank adapter thereby preventing the cables 330 from interferingly engaging the leg of the subject 327. The connections at terminations 284A and 284B are fixed connections at which the cables respective ones of the 330 terminate. These same cables 330 that terminate at the terminations 284A and 284B pass through guides/terminations 282A and 282B which allow the same cables 330 to slide therethrough so as to apply moments to the shank adapter 281. The hip adapter 264 has guides 323 that permit cables 330 that terminate at the thigh adapter 280 and shank adapter 281 to pass through them. The hip adapter 264 guides 323 are on extensions integral to the hip adapter 264 that help to keep the cables 330 from interfering with the movement of the arms and legs of the subject 327.

The subject 327 may walk on a treadmill 328 that is accommodated within the frame 324. In alternative embodiments, instead of a treadmill, the frame is fitted with wheels to permit the subject 327 to walk around on a fixed floor. The wheels may be passive and may include caster wheels. Alternatively, the wheels may be motorized and controlled according to forces generated by the user through the hip adapter 264

Figure 1B:
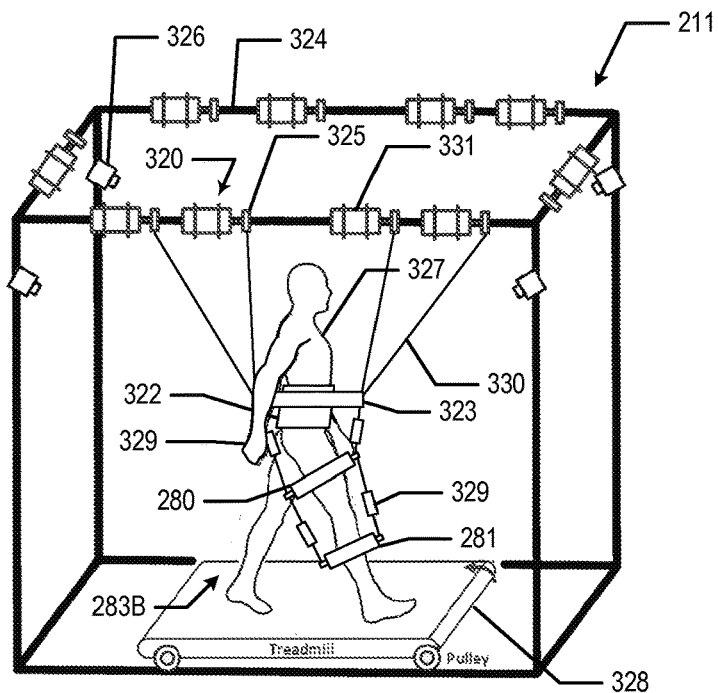

FIG. 1B shows a variation on the configuration of FIG. 1A in which the hip adapter 323 rather than being fixed as in the embodiment of FIG. 1A, is supported by the subject 327. A stiff padded belt 321 supports the hip adapter 323 which performs the same function as in the embodiment of FIG. 1A.

In the embodiments of FIGS. 1A and 1B, exoskeletons 283A and 283B are shown with a configuration for a single leg, but it will be understood that in any embodiment, there may be an exoskeleton 321A, 321B for each leg with the respective winch 320 mounted to the frame 324 as shown. In any of the embodiments, a motion capture system may be provided, for example a multi-camera 326 type of system. Motion capture balls may be built into or attached to the various adapters to provide feedback to the control system to be described. In addition the motion capture may support visual feedback to the subject 327. Image recognition processes may interpret a video feedback from the motion capture to identify the position and configuration of the subject in order to determine if the subject is in misconfiguration, such as the subject falling or misusing the system. In response to detection of a misconfiguration, the controller may generate an alarm signal and/or go into a failsafe configuration, such as one that permits all the cables to be drawn at-will by the subject 327 or one in which all the cables are halted. The treadmill may be halted by the controller as part of the failsafe configuration.

The exoskeleton can be controlled in force mode using an "assist-as-needed" (AAN) control paradigm to help the ankle center (and/or knee center) move along a prescribed path. Thus, in one or more embodiments, the cable-driven device may have a simpler structure, add minimal (or at least reduced) inertia to the human limbs, and avoid (or at least reduce) the requirement for precise joint alignment. Details of control aspects are described below.

The winches 320 may be placed on the frame 324 in any suitable positions to ensure that the cables 330 do not interfere with natural motions of the arms, legs, and body during walking. For example, they may be aligned with the sagittal plane so that the cables 330 do not cross a volume covering the range of positions occupied by a free swinging arm of the subject 327. The shapes of the adapters may be such that they guide and position the cables for the same result. For example, they may curve around the body of the subject toward the sagittal plane. See FIG. 2 for an impression of such curvature in the integral extensions that position the cables 330. Unlike the hip adapter shown in this figure, a hip adapter may conform close to the body of the person so that the arms can swing freely at the sides. Alternatively it may be positioned remote from the subject but extend beyond the range of the arm swing before turning toward the sagittal plane so that an empty volume is defined that permits the arms to swing, surrounded by the hip adapter. In such an embodiment, a hip/waist belt may attach to the ends closest to the sagittal plane and otherwise conform closely to the body. Note in various depictions, tension sensors are referred to as load cells as in FIG. 2.

Figure 2:
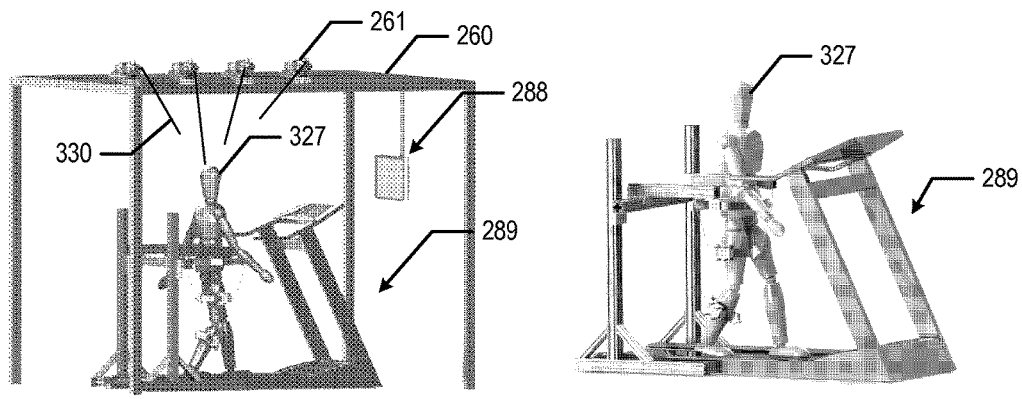
FIG. 2 shows a computer-aided drawing (CAD) model (left) and photo (right) of a cable-driven leg manipulation device on the leg of a subject, according to one or more embodiments of the disclosed subject matter.
Figure 2:
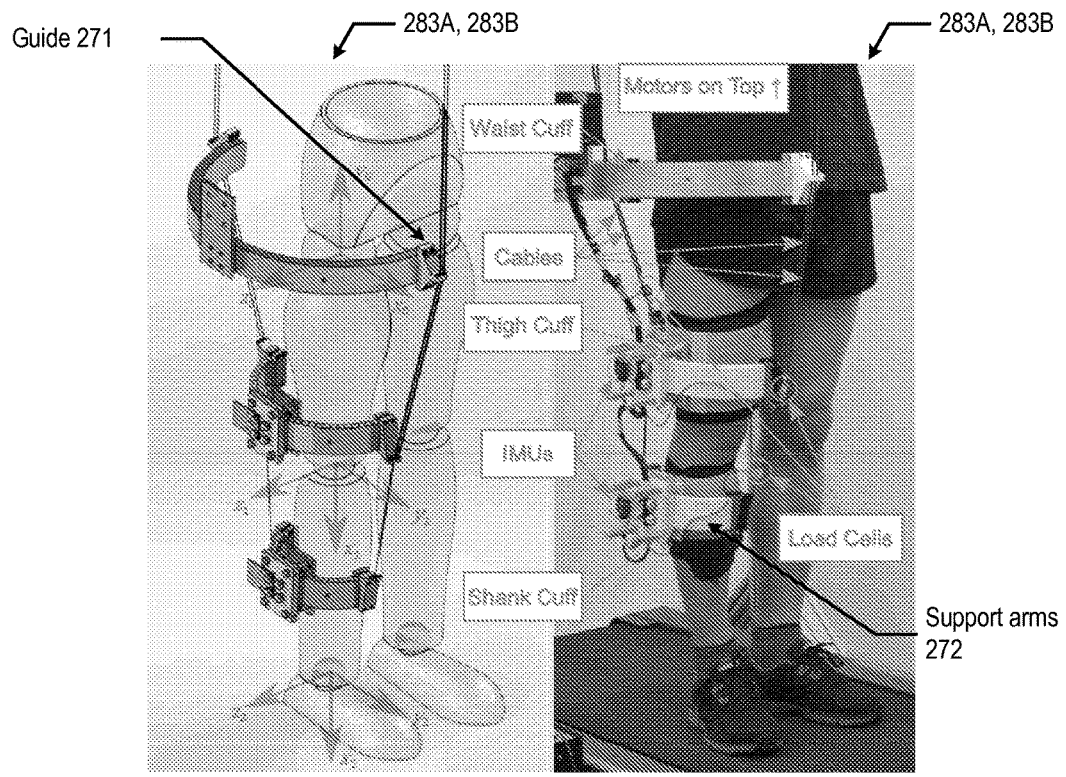

FIG. 2 shows a three-dimensional rendering of the exoskeleton 283A, 283B next to a photo subject wearing a C-ALEX exoskeleton, according to one or more embodiments of the disclosed subject matter. In FIG. 2, the adapters are identified as "cuffs." Guides 271 are shown. These can include nylon grommets that the cable slides through or other suitable sliding guide configurations. Embodiments may include a guide with pulley wheels to minimize friction. The tension sensors 329 are identified as "load cells." It will be observed that two cables pass through the hip adapter (waist cuff), one of which attaches to the thigh adapter (thigh cuff) and of the other passing through the thigh adapter (thigh cuff) to attach to the shank adapter (shank cuff).

As described with reference to FIG. 1A, the hip adapter (waist cuff) can be fixed to a height-adjustable external support frame to accommodate subjects of different height. Alternatively, the hip adapter can be attached to or worn by the subject and the fixed support frame eliminated as discussed in reference to FIG. 1B. The thigh and the shank adapters are tightly connected to the wearer's thigh and shank, respectively. To create a secure connection between the thigh and shank adapters and the leg, a layer of medical strap can be placed on to the subject's leg. An orthotic with Velcro liners can then be strapped on top of the medical straps. The adapters can be attached at the lateral side of the orthotics. The lateral distance between the adapter and the leg can be adjusted. Other secure attachment mechanisms between each adapter and the respective portion of the leg are also possible according to one or more contemplated embodiments. In embodiments, custom made orthoses for each subject can be made and configured so that they are attachable/detachable with locking connectors to a frame for each adapter. Such a configuration may permit the subject to set up outside the exoskeleton reducing the down time of the system between patients.

To reduce the weight of the exoskeleton on subject's leg, the thigh and shank adapters can be constructed, at least in part, of acrylonitrile butadiene styrene (ABS) plastic with a honeycomb-like interior. Such a structure is susceptible to fabrication using 3D printing. For example, the overall weight of the thigh and shank adapters can be 0.60 kg and 0.54 kg, respectively. Other materials for the adapters are also possible according to one or more contemplated embodiments.

FIGS. 1D and 1E show perspective views of the apparatus of the embodiment FIG. 1A. A frame 260 supports winches 261 which draw cables 330 to actuate an exoskeleton attached to subject 327. A computer-driven display 288 may be supported by the frame to provide visual feedback to the subject 327 to improve training speed. A treadmill 289 may be interchangeably associated with the frame 260 to provide the rehabilitation system. FIG. 1E shows the setup of FIG. 1D without the frame and associated components.

Cables of any of the embodiments may be of pre-stretched nylon-coated steel wires but other materials and composites may be used. In embodiments, four cables can be used to actuate the exoskeleton. Some or all of the four cables can be routed through the hip adapter. Two of the cables can be attached to the thigh adapter, while the remaining two cables can be routed through the thigh adapter and attached to the shank adapter. These four cables can control two degrees-of-freedom of the wearer's leg: (1) the hip flexion/extension and (2) the knee flexion/extension. The Denavit-Hartenberg (DH) parameters of the exoskeleton are shown in Table I below.

TABLE 1

DH Parameters

| Link | a | d | α | θ |
|------|------|---|----|---------|
| 1 | $L_{th}$ | 0 | 0° | $q_1 - 90°$ |
| 2 | $L_{sh}$ | 0 | 0° | $-q_2$ |

In the DH parameters, $q_1$ is the hip flexion angle, $q_2$ is the knee flexion angle, $L_{th}$ stands for thigh length, and $L_{sh}$ stands for shank length. In embodiments, the kinematics of C-ALEX can be characterized through the DH parameters and homogeneous transformations. A cable routing point (sliding guide) on the adapter can have a Teflon liner to reduce the friction between the cable and the adapter. The cable routing points can be designed to be able to slide along the adapter. Additional cable routing points can be made to accommodate extra cables to increase the controlled degrees-of-freedom. For example, additional cables can be provided to generate assistive hip abduction/adduction torques.

Winches of the embodiments may cables in the exoskeleton can be driven by any suitable servo motor or other similar device, including a stepper motor. Although the winches are described as servo motors with pulleys, they can be replaced with linear drives or other types of mechanisms to provide a similar controlled tension, acceleration, and positioning as servo motors. To measure the tension in the cables, a load cell can be connected to the middle or end of each cable. The tension sensors can be of any suitable type. An example includes Futek LSB200 load cells with CSG110 signal conditioners. An inertia measurement unit (IMU), such as a VectorNav VN-100 IMU, can be mounted on the thigh adapter and shank adapter to measure the hip and knee angle of the wearer during walking. Additional measurements or data can be made by existing or additional sensors, for example, measuring cable lengths to provide or assist in providing information on adapter location. Instead of tension, or in addition, a moment on the adapter extension may be measured.

A controller, such as a National Instrument PXIe-8135 controller, can be used for real-time control (e.g., of the cable drive device to apply selected tensions to the cables) and data acquisition (e.g., of sensor data from the load cells or other sensors) of the exoskeleton. For example, the controlling software can be developed in LabVIEW.

The dynamic equations of motion of the C-ALEX can be derived through the Lagrangian method. The generalized coordinates $q_1$ and $q_2$ represent the angle of hip flexion and knee flexion, respectively. The equations of motion take the following form:

$$D(q)\ddot{q}+C(q,\dot{q})\dot{q}+G(q)=U, \quad (1)$$

where $q=[q_1,q_2]^T$ is the vector of generalized coordinates; D(q) is the 2×2 inertia matrix; C(q,$\dot{q}$) is the vector of Coriolis and centripetal terms; G(q) is the vector of gravity terms; U is the vector of generalized force corresponding to the generalized coordinate q. The left hand side of Eqn. (1) closely resembles the dynamical equation of a double pendulum. The geometric and inertial parameters in Eqn. (1) can be obtained through the CAD model of C-ALEX and measurements from the wearer's leg. The generalized force U on the right-hand side of Eqn. (1) is the torque at the hip and knee joint generated by the cables. The relation between the joint torque U and cable tension T can be obtained by the virtual work principle.

Figure 3:
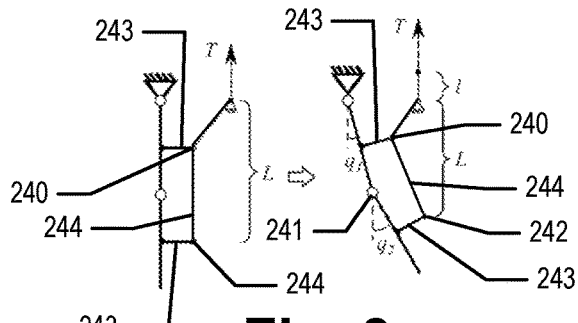
FIG. 3 is a schematic diagram of a two-link model of a system actuated by a single cable.

FIG. 3 shows the schematic of a two link system actuated by a single cable 244, which forms an element of the cable actuated system of certain disclosed embodiments. The system of FIG. 3 is a kinematic representation of an elementary component of the exoskeletons of the various embodiments as should be evident from the respective descriptions. Joint 240 is a sliding joint allowing the cable to pass through it. Circles such as indicated at 241 represent revolute joints. The following is an analysis of the kinematic system of FIG. 3. A force T is applied on the cable 244 which results in the configuration of the 2-link system to change due to forces applied to the sliding joint 240 and the cable fixation point 242 on respective levers 243. Using the principle of virtual work, the input-output mapping between a cable applied tension and the vector U in Eqn. (1) can be generated. The tension T will result in the cable being pulled out by $\delta l$. From the principle of virtual work:

$$\delta W = T \cdot \delta l = U \cdot \delta q, \quad (2)$$

where U and q are generalized forces and coordinates (i.e., joint torques and joint angles). Since $$\delta l = \frac{\partial l}{\partial q}\delta q, \quad (3)$$

the change of pulled out cable $\delta l$ can be related to the change of cable that remains in the system $\delta L$ by $l+L=$constant, which gives:

$$\frac{\partial L}{\partial q}+\frac{\partial l}{\partial q}=0. \quad (4)$$

Substituting Eqns. (3) and (4) into Eqn. (2), the relationship between the joint torque U and the cable tension T can be formulated as:

$$U = -\left(\frac{\partial L}{\partial q}\right)^T T = J_T(q)^T T. \quad (5)$$

With four cables within C-ALEX, the Jacobian matrix J(q) can be written as:

$$J_T(q) = -\frac{\partial(L_1, L_2, L_3, L_4)}{\partial(q_1, q_2)}, \quad (6)$$

where $L_i$ is the length of cable i measured from the routing point on the hip adapter to the final attachment point of the cable on the thigh or shank adapters. Eqn. (5) can provide the foundation to solve for the required cable tensions when specific torques are selected at the joints.

To generate a set of torques at the joints, the required tensions to be applied by the motors on the cables can be calculated. A cable tension can be found by solving the set of linear equations:

$$J_T(q)^T T = U \quad (7)$$

where J(q) is the Jacobian matrix in Eqn. 6, U is the vector of torques selected for the exoskeleton to generate at the joints, and T is the vector of cable tensions needed to be solved for. Eqn. (7) is underdetermined since the number of cables is larger than the degrees-of-freedom of the system.

The possible tensions in the cables can be limited. Since the cables can only pull but not push, it is impossible for the tensions in the cables to be negative. In the actual system, due to the existence of friction along the cables, the minimum tension in a cable can be set above a positive value to keep all of the cables taut. Also, because the motors connected to the cables can only produce a limited amount of torque, there may be a maximum limit on cable tensions as well. Therefore, T can satisfy:

$$T \in [T_{min}, T_{max}]. \quad (8)$$

For example, the cable tension range can be 7N to 70N, inclusive.

Using Eqns. (7) and (8) as constraints, an optimization problem may be formulated to find a proper set of cable tensions to generate selected torques. For example, a quadratic objective function ($f(T) = T^T T$) can be used for the optimization problem, which minimizes the norm of cable tension vector. The advantage of using quadratic programming over linear programming is that the solution to T will change more continuously when the Jacobian matrix $J_T(q)$ in the equality constraint of Eqn. (7) changes, which will help to avoid abrupt changes in cable tensions when the leg moves from one configuration to another.

Overall, the cable tension planning problem can be formulated as a quadratic programming problem:

$$\min f(T) = T^T T$$

$$\text{s.t. } J_T(q)^T \cdot T = U \text{ and } T \in [T_{min}, T_{max}].$$

The above can be solved using a quadratic programming solver, for example, the quadratic programming solver provided by LabVIEW, which uses the active set method and can solve the above problem in real time (e.g., the controller can solve the above problem at a frequency of 100 Hz without any delay).

Embodiments of the disclosed exoskeleton device can be used for rehabilitation. Thus, the controller of the exoskeleton device can be configured for an "assist-as-needed" strategy, e.g., to assist the ankle point of the wearer of the exoskeleton to move on a prescribed target path. The controller can create a tunnel-like force field around the target path. If the end effector (e.g., ankle point) deviates from the target path, the controller acts as a spring and pulls the end effector back to the target path.

Figure 4A:
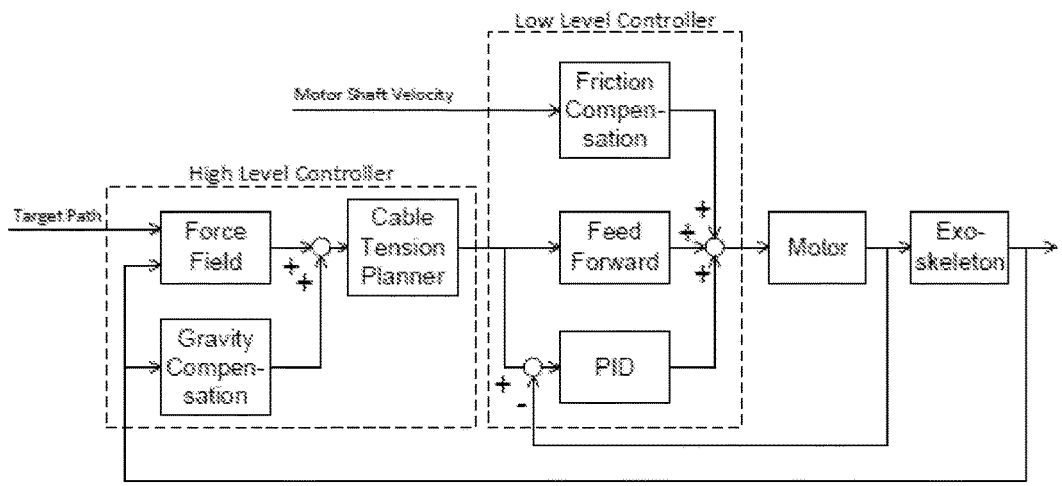
FIG. 4A is a schematic diagram of a controller for a cable-driven leg manipulation device, according to one or more embodiments of the disclosed subject matter.
Figure 4B:
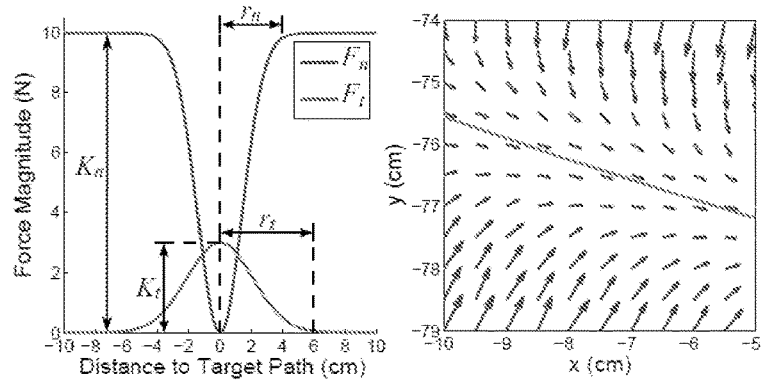
FIG. 4B are graphs illustrating the magnitude of the force field as function of the normal distance from the target path (left) and a portion of the force field around a target path (right) for a cable-driven leg manipulation device, according to one or more embodiments of the disclosed subject matter.

For example, a two level system can be used for the controller of the exoskeleton device, as illustrated schematically in FIG. 4. A high level force-field controller can use the position feedback of the exoskeleton to dictate the necessary cable tensions to create the force field. A low level cable tension controller can control the motors to produce the selected cable tensions using feedback from the load cells on the cables.

The high level force-field controller can generate a force F at the ankle point that has two components:

$$F = F_n + F_t \quad (9)$$

Figure 5:
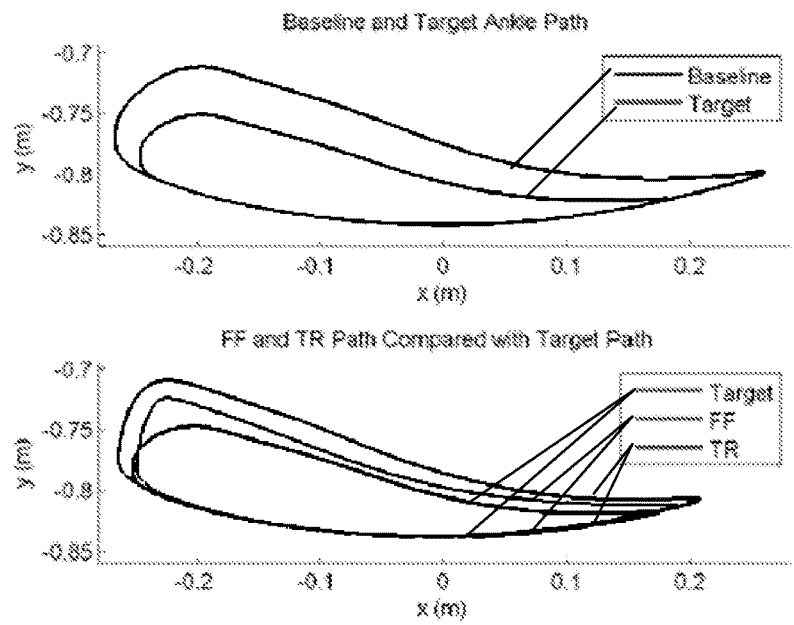
FIG. 5 target paths for evaluating a cable-driven leg manipulation device, according to one or more embodiments of the disclosed subject matter.

$F_n$ is normal to the target path and it will push the ankle point closer to the path. $F_t$ is tangential to the target path and pointing along the direction of movement. Thus, $F_t$ provides a push to move the ankle point along the target path.

$$\|F_n\| = K_n \cdot \left(1 - e^{-\left(\frac{2d}{r_n}\right)^2}\right) \quad (10)$$

$$\|F_t\| = K_t \cdot \left(e^{-\left(\frac{2d}{r_t}\right)^2}\right)$$

in which $K_n$ and $K_t$ are the gains of the force field, d is the distance from the ankle point to its nearest point on the target path. Eqn. (10) effectively creates two tunnels around the target path with diameters of $r_n$ and $r_t$ respectively. For the normal force $F_n$, the magnitude roughly equals to $K_n$ outside the tunnel and gradually decreases to zero inside the tunnel. For the tangential force $F_t$, the magnitude is zero outside the tunnel and gradually increases to $K_t$ inside the tunnel. FIG. 5 shows the change of $F_n$ and $F_t$ as a function of the normal distance from the target path d, and a qualitative depiction of the force field around a target path.

The force-field controller can have two modes: (1) a transparent mode and (2) a force-field mode. The transparent mode can be used for collecting the natural gait of the wearer. In the transparent mode, C-ALEX can try to minimize its interaction with the wearer, i.e., by simply compensating its own weight and not providing any assistance. Therefore, the required joint torque U in the transparent mode can be given by:

$$U = G(q), \quad (11)$$

in which G(q) is the gravity terms in Eqn. (1).

The force-field mode can be used to assist the wearer to track the target ankle path. In the force-field mode, C-ALEX can generate the aforementioned force field in addition to compensating for its own weight. The required joint torque U in the force field mode can be found by:

$$U = J_e(q)^T F + G(q), \quad (12)$$

where q is the generalized coordinate and $J_e(q)$ is the Jacobian matrix of the end effector.

With the joint torque U obtained, the force-field controller can use the cable tension planning to calculate the selected tension for each cable and send it to the low level controller. In one or more embodiments, the low level controller can include multiple parts or modules, for example, at least three modules. For example, the low level controller can include: (1) a feedforward part using the motor constant, (2) a friction compensation part using the motor's friction-speed model, and (3) a close loop PID controller using the feedback from the loads cells in the cables. The low level controller can control the motors to generate tensions that closely follow the selected tensions calculated from the high level controller.

Figure 6:
FIG. 6 is a schematic diagram illustrating aspects and timing of an experimental protocol for evaluating a cable-driven leg manipulation device, according to one or more embodiments of the disclosed subject matter.

An experiment was conducted to evaluate the performance of C-ALEX embodiments. The experiment verified that C-ALEX embodiments, with the force field controller, can assist a subject to track target ankle path. The experiment had subjects tracking a target ankle path with C-ALEX in both the force-field (FF) mode and the transparent (TR) mode. Six subjects participated in the experiment. The subjects were all male, aged between 20 and 35 years. FIG. 6 shows the protocol of the experiment.

During an experiment session, C-ALEX was fitted onto the right leg of the subject, and the experimenter took a measurement of the lengths of the right thigh and shank of the subject as well as the locations of the adapters, and then input these measurements into the controller. The subject was first instructed to walk on a treadmill to get familiar with walking with C-ALEX. The speed of the treadmill was adjusted to be the subject's comfortable walking speed. C-ALEX was put into transparent mode during this session. This familiarization session lasted for 4 minutes. Then a 2 minutes break was given to the subject. Following the break is a 4 minutes baseline session. During this baseline session, C-ALEX stayed in the transparent mode. The subject was instructed to walk naturally during this session. After the baseline session, another break of 2 minutes was given. The next session was the force-field (FF) session that lasted for 4 minutes. During this session, a target ankle path as well as the movement of the subject's right leg in the sagittal plane was displayed on a monitor placed in front of the subject. The subject was instructed to try to walk as closely to the target path as possible. C-ALEX was set into force-field mode during this session to help the subject follow the target ankle path. The subject took another 2 minutes break after the FF session. The last session is the transparent (TR) session. During this session, the subject was still instructed to follow the target ankle path displayed on the screen, but C-ALEX was switched to the transparent mode and was not helping the subject follow the target path. This TR session was 4 minutes long. After the experiment, the joint angles and ankle path during each session were recorded and analyzed.

During the baseline session, the joint angles and the ankle path were recorded. Data during the first and last minutes were discarded. The remaining data were divided into gait cycles at the anterior most point of the ankle path and averaged across the gait cycles to obtain the averaged joint angles in a single gait cycle. The averaged joint angles were then reduced by 20% to create an ankle path that is both shorter and shallower than the baseline ankle path. The part of FIG. 8 shows the baseline path and the modified path (Target) from a representative subject. This modified path was then used as the target ankle path in the FF session and TR session. The ankle path during the FF and TR session were recorded, cut and averaged the same way as was the baseline path. The average ankle path during the FF and TR session of the same representative subject are plotted in FIG. 5. Compared with the target path, it can be observed from the figure that the FF path is closer to the target path than TR path, which demonstrated the effect of the force-field controller of C-ALEX.

Figure 7:
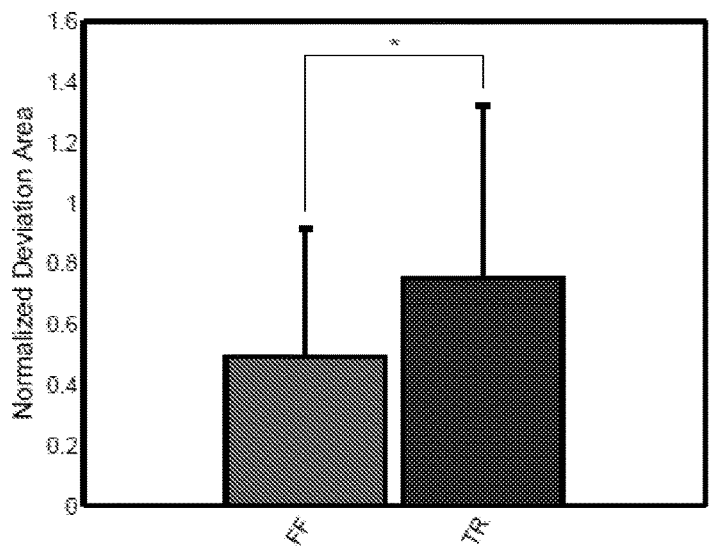
FIG. 7 is a graph of mean and standard deviation of normalized error area in force-field and transparent sessions using a cable-driven leg manipulation, according to one or more embodiments of the disclosed subject matter.

To quantify the effectiveness of C-ALEX, the normalized error area (NEA) of the FF path and the TR path were calculated and compared. FIG. 5 shows the deviation area of the baseline path (shaded), the deviation area of the FF path (shaded) and the deviation area of the TR path (blue shaded area). The NEA of the FF(TR) path is calculated as the ratio between the deviation area of the FF(TR) path and the deviation area of the baseline path, the ratio of the respective shaded areas divided. A smaller NEA suggests the path closely overlaps the target path. FIG. 7 shows the average NEA from all subjects. The average NEA in the FF sessions is 0.493±0.421 (mean±standard deviation), and the average NEA in the TR sessions is 0.751±0.572 (mean±standard deviation). Because 6 subjects were used, the Wilcoxon signed rank test was used to test the difference between NEA in FF sessions and NEA in TR sessions. The results show that NEA in FF sessions is significantly smaller than that in TR sessions ($p=0:031$). This result illustrates that that C-ALEX with force-field can help the subject to follow a prescribed ankle path.

Figure 8A:
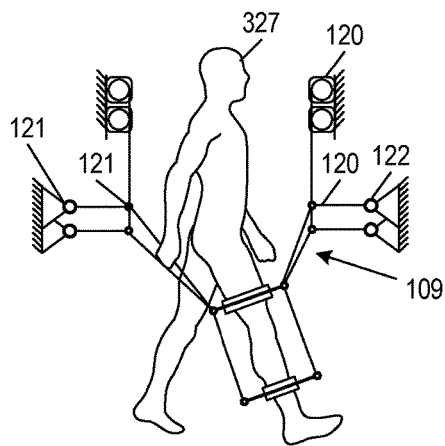
FIG. 8A schematically illustrates a cable driven leg manipulation device showing features including pivoting cable locators and fixed winches, features that may be used in any of the embodiments and devices that can be replicated for both legs, according to embodiments of the disclosed subject matter.

FIG. 9A shows a representative kinematic schematic diagram of a C-ALEX embodiment. Winches 120 draw cables 109, which are affixed to the ends of keeper links 120 that pivot when the cables 109 are drawn. The keeper links 120 may act as a cable guide to allow for more compact arrangement or other attributes such as greater clearance for hand swing while walking. Instead of keeper links 120, fixed links with sliding cable guides, as shown in FIG. 8C at 127, at the same positions as the fixed joints 121 may also be used. Note that fixed revolute joint bases may be offset in the dimension into the figure plane as may be the winches 120. FIG. 8C shows a variant in which the affixation points 123 of the thigh adapter 280 are lowered.

Figure 8B:
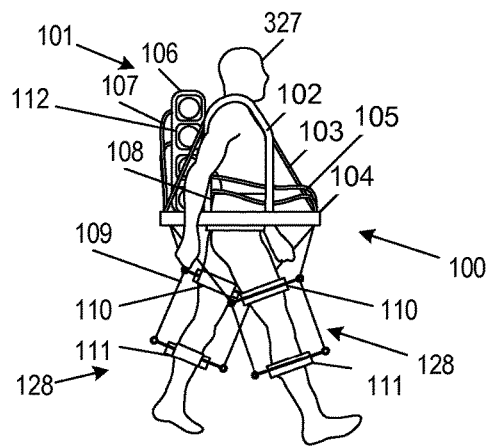
FIG. 8B schematically illustrates a cable driven leg manipulation device showing features including wearable mechanisms, features that may be used in any of the embodiments and devices that can be used for one leg or both legs, according to embodiments of the disclosed subject matter.
Figure 8C:
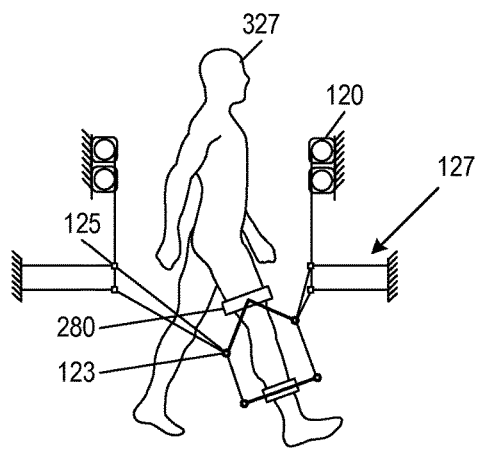
FIG. 8C schematically illustrates a cable driven leg manipulation device showing features including pivoting cable locators, fixed winches, and diagonal thigh adapter links, features that may be used in any of the embodiments and devices that can be replicated for both legs, according to embodiments of the disclosed subject matter.

Referring to FIG. 8B, a C-ALEX embodiment 100 is supported by a backpack arrangement 101 with harness 102 which may be worn by a subject 327. The weight may be partly or fully supported by a hip adapter 108. Winches 112 and a battery pack or corded AC power converter may be supported in the backpack 101 to provide power to the winches. A controller (not shown) may also be incorporated in the backpack 101. Stiffeners or tethers indicated figuratively at 103 may be provided to inhibit rotation between the harness 102 and extensions 104 of the adapter 108 through which cables 109 are guided. Thigh adapters 110 and shank adapters 111 as well as other features may be as described in connection with other embodiments. Note that FIG. 8B shows bilateral exoskeletons 128—one for each leg, which is a feature that any of the embodiments can have. Tension can be fed between the winches 112 and the cables 109 through Bowden cables 105.

Figure 8D:
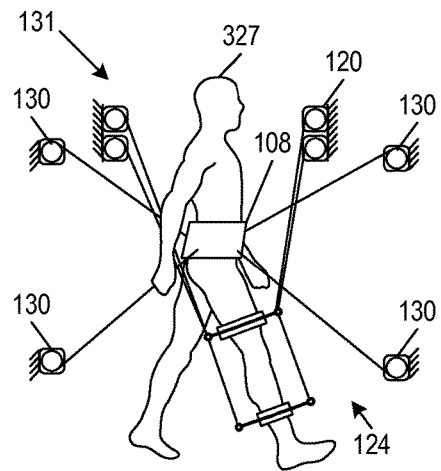
FIG. 8D schematically illustrates a cable driven leg manipulation device showing features including fixed winches and a hip actuator, features that may be used in any of the embodiments and devices that can be replicated for both legs, according to embodiments of the disclosed subject matter.
Figure 8E:
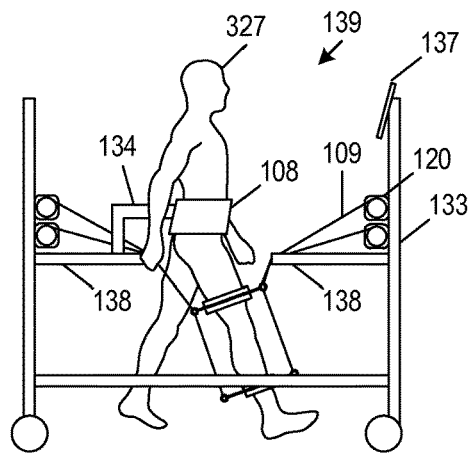
FIG. 8E schematically illustrates a cable driven leg manipulation device showing features including winches affixed to a mobile frame and pelvis adapter, features that may be used in any of the embodiments and devices that can be replicated for both legs, according to embodiments of the disclosed subject matter.

Referring now to FIG. 8D, in another C-ALEX embodiment 131, winches 130 are directly attached to hip adapter 108 to apply hip manipulation forces to modify the gait. This feature, which is combinable with the C-ALEX embodiments is discussed further below in connection with the A-TPAD embodiments. FIG. 8E shows a C-ALEX embodiment 132 in which the winches 120 are affixed to a mobile frame 133. A support 134 connects a hip adapter 108 to the mobile frame 133. The frame 133 may be passive or have motor 135 driven wheels 136 (See FIG. 8F). Alternatively, the wheels 136 may be fitted with encoders to provide a signal for use in detecting and/or logging gait pattern and/or progress. A controller may be supported on the frame 133. In the embodiment of FIG. 8E, the cables 109 are guided by standoffs 138 which support the cables 109 in a position such that they comfortably clear the legs of subject 327. The frame 133 may carry a display 137 or audio subject interface for interaction with the subject 327. The display 137 may show a feedback graphic that can act as a visual aid in coordinating and pacing interaction with the C-ALEX embodiment 133.

Figure 8F:
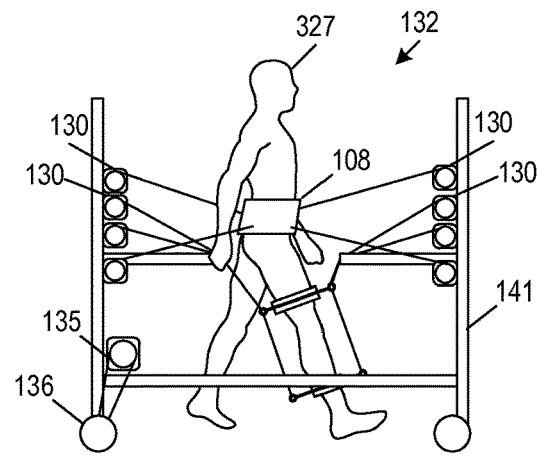
FIG. 8F schematically illustrates a cable driven leg manipulation device showing features including winches affixed to a mobile motor-driven frame and 2 DOF pelvis adapter, features that may be used in any of the embodiments and devices that can be replicated for both legs, according to embodiments of the disclosed subject matter.

Referring now to FIG. 8F winches 130 are directly attached to hip adapter 108 to apply hip manipulation forces to modify the gait. This feature, which is combinable with the C-ALEX embodiments is discussed further below in connection with the A-TPAD embodiments. Here, the winches 130 are attached to a mobile frame 141. The frame 141 may be passive or it may have motor 135 driven wheels 136. Alternatively, or in addition, the wheels 136 may be fitted with encoders to provide a signal for use in detecting and/or logging gait pattern and/or progress. The forces applied to the hip adapter 108 may take advantage of inertia and rigidity of the frame 141. For example weights may be attached to the frame 141 to stabilize it when impulses are applied to the hip. Motorized wheels can be controlled to generate a compensating impulse to neutralize the reaction forces when impulses are delivered to the hips in the mobile frame 141. For example, an output control profile may spool out the cables on a first side opposite the direction of the impulse (to the hip adapter 108) to be applied while the wheels drive the frame 141 in that first direction for a short interval whereafter the cables are spooled in the opposite direction to deliver the impulse, halting the wheel-driven motion and delivering the impulse to the hip adapter 108. Such a scheme may involve very small displacements.

Figure 8G:
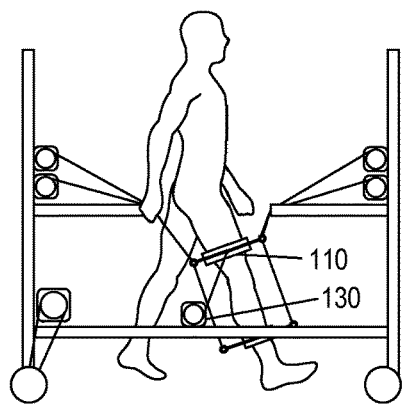
FIG. 8G schematically illustrates a cable driven leg manipulation device showing features including winches affixed to a mobile motor-driven frame and 2 DOF thigh adapter that receives flexion and lateral traction forces, features that may be used in any of the embodiments and devices that can be replicated for both legs, according to embodiments of the disclosed subject matter.
Figure 8H:
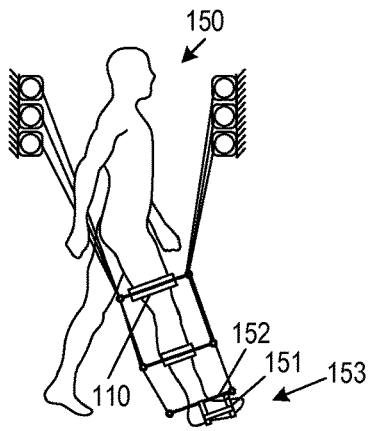
FIG. 8H schematically illustrates a cable driven leg manipulation device showing features including fixed winches and an ankle adapter supporting active plantar/dorsiflexion motion, features that may be used in any of the embodiments and devices that can be replicated for both legs, according to embodiments of the disclosed subject matter.

FIG. 8G illustrates an alternative placement for cables that induce a side-to-side motion by applying laterally-directed impulses to the thigh adapter 110. In control embodiments, the controller may operate to apply lateral impulses only when the subtending foot is predicted to be, or is detected to be, in contact with the ground such that the impulse tends to move the pelvis rather than cause hip abduction. Here a suitably positioned and configured winch 130 may be provided. FIG. 8H shows an embodiment of a C-ALEX system 150 in which an ankle adapter 153 is provided. A link 152 imparts torque to a foot or shoe adapter 151. The foot or shoe adapter 151 may strap around the foot or shoe of the subject 327. Alternatively, the foot or shoe adapter 151 may attach to a Velcro plate attached to the top of the subject's 327 shoe. Other attachment devices are possible. The tension of the cable that terminates at the link 152 may pass by, without applying any force to, the shank adapter. The tension of the cable that terminates at the link 152, at certain points in the gait cycle, must be compensated by the controller because they may generate a moment in the thigh adapter.

Figure 8J:
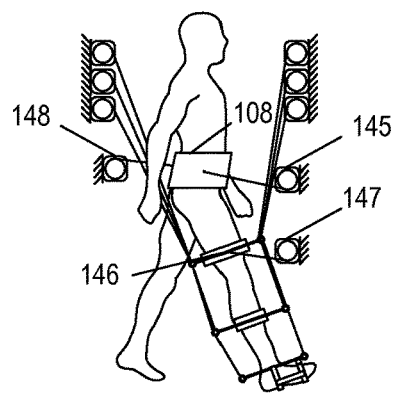
FIG. 8J schematically illustrates a cable driven leg manipulation device showing features including fixed winches, an ankle adapter supporting active plantar/dorsiflexion motion and a hip adapter for lateral displacement forces, features that may be used in any of the embodiments and devices that can be replicated for both legs, according to embodiments of the disclosed subject matter.
Figure 8K:
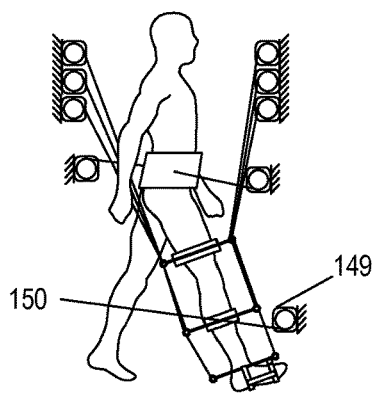
FIG. 8K schematically illustrates a cable driven leg manipulation device showing features including fixed winches, an ankle adapter supporting active plantar/dorsiflexion motion and a thigh adapter for lateral displacement forces, features that may be used in any of the embodiments and devices that can be replicated for both legs, according to embodiments of the disclosed subject matter.

Referring to FIG. 8J, a combination of lateral winches 145, 148 and 147 that draw cables attached to the hip adapter 108 and the thigh adapter. The winch 148 is on an opposite side of the winch 147 such that by drawing both simultaneously, a hip abduction moment can be applied to the thigh adapter 146. In embodiments, the controller applies this type of moment when the foot is not in contact with the ground which may be detected (e.g., foot sensor) or predicted by phase of gait cycle. FIG. 8K shows a variant of this embodiment in which the lateral traction force is applied to the shank adapter 150 by a respective winch 149.

FIG. 8L schematically illustrates a cable driven leg manipulation device showing features including fixed winches, thigh and shank adapters with extensions that provide for clearance, features that may be used in any of the embodiments and devices that can be replicated for both legs, according to embodiments of the disclosed subject matter. A cable-actuated system 214 has thigh and shank adapters 212 and 213 whose extensions are angled or positioned so that the separation between the extensions 217F on the front of the knee (the extension side) are closer together and the extensions 217B on the back side (flexion side) of the knee they are further apart. This allows the leg to bend without risk of the cable contacting the body. This feature may be employed with all of the embodiments.

FIG. 8M schematically illustrates a cable driven leg manipulation device 131 showing features including fixed winches, two shank adapters supporting active plantar/dorsiflexion motion and a thigh adapter for lateral displacement forces, features that may be used in any of the embodiments and devices that can be replicated for both legs, according to embodiments of the disclosed subject matter. By independently controlling the shank at two points, a similar level of control may be provided to a walking subject's legs as provided by the separate thigh and shank adapters.

FIGS. 8N and 8P shows a cable driven leg manipulation device 218 with separation between the thigh and shank adapters optimized for a fixed separation between them to accommodate subjects 327A and 327B of different heights or proportions, features that may be used in any of the embodiments and devices that can be replicated for both legs, according to embodiments of the disclosed subject matter. The positions of the winches 219, 220 may be optimized for a predefined separation distance 216 between the thigh and shank adapters 212, 213. When subjects whose limbs have different size or proportions, the separation distance can be retained and the winches 219, 220 may remain in an optimal position for control.

The features described with reference to FIGS. 8A through 8P may be omitted and/or interchanged to form new embodiments. Although not shown, all the cables may include tension sensors (load cells) to provide feedback to the controller. Also, although not mentioned, all the embodiments may include controllers according to the described controller embodiment of FIGS. 4A and 4B.

FIG. 25A shows details of a limb adapter 419 that may be used in any of the embodiments having an adapter for cable attachment to a limb or other body part. A cuff portion 424 has a boss portion 425 for mounting to a lever mount 420 with extension arms (also referred to as "fixed extensions") 422A, 422B and 423A, 423B. The boss portion 425 of the cuff portion 424 may be secured with screw fasteners or any other suitable means to transmit torque forces resulting from moments applied by the cables to the lever mounts 420 The ends of the extension portions 422A, 422B of a side that faces the flexing side 428B of a joint, such as the back of the knee may be displaced further apart (thereby lengthening the spanning length of cable 430 between them). Concomitantly, the ends of the extension portions 423A, 423B of a side of the lever mount 420 that faces the extension side 428F of a joint such as the front of the knee may be displaced further apart (thereby shortening the spanning length of cable 430 between them).

FIG. 25B shows an optional cuff configuration for use with any of the cable actuated adapters that apply torque to limbs. The cuffs may be configured with longitudinal extensions 402 that may reduce the pressure on the limb for a given torque applied to the limb. As shown at 400, the longitudinal extensions 42 may be stiffened by stiffeners 408 such as ductile metal rails. The stiffeners 408 may be bent to make the shape as comfortable as possible and allow adjustment as experience with use of the cuff 400 accrues. The material of the cuff 400 may be thinner as it progresses toward the tips of the extensions 402. The cuffs may be made of thermoplastic (e.g., polyethylene) as is commonly used in the custom orthosis industry. Levers 414 may be attached to the stiffeners directly which may avoid the need for a stuff member to wrap around the cuff as in the embodiments described elsewhere and indicated at 272 in FIG. 2 for example. The cuff configuration of FIG. 25B may also be used with lever mount 420 as in FIG. 25A by forming a cuff similar to the cuff portion 424 with extensions 402 formed therein. Note that the term lever mount should be clear in terms of its relationship to all elements identified as "adapters" in the various embodiments.

Embodiments with A-TPAD Features

Figure 9:
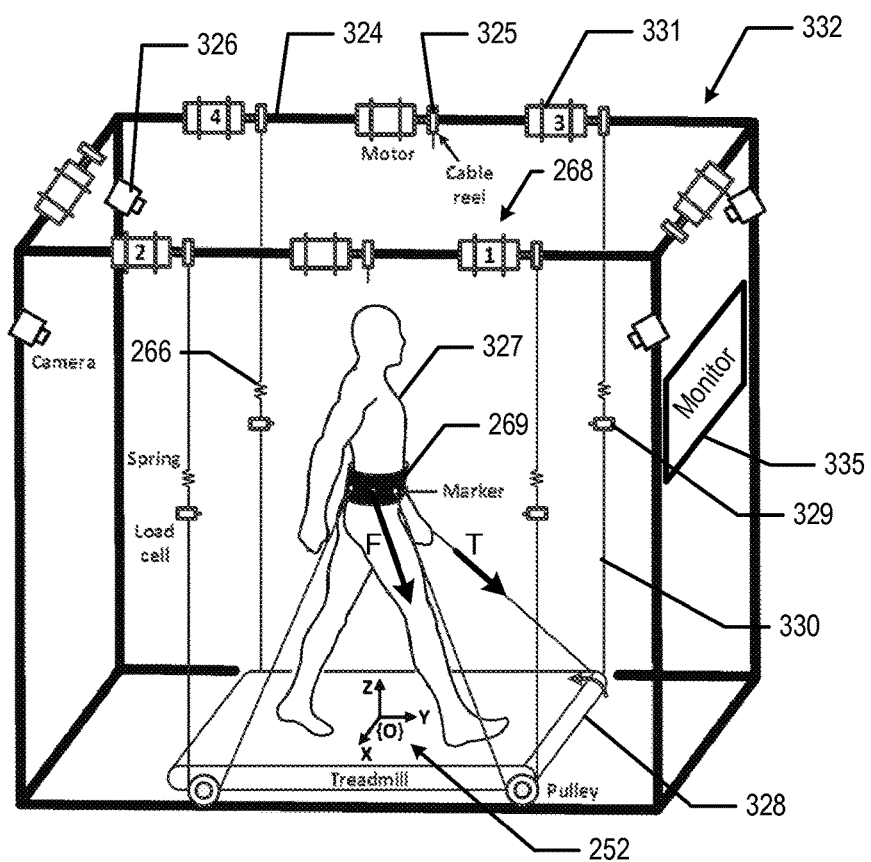
FIG. 9 is a schematic diagram of an active tethered pelvic assist device (A-TPAD), according to one or more embodiments of the disclosed subject matter.

FIG. 9 shows an A-TPAD embodiment. Winches 268, each including a motor 331 and pulley 325 are mounted on a rigid frame 324. Cables 330 drawn by the winches 268 are routed using pulleys to the subject's pelvis through a pelvis adapter. The system allows the flexibility to choose the number of motors and the locations of routing pulleys to achieve different cable configurations. Load cells or tension sensors 329 are used to measure the cable tensions and a spring is placed in series between the motor and load cell. A ten-camera 326 motion capture system is used to track the cable attachment points and human motion based on markers attached to the subject 327 or the adapter. The features of the embodiment of FIG. 9 are the same in evident respects as those of the embodiments of FIGS. 1A and 1B in terms of the control of the cable tensions. The essential difference is that the tensions are applied to a hip adapter 269 rather than adapters for the legs as in FIGS. 1A and 1B. As in the embodiments of FIGS. 1A and 1B, the tension sensors are used by a controller to detect motions of the subject to generate error estimates between a target and a current movement. Control aspects are discussed further below.

Embodiments of the disclosed subject matter include weight-bearing approaches that can help subjects achieve a longer stance time. In one or more embodiments, a force, with magnitude equal to a percentage of the subject's body weight (BW), for example, 10% of the subject's body weight (BW), can be applied on the pelvis along a direction parallel to the right leg. This force vector may be directed from the right anterior superior iliac spine towards the right ankle. The effect of such an asymmetric force vector was tested on a group of healthy subjects. An active tethered pelvic assist device (A-TPAD), which is a cable-driven pelvic robot illustrated in FIG. 9, can be used to apply the selected force vector on the subject's pelvis during the full gait cycle. In FIG. 9, global coordinate system 252, {O}: XYZ, is set at the center of the treadmill, $T_i$: $i^{th}$ the cable tension, and $F_d$: selected force-moment vector.

As in the other embodiments, the A-TPAD system embodiments may actively involve the subjects in the training to enhance the learning effects. Voluntary participation of subjects during training can be enhanced, for example, through visual feedback. Conscious correction can expedite learning of a new walking pattern. Thus, a second group of healthy subjects was given visually the information of stance time during walking. Subjects were expected to put extra effort to resist the asymmetric force vector to retain the stance time symmetry.

Winches 268 may include AC single phase servo motors with gearboxes (e.g., from Kollmorgen, Pennsylvania) to actuate the cables 330. A maximum continuous tension of 157 N can be applied in each cable. Tension sensors 329 (load cells—e.g., from Transducer Techniques, California) may be connected in each cable 330 to measure the cable tensions. Springs 266, in series with the tension sensors 329, may have a predefined stiffness, for example, 2.5 N/mm (14.21 lb/in). Also, as in other embodiments, a motion capture system (e.g., Bonita-10 series from Vicon, Denver) can be used to track the cable attachment points and also human motion during the experiment.

Figure 10:
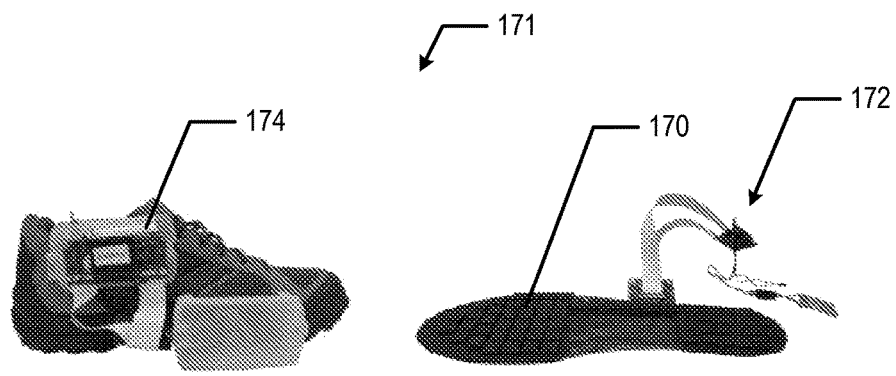
FIG. 10 is an image of instrumented shoes with pressure sensitive insoles used to record vertical ground reaction force.

Instrumented shoes 171 with pressure-sensitive insoles 170, for example, as shown in FIG. 10, were used to calculate the stance time from the plantar pressure data for visual feedback during walking. The shoes 171 may contain pressure sensors defining a range of alternate pressure sequences predicted for normal or abnormal gaits to permit the time of falling of the foot to the time of lift off and to indicate all phases between including the distribution and variation in the center of force from footfall to foot lift. The indications may be recorded and predictions of progress or diagnoses of gait abnormalities generated from the data using collaborative filtering or other machine intelligence techniques. In particular, the signals from the shoes may be used in presenting cues and visual feedback to help a subject acquire and maintain form during treatment, research, and/or diagnostic sessions. A pacing signal can be generated from other types of sensors, for example, sensors adapted to detect flexion of the sole rather than pressure due to the weight of the subject. Alternatively, pacing can be generated from video-acquired motion capture including event recognition. The instrumentation may communicate wirelessly using a transponder 172 or by means of a communication cable. In tested examples, each shoe had a matrix of 64 sensors in the insole for the transduction of the vertical component of the ground reaction force and an electronic board for signal processing and wireless transmission of data.

The tested embodiment of A-TPAD applies forces in 6 dimensions actuated by m cables. If m×1 vector T represents the tension in each cable then the applied external n×1 force moment vector F at the center of the pelvis can be expressed in terms of the cable tension vector and the system geometry (as shown in FIG. 1):

$$AT=F \tag{13}$$

where A is an n×m structure matrix, a function of the system geometry, and can be computed knowing the coordinates of the cables attachment points.

In a cable-driven system, cable tensions can only have positive values. In the case of an n degree-of-freedom cable robot, at least n+1 cables are used to generate the selected n×1 vector F. In one or more embodiments of the disclosed subject matter, the force vector can be applied on the pelvis while maintaining the moment components, resolved at the pelvic center, within a small range. Therefore, four cables can be connected to the hip brace and the lower part of the frame, as illustrated in FIG. 9. This choice of cable attachment points can minimize, or at least reduce, cable interferences with the hand motion during walking. Cable attachment locations on the frame, $P_i$s, are given in Table 2.

TABLE 2

| Cable Attachment Locations on the Frame | | | | |
|---|---|---|---|---|
| | $P_1$ | $P_2$ | $P_3$ | $P_4$ |
| X (m) | 0.62 | 0.59 | −0.50 | −0.51 |
| Y (m) | 0.75 | −0.80 | 0.74 | −0.80 |
| Z (m) | 0.13 | 0.12 | 0.14 | 0.13 |

A quadratic programming based optimization scheme can be used to solve Eq. (1):

$$\min \lfloor (\tfrac{1}{2}(T-T_P)^T(T-T_p)) \rfloor$$

$$\text{s.t. } A_{eq}T = |F_{eq}|, -F_{ieq} \leq A_{ieq}T \leq F_{ieq}$$

$$\text{and } T_{min} \leq T \leq T_{max} \quad (14)$$

where $T_p$ is a positive constant, added to the objective function to ensure non-zero cable tension values. $T_{min}$ and $T_{max}$ are the lower and upper bounds on the cable tension values. Further, $F_{eq}=[FX\ FY\ FZ]^T$ and $F_{ieq}=[MX\ MY\ MZ]^T$, where $A_{eq}$ and $A_{ieq}$ are respectively the first three and last three rows of the structure matrix A.

Figure 11:
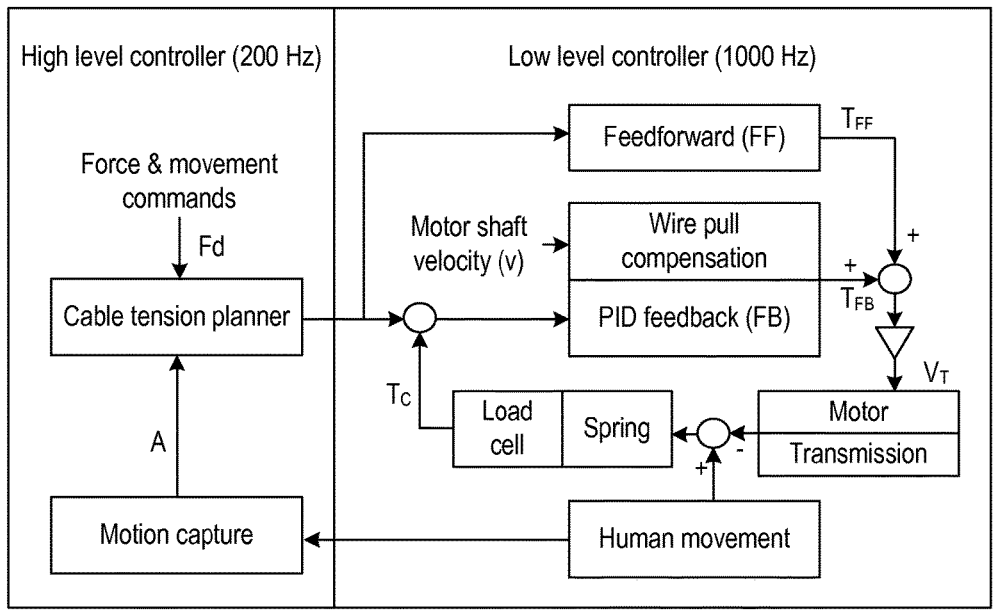
FIG. 11 is a schematic diagram of a controller for an active tethered pelvic assist device (A-TPAD), according to one or more embodiments of the disclosed subject matter.

The A-TPAD can include a controller (or multiple controllers), which can control the servomotors and actuation of the cables, among other things. The controller may be functionally described as two major components: low level and high level, as illustrated schematically in FIG. 11. The high level controller can determine the selected cable tension values $T_d$ to apply a selected force-moment vector $F_d$. The low level controller can implement these cable tension values using a feedback PID loop and a reference feedforward. A wire pull compensation model based on the motor velocity can also be included in the low level controller. Control may be implemented by a suitable host computer or embedded system. In examples tested, the controller was implemented in LabVIEW using a PXI real time controller (National Instrument, Austin).

For the low level controller, an open loop reference feed-forward (FF) term with a unit gain and a closed loop PID based feedback (FB) term can be implemented to achieve the selected cable tension values, $T_d$, during the experiment. The net voltage applied to the motor, $V_T$, can be the summation of the FF and FB outputs:

$$V_T = M_c(T_{FF} + T_{FB}) \quad (15)$$

where $M_c$ is the motor constant. The low level controller can be implemented, for example, on a real-time NI PXI system at 1000 Hz.

A cable in a cable-driven system can only be pulled but not pushed. In the current setup, a positive $V_T$ results in a cable to wrap around the cable reel, while a negative $V_T$ can potentially cause cable slackening during the experiment. From Eq. (3), $V_T$ could have negative values if $T_{FB} < -T_{FF}$. In some embodiments, the lower limit of the FB term output was limited such that $$(T_{FB})_{min} = -T_{FF} \quad (16)$$

Alternatively or additionally, $$(T_{FB})_{min} = -T_{FF} + T_{lim} \quad (17)$$

$$T_{lim} = -L\left(1 - e^{\frac{-\|v(t)\|}{v_{max}}}\right)$$

where v(t) is the cable velocity, L and $v_{max}$ are positive constants. These constants can be tuned to achieve a responsive controller avoiding any cable slackening. The term $T_{lim}$ was zero when the subject was not moving, i.e., when v was zero. This term approached –L exponentially with the cable velocity. Cable velocity can be calculated from the encoder data.

A motion capture system was used to monitor the human motion and cable attachment points to calculate the structure matrix, A. Reflective markers can be placed on three pelvic anatomical positions to define the pelvic coordinate system. The cable attachment points on the brace can be fixed in the pelvic coordinate frame and the locations of cable attachment points on the ground frame can be fixed in the global coordinate system. The markers placed on subjects' lower limbs can be used to calculate the direction of the selected force vector. Software (e.g., Vicon Nexus software) can be was used to monitor the markers at, for example, 200 Hz. Marker data can be accessed in Labview by calling a .NET assembly reference to the Vicon data software development kit (SDK).

The cable tension planner can be implemented, for example, on a real-time NI PXI at 200 Hz. A quadratic programming problem can be formulated to calculate the selected cable tension $T_d$ based on the selected force-moment vector $F_d$, as described in Eq. (2). The values of $T_p$ can be selected to be the cable tension values calculated in the previous step, to keep a smooth profile of cable tensions. For those instances, when the optimization problem does not yield a solution, previously calculated tension values can be used. Similarly, for instances where a marker is occluded, previously calculated tension values can be used.

Figure 12:
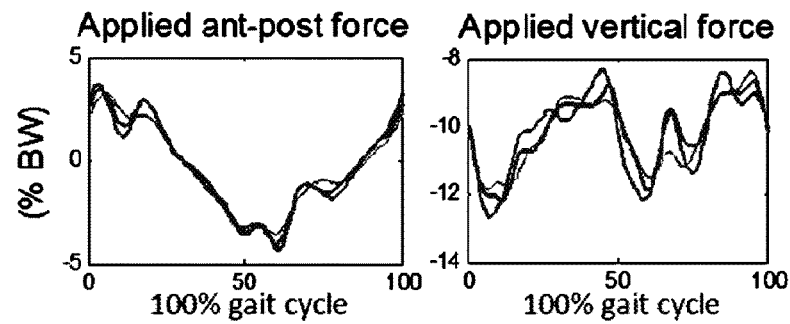
FIG. 12 show graphs of the applied for component in the anterior-posterior and vertical directions during training trials over a gait cycle for representative subject for a non-visual feedback group (row a) and a visual feedback group (row b)
Figure 12:
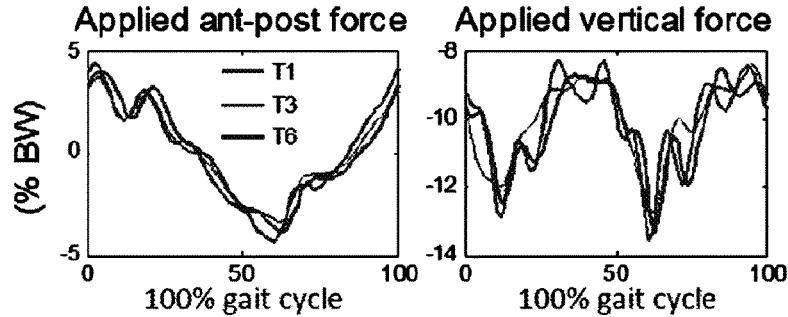

The top row of FIG. 12 (row (a)) illustrates gait events for both legs are identified, where HS refers to heel strike and TO refers to toe off. The initial and final single support (SS) and double support (DS) periods are also defined. The bottom row of FIG. 12 (row (b)) shows selected force vector data for a representative subject during the T1, T3 and T6 training trials. A gait cycle was defined from RHS to subsequent RHS.

Figure 13:
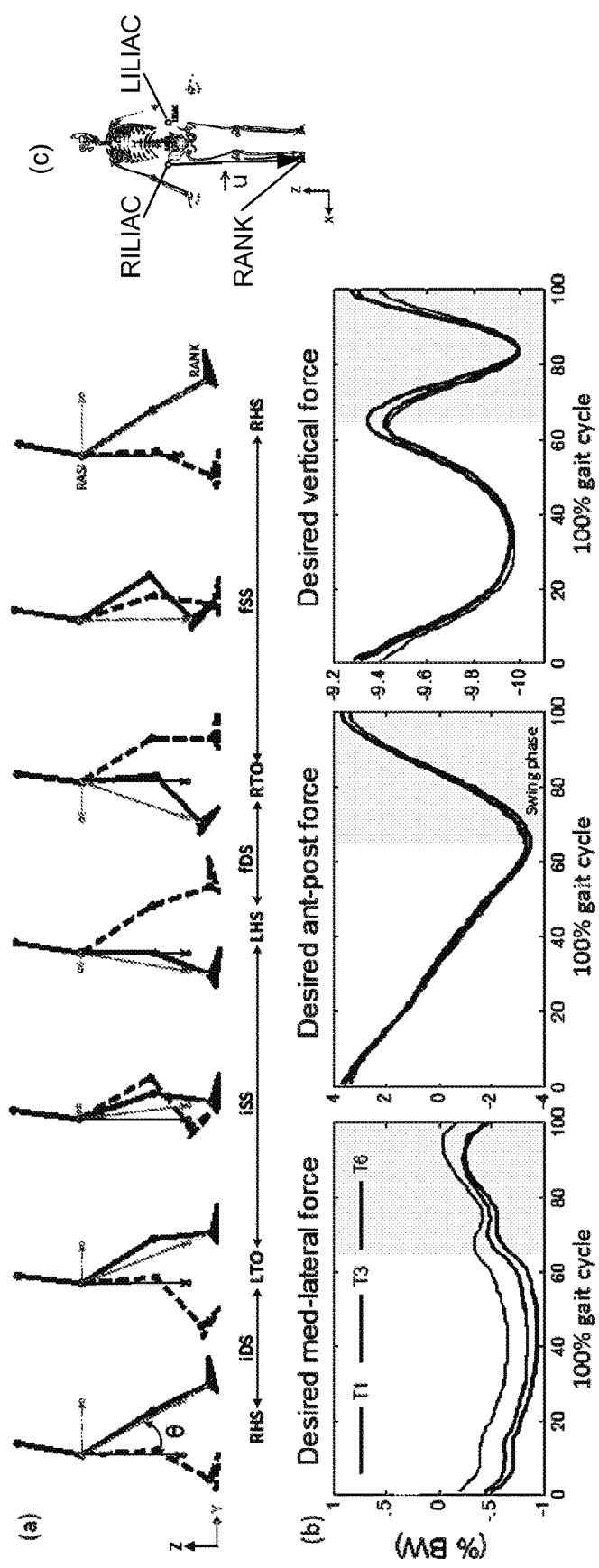
FIG. 13, part a, shows a sketch indicating the selected trend of the anterior-posterior and vertical force components over a gait cycle with gait events for both legs being identified, where HS refers to heel strike, TO to toe off, SS to the initial and final single support, DS to double support periods, θ defines the right limb angle; part b showing the applied force component in the anterior-posterior and vertical directions during training trials over a gait cycle for representative subject for a non-visual feedback group and a visual feedback group and part c showing a vector parallel to the right leg, û defined from the right iliac crest (RILIAC) anatomical position on the pelvis to the right ankle (RANK).

An asymmetric force vector was applied on the subject's pelvis and was directed along a vector parallel to the right leg over the full gait cycle. The selected force vector was expressed as:

$$\left. \begin{array}{l} F_d = \|F\|\hat{u} \\ \|F\| = 10\%\ BW \\ |M_{X,Y,Z}| \leq 6Nm \\ 5 \leq T \leq 60N \end{array} \right\} \Rightarrow \begin{array}{l} F_{eq} = [F_{dX}\ F_{dY}\ F_{dZ}]^T \\ F_{ieq} = [M_X\ M_Y\ M_Z]^T \\ 5 \leq T \leq 60 \end{array}$$

where $\hat{u}$ is a unit vector from the right anterior superior iliac spine (RASI) to the right ankle (RANK), as shown in FIG. 13. Thus, the medial-lateral, anterior-posterior and vertical components of the selected force varied with the right leg motion during walking ($F_{dX}$, $F_{dY}$ and $F_{dZ}$ respectively, refer to FIG. 1 for global coordinate system). The variations in the medial-lateral force component were small due to a relatively small motion of the foot in this direction over a gait cycle. The force component in the anterior-posterior direction, Y, was either positive or negative depending on whether RANK was anterior or posterior to RASI, as shown in FIG. 13(a). Therefore, at right heel strike, RHS, (1 and 100% gait cycle) and at right toe off, RTO, (approximately 63% gait cycle), the anterior-posterior force component had maximum positive and negative values respectively. The force component in the vertical direction, Z, was always directed downward.

Further, the vertical force component reached the maximum magnitude (almost 10% BW) two times in each gait cycle around each leg's mid swing phase, where the anterior-posterior force component was equal to zero. The lowest magnitude of the vertical force was at RHS and RTO. Therefore, the selected force vector was mainly distributed in the sagittal plane. Additionally, the proportion of right swing and right stance phases in a gait cycle decide the rate of force change. Selected force data from the training trials of a representative subject are shown in FIG. 13(b). The force along the Y and Z directions varied at a higher rate during the right swing phase.

Data from the instrumented shoes were acquired at 100 Hz and processed by a remote PC using Labview. The sensors' voltage signals were converted to force values using a predefined calibration function. The sum of the force from all sensors defined the vertical ground reaction force, vGRF, and the barycenter of the forces in the plantar surface defined the center of pressure, CoP. The CoP values were calculated only when the ||vGRF||>20N. The CoP was then used to segment the gait cycle into stance and swing phases. For each foot, the stance time ($ST_L$ and $ST_R$), was calculated online based on the gait segmentation, i.e., each time a toe off was detected a new value of the stance time was calculated as the period from the last heel strike to the current toe off. A screen in front of the subject was used to show the duration of the last gait cycle stance time of both legs. Stance time was expressed by means of two bars, whose height was proportional to the stance duration.

Four male subjects (23.0±2.7 years old, 65.7±9.2 kg, 1.75±0.06 m, right dominance of the lower limb) were randomly assigned to either the Visual Feedback (VF) or Non Visual Feedback (NVF) group. Two subjects were enrolled for each VF and NVF groups. Subjects were asked to wear a hip brace with cable attachment points, reflective markers and the instrumented shoes. Bilateral vertical ground reaction forces and gait events (i.e., heel strikes and toe offs) were collected by the instrumented shoes.

The experimental protocol consisted of three sessions: Baseline (BL), Training (T) and Post-training (PT). During the BL, subjects walked on a treadmill for 4 minutes. Data collected during the last minute was used in the analysis as reference. During the T, four cables were attached to the hip brace to apply the selected asymmetric force vector while the subjects walked for 16 minutes. Subjects assigned to the VF group were trained with the additional visual feedback. Before starting the T, the experimenter instructed the subjects to walk while keeping their left and right stance times the same. No instructions were provided to subjects from the NVF group. Data were recorded six times for 1 minute duration at start, 3rd, 6th, 9th, 12th and 15th minutes. These data were referred to as T1, T2, T3, T4, T5, and T6. During the PT, the cables were removed and the subject walked for another 10 minutes. Data were recorded four times for 1 minute duration at start, 3rd, 6th and 9th minutes. These data are referred to as PT1, PT2, PT3 and PT4. During BL and PT, all subjects walked without visual feedback. Walking speed during the experiment was kept the same at 3.8 km/h for all subjects.

Pressure and kinematic data were stored and analyzed offline to extract the kinetic and spatiotemporal gait variables. Data were low-pass filtered (zero-lag, 4th order Butterworth low-pass filter) with cut off at 6 Hz. For each subject, the last 5 strides of trials BL, T3, T6 and PT4 and the first 5 strides of trials T1 and PT1 were selected for data analysis. Data were averaged across the selected strides in order to have a representative gait cycle for each trial. For each leg a gait cycle was defined from a heel strike to subsequent heel strike of the same foot. Gait events were used to determine the durations of Double Support (iDS & fDS) and Single Support (iSS & fSS). The cadence was defined as the inverse of time elapsed from two subsequent contralateral heel strikes and reported as number of steps per minute. The stance time (ST) for a leg was defined as the time duration between a heel strike and the following toe off of the same leg. The relative duration of fDS as the percentage of right stance time was extracted for each cycle. The Stance Symmetry Index (SSI) was calculated as the ratio of the left to the right stance time. Vertical ground reaction force, vGRF, curves were subdivided into strides and time interpolated to 100% gait cycle. The left and right maximum force peaks (namely LvGRFp and RvGRFp) over a gait cycle were extracted from the vGRF curves. The vGRF and SSI values during different trials were normalized by dividing each value by respective mean BL value.

Regardless of the group, all subjects completed the experiment without difficulty. The components of the applied force on the pelvis in the anterior-posterior, $F_Y$, and the vertical, $F_Z$, directions during training are plotted for a representative subject from both groups in FIG. 5. The $F_Y$ values varied within 5% BW and the $F_Z$ between −8 to −14% BW over a gait cycle from trial T1 to T6. Root mean square error (RMSE) between the selected and the applied force values in the medial-lateral, anterior-posterior and vertical directions for both groups were under 0.5, 1 and 1.5% BW respectively. These differences may be due to unaccounted human dynamics during walking. The applied moments at the pelvic center were within the selected level of ±6 Nm for both groups. This shows that A-TPAD applies the selected asymmetric force vector consistently over the training session.

Figure 14:
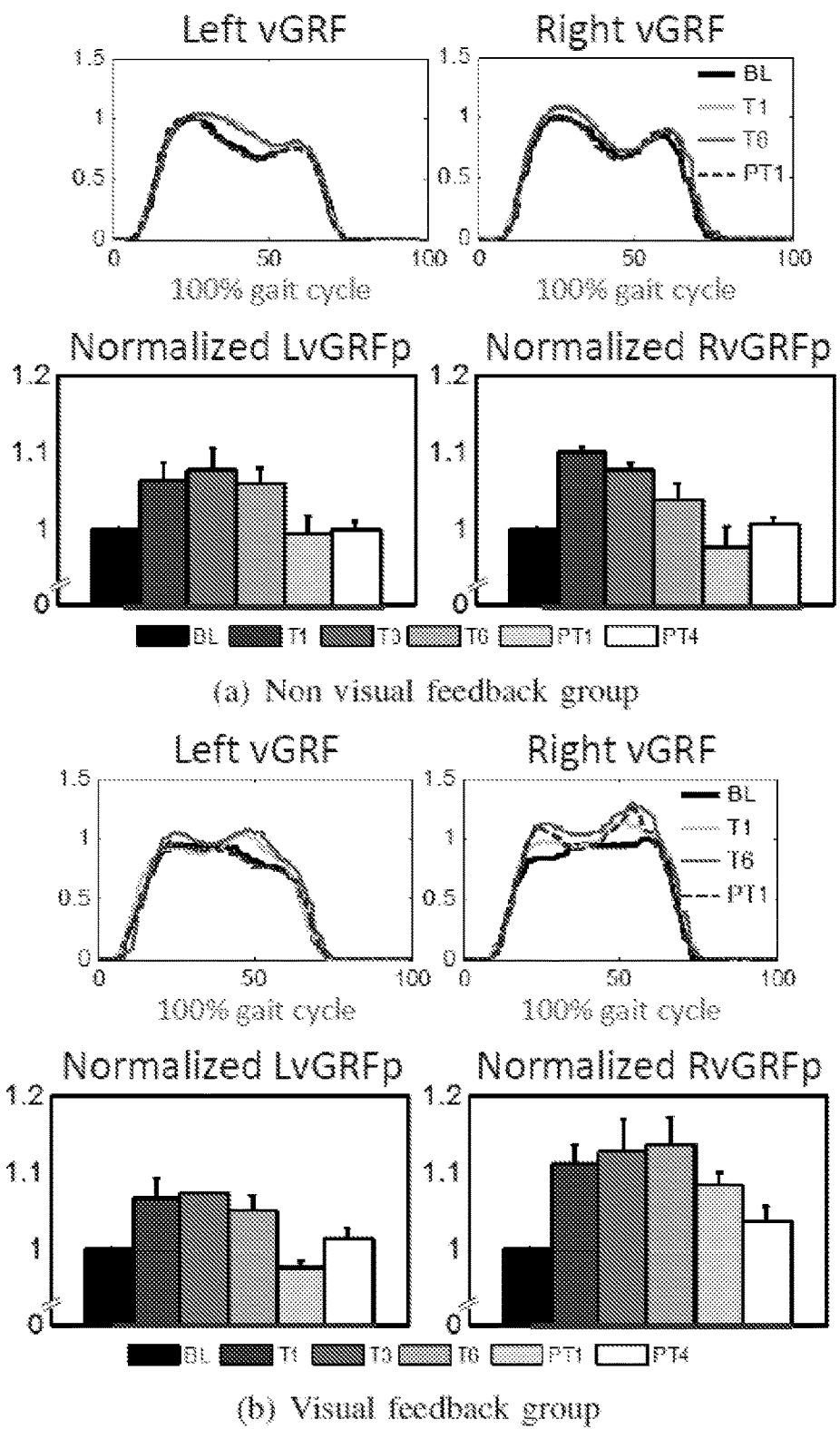
FIG. 14 shows graphs of left and right-normalized vertical ground reaction force values over a gait cycle and the corresponding peak values during different experimental trials for a non-visual feedback group (row a) and a visual feedback group (row b).
Figure 15A:
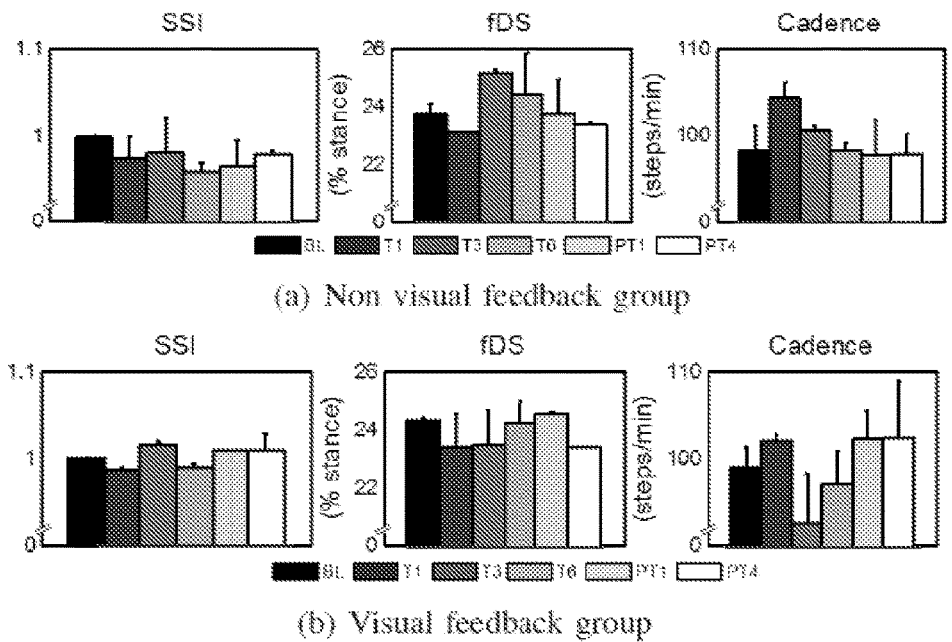
FIG. 15A are graphs of the average values of stance symmetry index, cadence and the percentage of the right stance time spent in fDS during different experimental trials for a non-visual feedback group (row a) and a visual feedback group (row b).

FIG. 14 (grid a) plots the vertical ground reaction force, vGRF, curves for a representative subject and the average of the peak left and right vGRF values across subjects for different trials. The vGRF values of both legs were higher during the training session due to the vertical component of the applied force vector. In FIG. 15A, stance symmetry index, SSI, average values have been plotted for different trials across subjects. In the presence of the applied force vector, lower SSI values were reported and this reduction was due to longer right stance time values. Interestingly, longer right stance time values were also reported during the post-training session when the applied force vector was removed. The percentage of the right stance time that subjects spent in the final double support, fDS (LHS to RTO), decreased as an immediate response to the applied force, but these values increased above the baseline, BL, level with the progression of training. These changes in the right stance time and fDS values were due to the added resistance by the applied force vector to the subjects' motion around RTO, which would have required extra push-off effort. The immediate response of subjects to the applied force was also to increase their cadence values. Though, these values gradually reduced back to the baseline level with the progression of training. Hence, the asymmetric force vector applied on the pelvis that varied with the right leg motion showed expected higher ground reaction forces with both legs and longer right stance time.

FIG. 14 (grid b) plots the vGRF curves for a representative subject and the average of the LvGRFp and RvGRFp values across subjects for different trials. Similar to NVF, higher vGRF values were reported during training with both legs. Interestingly, right leg values were comparatively higher than the left leg during the training session. Higher RvGRF values were also reported during the post-training session. The average SSI values for this group did not show a particular trend. Since, feedback was provided in terms of stance time, subjects put conscious effort in maintaining the stance time symmetry. Notably, longer stance time values were reported for both legs compared to BL during the training session. Further, fDS as percentage of right stance time remained lower or close to the BL values during the training session. These changes in the fDS and SSI values implied that subjects, in presence of feedback, resisted the applied force action, which required higher push-off effort at RTO. This extra effort of subjects was also reflected in the higher right vGRF values during training. The higher RvGRF values during post training therefore suggest subjects' adaptation to the applied force vector. Additionally, subjects also increased the average cadence values as an immediate response to the applied force, but these values decreased below the BL level with the progression of training session. Hence, the use of visual feedback in addition to the applied asymmetric force vector showed expected enhancement of the training effects.

Figure 15B:
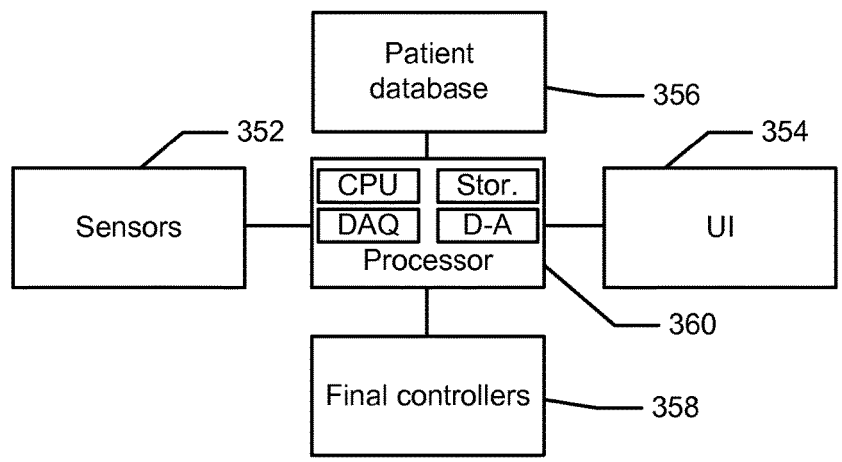
FIG. 15B shows a schematic diagram of a controller 410 for a movement training apparatus, according to embodiments of the disclosed subject matter.

Referring now to FIG. 15B, a controller 410 for the movement training apparatus 299 is the same for the leg actuators 300 and the trolley platform 102. The controller 410 has a processor 410 with data storage that may include non-volatile data storage and random access memory elements (Stor.). Further it may have a data acquisition portion (DAQ) that interfaces to sensors for receiving signals from the various sensors of the described embodiments. It may have output components such as audio and video adapters as well as input interfaces to support interaction with one or more subject interface (UI) elements 404. It may have a digital to analog converters (D-A) for output signals to final controllers 408 that drive motors. It may have a processing unit (CPU) for numerical computation and execution of programmatic instructions. Apart from the data storage, it may be connected to data sources including databases, for example a patient database 406 with patient profiles such as the patient's particular limb lengths, diameters, strength and weakness parameters, etc. that are useful for fitting and controlling rehabilitation using the movement training apparatus 299.

Another tested A-TPAD embodiment and associated results of are presently described. This embodiment is also an active tethered pelvic assist device (A-TPAD) where external forces are applied on a hip belt, worn by a human, via actuated cables. Unlike body weight support systems used in gait rehabilitation, the A-TPAD applies a controlled external wrench on the human pelvis in selected directions and at any point during the gait cycle for a specified duration. This force challenges the subject. In therapeutic applications, the perturbation helps the patient develop competence to resist falls. During walking with the A-TPAD, the pelvic motion is monitored in real-time using a motion capture system. An online optimization scheme is used to compute the selected cable tension values to be applied. This paper successfully demonstrates control of the applied wrench using the A-TPAD during human walking.

In further tests, described below, a pilot study with ten healthy subjects was conducted using the A-TPAD. During the study, vertical downward forces were applied on the human pelvis during the complete gait cycle, equivalent to 10% of subject's body weight. Results show that subjects adapt in their gait patterns as a result of the externally applied forces and also show aftereffects once the forces are removed. In addition, subjects walk with higher forces transmitted through their legs both during training and once the external forces are removed during post-training. This has important consequences in terms of stance timing, gait symmetry, weight bearing and bone health of the legs.

A-TPAD is configured not to inhibit or force the natural degrees of freedom of the legs as typically done by robotic exoskeletons. The natural motion can be more complex than robotic exoskeleton DOFs such that they kinematically constrain natural movement.

As are embodiments of A-TPAD, a cable-driven system, using low mass cables and few rigid components, can offer advantages during gait rehabilitation. The A-TPAD does not constraint the human motion and does not add undesirable mass/inertia on the human. The design provides flexibility to achieve different cable configurations to apply external wrench on the human pelvis in selected directions and combinations. The A-TPAD controller may employ a real-time motion capture system and an online optimization scheme to keep positive cable tension during the human motion.

The A-TPAD may serve as a platform to externally applied forces and moments on the human pelvis during walking for research and treatment. The human nervous system is believed to be capable of predicting upcoming movement requirement based on an internal body representation. When external forces are applied, these requirements modify due to induced movement errors. The human nervous system may update the internal representation through experience to modify the motor commands. Such recalibration of existing motor commands can provide benefits for gait rehabilitation.

In a tested application, an A-TPAD was used to develop a weight-bearing effect during walking. A human experiment is conducted, where a force equivalent to 10% of subject's body weight (BW) was applied vertically downward on the pelvis while the subject walked on a treadmill. Subjects adapted their gait kinetics in response to the applied forces and walk with higher forces transmitted through their legs.

Figure 16A:
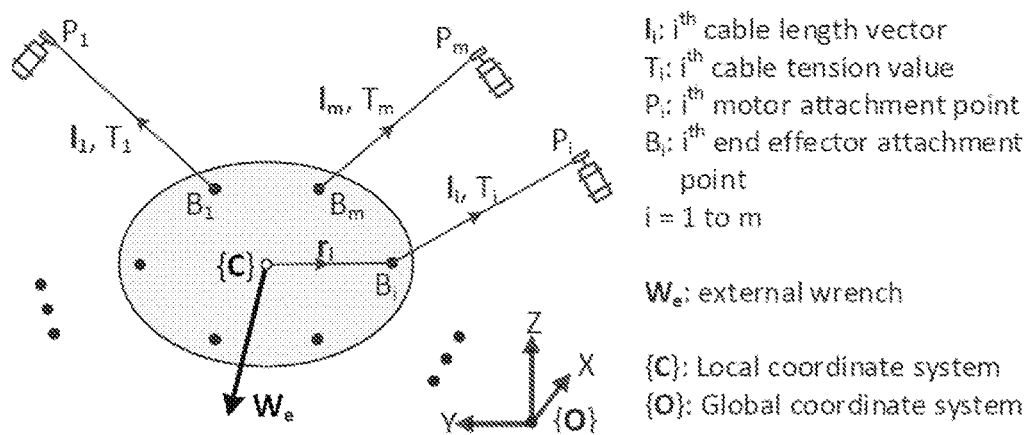
FIG. 16A shows how wrenches are generated using cable tension control, according to embodiments of the disclosed subject matter.

The present A-TPAD includes a cable-driven parallel system with m actuated cables connected to the human pelvis having n=6 degrees-of-freedom (DOFs), refer to FIGS. 9 and 16A and description above relating to FIG. 9. Each cable may be modeled as a pure force at the attachment point. These cables together exert a wrench on the pelvis. Therefore, if m×1 vector T represents the tension in the cables and n×1 vector $W_e$ the external wrench on the pelvis, these are related to each other as $$AT = W_e, \tag{18}$$

where A is a n×m structure matrix, which depends on the system geometry and can be computed knowing the coordinates of the cable attachment points. For a six DOFs system, when $W_e$ is computed at the point C, refer to FIG. 3, the matrix A is given by the following expression.

$$A = \begin{bmatrix} \cdots & l_i & \cdots \\ \cdots & r_i \times l_i & \cdots \end{bmatrix}_{6 \times m}, \tag{19}$$

where $l_i$ is the $i^{th}$ unit cable length vector oriented away from the connecting rigid body and $r_i$ is the vector from the point C to the $i^{th}$ cable attachment point on the rigid body.

It has been shown that for an n DOFs system, at least n+1 cables are required for generating a selected n×1 $W_e$ vector. This makes Eq. (1) under-determined. The general solution can be written in terms of the minimum norm solution ($\bar{T}$) and the null space of the structure matrix A, assuming A to be full rank.

$$T = \bar{T} + N(A)\lambda \tag{20}$$

$$\text{where } \bar{T} = A^T(AA^T)^{-1}W_e, \tag{21}$$

where N(A) is the null space of matrix A and λ is an arbitrary (m−n) vector.

For T±0, i.e., each element of T is positive, Eq. (3) defines a convex region in the space of tension values at a configuration of the system. Therefore, an optimization problem can be formulated to find the best solution of tensions within the feasible set. In the current work, a quadratic programming based optimization scheme with a lower and a upper bound on the cable tension values is implemented. (±stands for the componentwise inequality. For u, v two vectors in $R^n$, $u \pm v \Leftrightarrow u_i \geq v_i$, i=1, . . . , n.)

$$\min f$$

$$f = \frac{1}{2}(T-T_p)^T(T-T_p)$$

$$\text{s.t. } AT=W_e, \text{ and } T_{min} \circ T \circ T_{max} \quad (22)$$

where $T_p$ is a positive constant, which is added to the objective function to ensure non-zero cable tension values. $T_{min}$ and $T_{max}$ are the lower and upper bounds on the cable tension values.

TABLE 3

Cable attachment locations on the frame

|  | $P_1$ | $P_2$ | $P_3$ | $P_4$ |
|---|---|---|---|---|
| X (m) | 0.60 | 0.60 | −0.60 | −0.60 |
| Y (m) | 0.80 | −0.80 | 0.80 | −0.80 |
| Z (m) | −0.10 | −0.10 | −0.10 | −0.10 |

During an experiment, the wrench capability of the A-TPAD depends on the actuator limits as well as the pelvic position relative to the cable attachment locations on the frame. The feasible workspace is defined as the set of pelvic poses a subject can have during walking on a treadmill in which the A-TPAD can apply a specific external wrench using limited cable tensions. The goal of the current human experiment is to apply a force equivalent to 10% BW vertically downward on the pelvis during treadmill walking. A weight bearing configuration was chosen, as shown in the FIG. 9, where four cables connect the hip belt to the lower part of the frame. This configuration reduced the possibilities of cable interference with the hand motion during walking. A simulation in Matlab (Mathworks, Natick), using baseline pelvic trajectories from earlier studies, was done to check the feasible workspace and finalize the cable attachment locations on the frame. Cable attachment locations on the frame used during the experiment, $P_i$s, are given in Table 3, when the treadmill center is taken as the origin. With these locations, it was observed that the system can apply a 10% BW vertical downward force on the pelvis for a wide range of subject's height (5-6.4 ft) and weight (55-95 kg) such that $F_X$ and $F_Y$ lie within ±1% BW and the moment components at the pelvic center remain under 4 Nm.

Figure 16B:
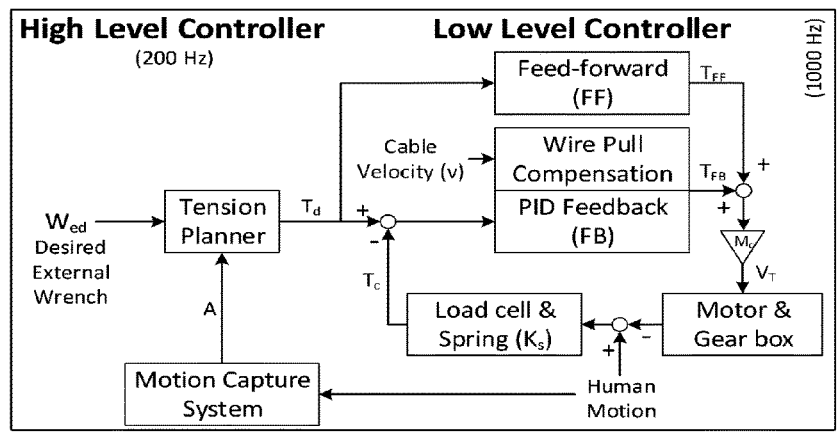
FIG. 16B shows the control architecture of the A-TPAD according to embodiments of the disclosed subject matter.

The A-TPAD applies a selected wrench on the pelvis during walking. This may be achieved in two steps: (i) selected cable tension calculation, and (ii) selected cable tension implementation. FIG. 16B shows the control architecture of the A-TPAD for the experiments of the present embodiment divided into two parts. The high level controller tracked the human motion and cable attachment locations and uses an online optimization scheme to calculate the selected cable tension values, $T_d$, necessary to apply selected external wrench, $W_{ed}$. The low level controller implements the $T_d$ values using a unit gain FF and PID based FB terms. A wire pull compensation is added to resolve the cable slackening problem and improve the controller performance.

The part of the controller that calculates the cable tension values was implemented at 200 Hz and referred to as the high level controller. A real-time motion capture system was used to track the retro-reflective markers placed at cable attachment locations and various human anatomical positions. These marker data are accessed on a host computer running a Vicon Nexus software, where three markers define a rigid body kinematically and a single marker defines a point in the global coordinate system. Using a .NET assembly reference to the Vicon data software development kit (SDK), cable attachment locations are sent to a remote Labview PXI system. The tension planner, as described in section 2, uses the cable attachment locations to calculate the structure matrix, A, which is then used to calculate the selected cable tension values, $T_d$, required to apply the selected wrench, $W_{ed}$. During the experiment, the values of $T_p$ in Eq. (5) were taken to be the cable tension values calculated in the previous step, to keep smoother cable tension profile. For those instances, when the optimization problem did not yield the solution or when the markers were occulted, tension values calculated in the previous step were used.

Figure 16C:
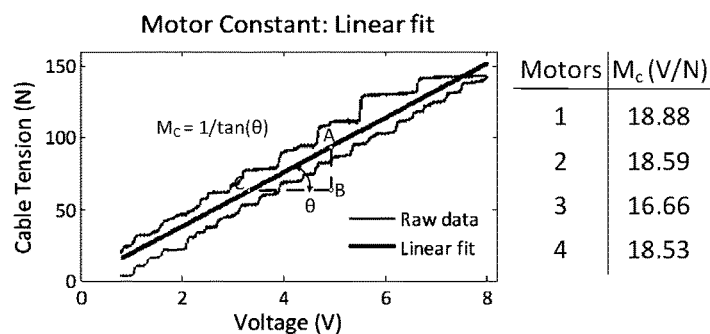
FIG. 16C shows data relating to a motor control algorithm according to embodiments of the disclosed subject matter.

The part of the controller that implements the selected cable tension is implemented at 1000 Hz and referred to as the low level controller. A force mode control scheme is used to follow the selected tension values. An open loop reference feed-forward (FF) term with a unit gain and a closed loop PID based feedback (FB) term are used, refer to FIG. 16B. The net commanded voltage to a motor, $V_T$, is given by the following expression.

$$V_T = M_c(T_{FB} + T_{FF}) \quad (23)$$

$$\text{where } T_{FB} = \left[K_p e + K_i \int e(\tau)d\tau + K_d \frac{dT_c(t)}{dt}\right],$$

$$T_{FF} = T_d \text{ and } e = T_d - T_c$$

where $T_{FB}$ and $T_{FF}$ are the outputs of the FB and FF terms, $T_d$ and $T_c$ are the selected and current cable tension values, and e is the tension error. $M_c$ is a positive constant for each motor, called motor constant, which relates the commanded voltage to the cable tension values linearly. FIG. 16C shows the calculation of $M_c$ for a motor. $K_p$, $K_i$ and $K_d$ are the gains for the proportional, integral and derivative terms respectively. The values of these gains depend on the used spring stiffness, $K_s$, and their values when $K_s$=2.5 N/mm were 3.5, 0.001 and 0.0004 respectively. To acquire the data of FIG. 16C, positive voltage was applied on a motor to pull a cable connected to a fixed rigid support at the other end. The collected cable tension and motor voltage data were linearly fitted to calculate the motor constants for each motor, $M_c$.

Figure 17A:
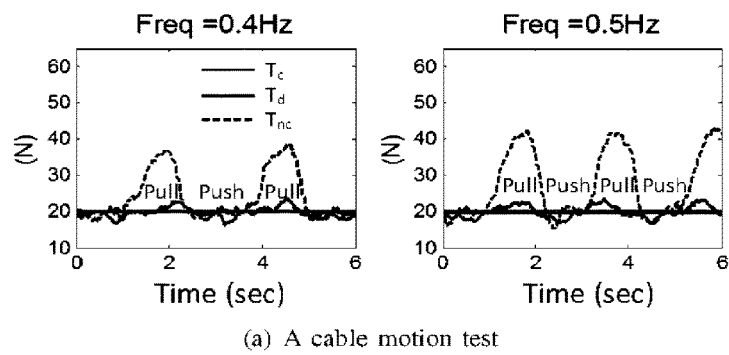
FIG. 17A shows results of tests of cable actuators according to embodiments of the disclosed subject matter.
Figure 17A:
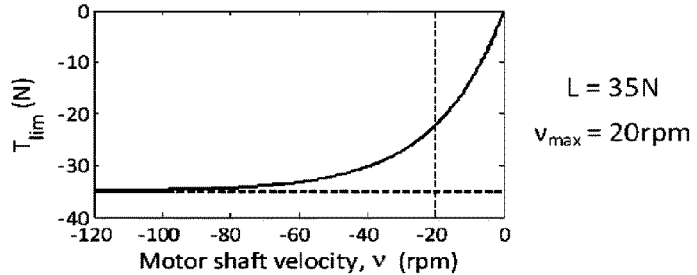

Since each cable in a cable-driven system is actuated unilaterally a force mode is used in the A-TPAD. A commanded motor voltage, $V_T$, can have both positive and negative values because the FB output's sign and magnitude depends on the tension error, e (See Eq. 23). Negative values of $V_T$ can cause cable slackening resulting in cables to come off the reel. A limit on the minimum output of the FB term can be placed to keep the $V_T$ values non-negative, for example $(T_{FB})_{min}=-T_{FF}$ is used in. However, such limits can potentially add the actuator dynamics to the subject, as shown by a simple test in FIG. 17A. Referring to FIG. 17A, part a, a cable was pulled and pushed by hand to almost 1 ft at 0.4 and 0.5 Hz frequencies, which were monitored using a metronome. The actual and selected ($T_d$=20 N) cable tension values are plotted, where $T_c$ and $T_{nc}$ are the cable tension values with and without the wire pull compensation term. In FIG. 17A, part b, $T_{lim}$ is zero when the subject is not moving and approaches −L exponentially as the cable velocity becomes more negative. In this test, a cable was pulled and pushed by hand to almost 1 ft at different frequencies, which were monitored using a metronome. The selected tension value, $T_d$, was 20 N and the applied cable tension values were recorded using a load cell, shown as $T_{nc}$. The $T_{nc}$ values increased during the cable pulling phase, where $V_T$ equals zero, which means that the actuator dynamics was very apparent to the subject. From this test, it was also observed that the cable velocity was positive during the cable pushing phase and negative during the cable pulling phase. Notably, the magnitude of the cable velocity increased with increase in the motion frequency. Therefore, a wire pull compensation, WPC, term was implemented in parallel to the FB term, which updates the minimum FB output limit for each motor as a function of the cable velocity, and is given by the following expression.

$$(T_{FB})_{min} = -T_{FF} + T_{lim} \quad (24)$$

$$T_{lim} = -L\left(1 - e^{\frac{-\|v(t)\|}{v_{max}}}\right)$$

where $T_{FF}$ is the FF term output, v(t) is the cable velocity, L and $v_{max}$ are two positive parameters. These parameters are tuned during a human walking test to achieve a responsive controller that does not result in cable slackening. The variations of $T_{lim}$ with v(t) are shown in FIG. 16C. $T_{lim}$ is zero when the subject is not moving and approaches −L exponentially as the cable velocity becomes more negative. In FIG. 16C, the effect of adding this term on the controller performance is shown by $T_c$. It was observed that the controller performance improved significantly during the cable pulling phase, which is almost similar to the cable pushing phase.

To test the system and evaluate its performance, an experiment was conducted using a rigid plate, referred to as the dummy pelvis. The dummy pelvis setup included two Delrin® plates attached together using a six axis force-torque sensor. Cables were attached to the upper plate to apply the selected external wrench. The setup included two 1 ft by 1 ft square Delrin® plates attached together with a six axis force-torque sensor (Mini45 from ATI Industrial Automation, North Carolina). Cables from the motors were attached to the upper plate. The force-torque sensor recorded the force-moment vector at the center of the upper plate with respect to the lower plate. Retro-reflective markers were placed on the upper plate to record the cable attachment points. Three markers were also placed on the lower plate to define a local coordinate frame, which was used to resolve the measured force-moment vector in the global coordinate system.

TABLE 4

| | Root mean square error | | | | | |
|---|---|---|---|---|---|---|
| RMSE | $F_x$ (N) | $F_y$ (N) | $F_z$ (N) | $M_x$ (Nm) | $M_y$ (Nm) | $M_z$ (Nm) |
| $W_s - W_c$ | 0.66 | 1.75 | 2.77 | 0.38 | 0.19 | 0.07 |
| $W_d - W_c$ | 0.54 | 1.35 | 3.14 | — | — | — |
| $W_d - W_s$ | 0.58 | 1.55 | 2.13 | — | — | — |

Four cables, in the configuration similar to the FIG. 9, were used to apply a three dimensional sinusoidal varying force on the upper plate while the moment components at the plate center were kept within a small range. The quadratic optimization in Eq. (22) was solved for the following parameters.

$$F_X = 1\sin(2\pi f\tau)N \quad (25)$$

$$F_Y = 4\sin(2\pi f\tau)N$$

$$= -45 + 6\sin(2\pi f\tau)N$$

$$|M_{X,Y,Z}| \leq 2Nm$$

$$10 \leq T \leq 60N$$

where τ is the time and f is the frequency (f=1.5 Hz during the experiment).

The force-moment values recorded by the force-torque sensor, $W_s$, were converted to the global coordinate system using the lower plate marker data. The applied force-moment vector, $W_c$, was also calculated using the actual cable tension values recorded by the load cells and the structure matrix, A, using Eq. (18). The selected force values, $W_d$, from Eq. (25) are also computed. Root mean square errors, RMSE, were calculated between the $W_s$, $W_c$ and $W_d$ values, refer to Table 4.

It was observed that the system was able to follow the selected force profile at the commanded frequency and the moment values remained within the selected limit of ±2 Nm in the three directions. The force values of $W_c$ and $W_s$ matched closely with RMSE under 1, 2 and 3 N in the X, Y and Z directions respectively. Similarly, the RMSE between the moment values was under 0.5 Nm in all the three directions. Ideally $W_c$ and $W_s$ values should have matched perfectly but the small compliance in the plate setup resulted in small displacement of the upper plate at the connecting points whenever the cable tension reversed its direction leading to the observed disparities.

The proposed weight bearing paradigm using the A-TPAD for the human experiment, as shown in the FIG. 9, involved the application of a 10% BW vertical downward force on the pelvis. In addition, the medial-lateral ($F_X$) and anterior-posterior ($F_Y$) force components were maintained within 1% BW, and the moment components resolved at the pelvic center were maintained within 4 Nm. The commanded wrench components and the tension limits to the controller are given by the following equations.

$$|F_{X,Y}| \leq 1\% \text{ BW}$$

$$F_z = -10\% \text{ BW}$$

$$|M_{X,Y,Z}| \leq 4 \text{ Nm}$$

$$5 \leq T \leq 60 \text{ N} \quad (26)$$

Ten healthy male subjects, all right handed, participated in the study and provided their written consent. The age range was 20-35 years (mean age: 27 yrs and SD: 3.7 yrs) and the mean weight was 72 kg (SD: 12.7 kg). The training protocol was approved by the Columbia University Internal Review Board and involved baseline, training and post training sessions, as shown in FIG. 17H. FIG. 17H: shows the experimental protocol for the human experiment included baseline, training and post training sessions. The numbers in the block indicate the data collection trial number for each session.

The subject was suited up with retro-reflective markers to record the human motion data. A fabric hip belt with cable attachment points was worn by the subject and a three axis accelerometer was mounted on the subject's pelvis. Force sensitive resistor (FSR) pressure pads with 440 N limit (Flexiforce® from Tekscan, Massachusetts) were mounted on the subject's shoe insoles to measure the foot pressure data.

During this period, each subject walked on a treadmill for four minutes at a constant speed of 3.8 kmph. Data collected during the last minute of this session was treated as the reference data and labeled as BL in this paper.

During this period, each subject walked for sixteen minutes at a fixed treadmill speed of 3.8 kmph, with all four cables attached to the hip belt to apply the selected external wrench on the pelvis. As the subject walked, the controller adjusted the tension values of each cable to continue applying the selected external wrench. Data were recorded six times for one minute duration at the start, $3^{rd}$, $6^{th}$, $9^{th}$, $12^{th}$ and $15^{th}$ min. These data collection instances were referred to as T1, T2, T3, T4, T5 and T6 as shown in the FIG. 17G by the numbers.

During this period, each subject walked for another ten minutes at a fixed treadmill speed of 3.8 kmph immediately after removing the cables. Data were recorded four times for one minute duration at the start, $3^{rd}$, $6^{th}$ and $9^{th}$ min. These data collection instances were referred to as PT1, PT2, PT3 and PT4.

Before the baseline session, each subject was asked to stand still for a few seconds to record a static data set.

During the experiment, each subject's kinematics, foot pressure, pelvic acceleration and applied wrench data were recorded for the analysis. The time histories of all gait parameters were normalized in time to 100% of the gait cycle, where a gait cycle was defined from a right heel strike event (RHS) to subsequent right heel strike. The farthest anterior position of the heel marker with respect to the sacrum marker was used to define the heel strike (HS) event and the farthest posterior position of the toe marker with respect to the sacrum marker was used to define the toe-off (TO) event. These events were used to estimate the durations of double support (DS) phases, single support (SS) phases, stride time and stance time during a gait cycle. Gait symmetry between the two legs was analyzed by calculating the stance-swing ratio (SSR), the stance period ratio (SPR) and the double support ratio (DSR). It has been identified in that these ratios are critical in governing the symmetry of gait. Gait cadence was defined as the number of steps per minute. The centroid of three pelvic anatomical markers was calculated to define the position of the pelvic center. Lower limb sagittal plane joint angles were estimated from the human segment marker data. The foot pressure data of each leg were normalized by the maximum and minimum pressure values of the baseline trial. It is important to note that the pressure sensors cover only a part of the subject's foot, therefore the pressure values were not related to the subjects' weight. Since, it was impossible to place these sensors at the same spot for all subjects, the pressure data were not statistically analyzed. However, increase in the pressure values during the experiment could only be due to higher ground reaction forces.

To study the subjects' performance and their responses to the applied external wrench, gait parameters data from the last ten gait cycles for trials BL, T1, T6, PT1 and PT4 were used. The data were checked against the sphericity violation using the Mauchly's test and the Huynd-Feldt correction was applied when the data violated the condition. Repeated measure analysis of variance (ANOVA) was performed to determine the statistically significance (defined as p<0.05). The Bonferroni-Holm significant difference test was performed when a statistical significance was identified. The chosen combinations for statistical difference comparison were BL-T1, BL-T6, BL-PT1, BL-PT4 and T6-PT1. Values plotted in the following section are the means±standard errors.

Figure 17B:
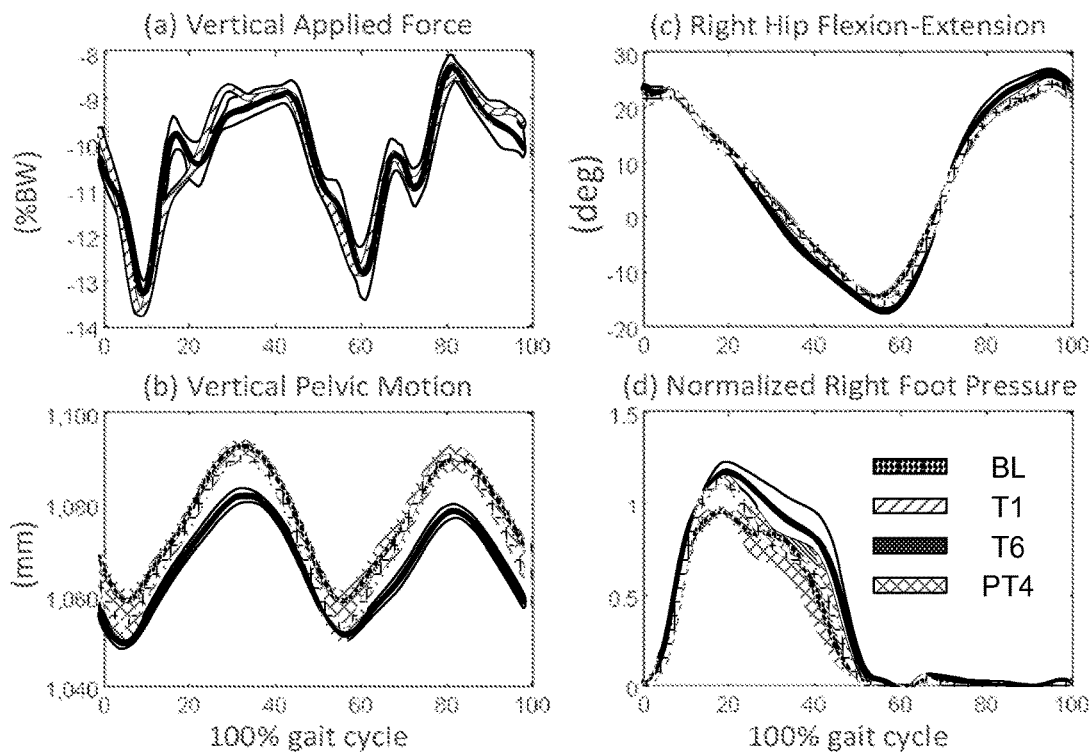
FIG. 17B shows gait parameters for a representative subject during different experimental sessions plotted over a gait cycle with the solid line representing the mean value during a trial and the shaded area plots the trial variation for that gait parameter, a gait cycle being defined from RHS to subsequent RHS.

All subjects successfully completed all sessions of the experiment. During the experiment, very few instances were recorded with occluded markers or the optimization scheme not being able to find the feasible cable tension values. FIG. 17B shows gait parameters for a representative subject during different experimental sessions plotted over a gait cycle. Uniform lines represent a mean value during a trial and the variable areas indicate the trial variation for that a parameter. A gait cycle is defined from RHS to subsequent RHS.

Figure 17C:
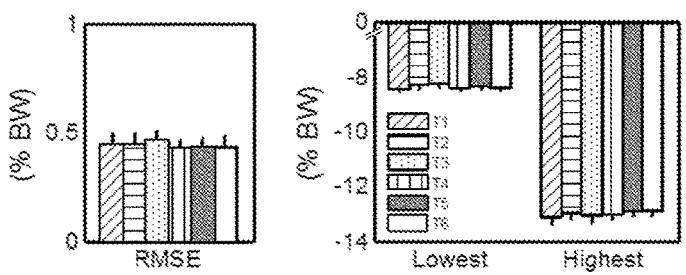
FIG. 17C to 17F shows parameters relating to tests of an A-TPAD embodiment.
Figure 17D:
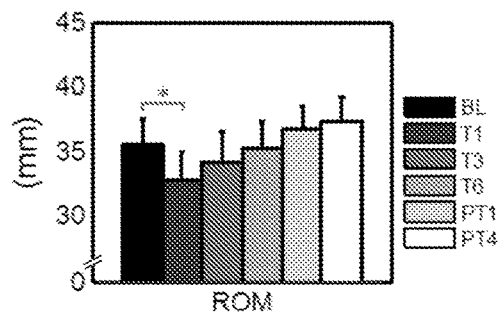

FIG. 17B-upper left shows the vertical component of the applied force-moment vector, $F_Z$, on the pelvis of a representative subject during the training session. Periodic variations in the $F_Z$ values almost at twice the gait frequency were observed over the gait cycle. The highest $F_Z$ magnitudes, lowest $F_Z$ magnitudes and root mean square error (RMSE) between the selected and applied $F_Z$ values for the group were tested for the statistical significance, refer to FIG. 17C. Repeated measure ANOVA did not report any significant change in the values of these parameters between trials T1, T3 and T6 (RMSE: p=0.6, Highest: p=0.07 and Lowest: p=0.33). The $F_Z$ values during a gait cycle were between −8.3 and −12.9% BW, and the RMSE values were below 0.5% BW during the training trials, T1 to T6, for all subjects. In addition, the rest of the force and moment components of the applied wrench at the pelvic center remained within the selected levels of 1% BW and 4 Nm respectively during the training session. FIG. 17C shows body weight-normalized vertical force, $F_Z$, on the subject's pelvis for the group. RMSE is the root mean square error between the applied and the selected force values. Lowest is the minimum $F_Z$ magnitude and highest is the maximum $F_Z$ magnitude applied during a gait cycle. No significant changes were observed in these values.

FIG. 17B-lower left shows the vertical motion of the pelvic center, $P_Z$, of a representative subject during different experimental trials. Lower $P_Z$ values over a gait cycle compared to trials BL and PT4 were observed during the trial T6. A significant effect of the training with the applied force-moment vector was observed in the pelvic range of motion, ROM, values in the vertical direction (p≤0.05), refer to FIG. 17E. The post-hoc pairwise analysis reported that the vertical pelvic ROM values were significantly lower than the baseline values during the trial T1. With the progression of training session, the ROM values increased to reach the baseline level. During the post-training trials, these values were higher than the baseline level, though these differences were not statistically significant.

FIG. 17B-upper right shows the hip flexion-extension values of a representative subject during different experimental trials. Increase in the hip flexion and extension values were observed during the trial T6. The statistical analysis on the hip flexion-extension ROM values reported significant change during the experiment (p≤0.05), refer to FIG. 17F. Significant increases in the hip ROM values were reported during the trials T1 and T6 over the baseline values. The average hip ROM values during the post-training trials were not significantly different from the baseline values. Significant changes were also observed in the knee maximum flexion values and knee flexion-extension ROM values (p≤0.05). These values increased as the training session progressed such that a significant difference was reported between the trials BL and T6. These values remained higher during the post-training trials as confirmed by the pairwise comparison between PT1-BL and PT4-BL.

TABLE 5

Changes in the gait parameter values during the experiment.

|  | (T1-BL)/BL | (T6-BL)/BL | (PT1-BL)/BL | (PT4-BL)/BL | (PT1-T6)/T6 | p-value |
|---|---|---|---|---|---|---|
| Right Stance Duration | 0.6% | 1.27% * | 0.84% | 0.36% | −0.43% | <0.05 |
| Right Stride Time | −2.66% * | −0.36% | 0.23% | 2.12% | 0.58% | <0.05 |
| Cadence | 3.41% * | 0.47% | −0.28% | −1.43% | −0.75% | <0.05 |
| Right SS Duration | −1.2% | −2.53% * | −1.67% | −0.72% | 0.88% | <0.05 |

* represent the pairwise comparisons reaching significance.

FIG. 17B-lower right plots the right heel foot pressure values of a representative subject during different experimental trials. Higher pressure values were observed during the trials T6 and PT4 compared to the trial BL. The magnitude of the vertical pelvic acceleration values recorded by the accelerometer minus the acceleration due to gravity was positive during the double support, DS, phases and negative during the single support, SS, phases of a gait cycle. A significant change was reported in the negative vertical acceleration peak values (p≤0.05), refer to FIG. 17F. The pairwise analysis reported significantly higher negative acceleration peak magnitudes during the trials T1 and T6 compared to the baseline values. The magnitude of the negative acceleration peak also remained significantly higher during the trial PT1 compared to BL. The changes in the positive acceleration peak values were not statistically significant (p=0.58), refer to FIG. 17F.

Figure 17E:
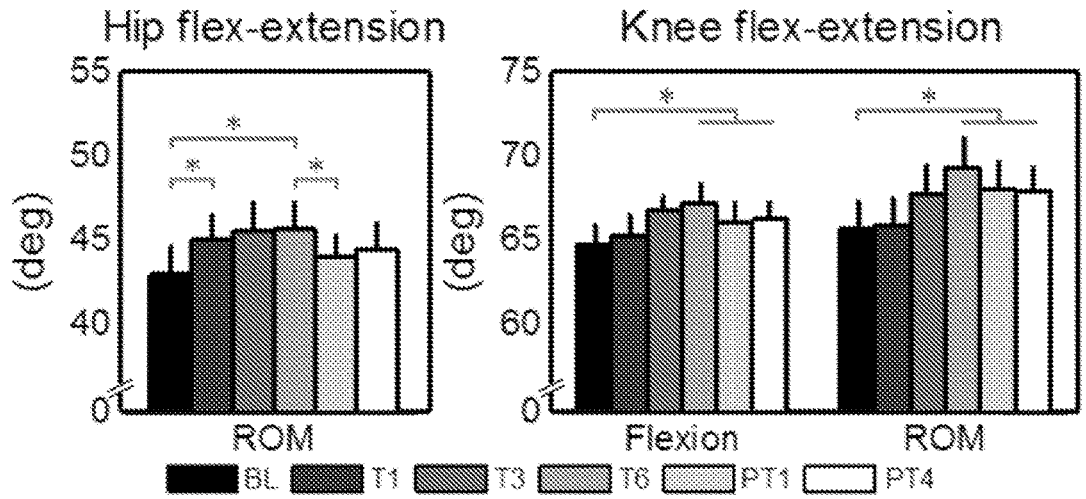

FIG. 17E shows hip and knee flexion-extension ROM and maximum knee flexion values for the group. Average hip ROM values changed significantly between following pairs BL-T1, BL-T6 and T6-PT1. Average knee flexion values and knee flexion-extension ROM values reported following significant pairwise comparisons BL-T6, BL-PT1 and BL-PT4. FIG. 17E shows pelvic range of motion, ROM, in the vertical direction during a gait cycle for the group. Significant changes were reported between the average ROM values during BL and T1.

No significant changes were reported in the DSR, SPR and SSR values during the experiment (p=0.7, p=0.08 & p=0.09 respectively), implying that the gait symmetry was retained. Significant changes were reported in the stride time and the gait cadence values (p≤0.05). Refer to Table. 5. The stride time values reduced and the cadence values increased significantly during the trial T1 as compared to the baseline values. The values of these parameters returned back to the baseline level with the progression of the training session. During the post-training trials, aftereffects were observed in their values, though pairwise comparison did not report significance. The statistical analysis also reported significant change in the stance phase and SS phase duration values (p≤0.05), refer to Table. 5. Subjects spent larger part of the gait cycle in the stance phase during the training session such that significant difference was reported between the trials BL and T6. Stance phase duration values were also reported to be higher during the post-training session compared to the baseline values. The SS phase duration values decreased significantly during the trial T6 as compared to the baseline values.

Figure 17F:
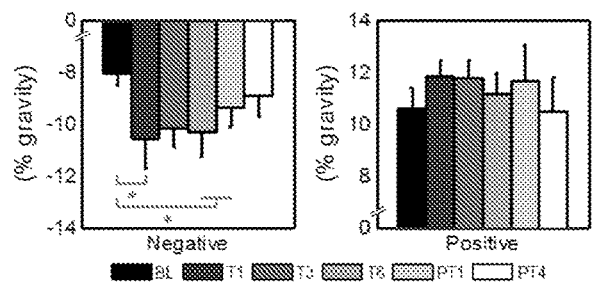

FIG. 17F shows pelvic acceleration peak values in the vertical direction minus the acceleration due to gravity over different sessions of the experiment. The acceleration values were negative during the SS phases and positive during the DS phases. Significant changes were reported in the negative acceleration peak values between following pairs BL-T1, BL-T6 and BL-PT1.

The experiments confirm that A-TPAD can apply a controlled external wrench on the human pelvis in any direction and at any point during the gait cycle for a selected duration. Such a capability is achieved by using a real-time motion capture system, which tracks the various human anatomical and cable attachment locations. These data sets are made available to an online optimization scheme for the calculation of cable tension, required to apply selected wrench on the pelvis. A force mode control using a feed forward and a PID based feedback terms is used to implement the selected cable tension. A wire pull compensation term based on the cable velocity is also added to improve the controller performance and prevent cable slackening during experiment. This use of cable robot is unlike existing use of cable robots in gait rehabilitation, where cables are used to support subject's body weight during walking. In A-TPAD, each motor is mounted on an independent unit and cable drives such as pulleys are used for cable routing. This architecture provides the capability of achieving different cable configurations. Further, the number of motors can also be changed based on the selected wrench requirement. In this work, the system's performance was demonstrated in applying a sinusoidal varying force vector at 1.5 Hz on a rigid plate. The results showed successful implementation of the A-TPAD control strategy.

A-TPAD was used in experiments to implement a weight bearing paradigm for walking. Healthy subjects participated. Four cables were used to apply a selected wrench on the subjects' pelvis. The system applied the vertical force over the full gait cycle and a 0.5% BW RMSE was observed. During the human experiment, subjects' immediate response to the applied forces was to reduce the pelvic vertical ROM significantly. In addition, subjects increased the gait cadence by reducing the stride time. With the progression of training with the applied forces, subjects adapted their gait pattern such that these parameters returned back to the baseline level. Notably, gradual increase in the stance phase duration values and knee flexion-extension values was reported during the training session. During the post-training session, negative aftereffects in the pelvic vertical ROM, gait cadence and stride time values were reported. In addition, higher knee flexion-extension and stance phase duration values were retained when forces were removed. The changes in these gait parameters can be categorized as: (i) Parameters that changed immediately with the force application, subjects were able to bring these parameters back to the baseline level after some experience with the applied force such that the removal of force resulted in the opposite change in these parameters' values, (ii) Parameters that changed gradually during the training session and subjects retained these changed values when the forces were removed. These results show that healthy subjects adapted gait kinematics in response to the applied downward force. Similar changes in gait parameters have been reported in various motor adaptation studies in literature, when movement errors were added during human walking.

In the current experiment, gait symmetry was retained. In addition, the pelvic vertical acceleration values reported significant increase during the training session. Particularly, subjects generated higher pelvic acceleration during the single support phase of the gait cycle. This was because of the external downward force on the subjects' pelvis, which required extra push-off effort by the subjects. Subjects retained these large magnitudes of pelvic acceleration when the external forces were removed. The increase in the pelvic acceleration and increase in the stance phase duration values further imply that subjects applied higher ground reaction forces during the experiment. These results show that healthy subjects adapted gait kinetics in response to the applied downward force. These results have important consequences in terms of improving weight bearing capability in patients. Such training paradigms are further useful in improving bone health of legs. Patient groups, such as stroke survivors, CP kids and amputees, shy away from supporting their weight on the weak limbs. These patients generally develop compensatory strategies which lead to gait asymmetry, poor balance, hip hiking etc. The weight bearing paradigm using A-TPAD provides a novel way to approach these problems.

A-TPAD can apply controlled external wrench on the human pelvis. A control strategy was successfully tested on a dummy pelvis setup. Human walking further showed A-TPAD capability in maintaining the cables in tension during the different phases of the gait cycle. Unlike any rigid link gait rehabilitation robotic device, the A-TPAD adds minimal mass/inertia on the subject and avoids undesirable mobility constraints. A weight bearing experimental paradigm during walking was tested on healthy subjects using A-TPAD. Subjects adapted their gait kinematics and kinetics in response to the applied force vector. The force adaptation resulted in aftereffects when the external force vector was removed. In summary, A-TPAD can be used to develop novel gait rehabilitation paradigms for various patient groups.

The following describes tests, evaluation, control aspects for an A-TPAD embodiment for treatment, research, and diagnosis of locomotor adaptation in healthy adults when an asymmetric force vector is applied on the pelvis directed along the right leg. A cable-driven A-TPAD is used to apply an external force on the pelvis specific to a subject's gait pattern. The force vector is intended to provide external weight bearing during walking and modify the duration of limb supports. The motivation is to use this paradigm to improve weight bearing and stance phase symmetry in individuals with hemiparesis. An experiment with ten healthy subjects was conducted. The results show significant changes in the gait kinematics and kinetics while the healthy subjects developed temporal and spatial asymmetry in gait pattern in response to the applied force vector. This was followed by aftereffects once the applied force vector was removed. The adaptation to the applied force resulted in asymmetry in stance phase timing and lower limb muscle activity.

Walking is a state of continuous imbalance where each step is taken to regain the balance. It requires a complex control strategy to achieve sufficient foot clearance in the swing phase to prevent stumbling and sufficient weight bearing in the stance phase to preposition the swinging leg for the weight acceptance. A continuous gait is therefore a result of successful inter-limb coordination and cyclic activation of leg muscles. In healthy individuals, the gait pattern is characterized by repetitive movements of the lower limbs, which is smooth, regular and has spatio-temporal symmetry. On even terrains, these lower limbs movements generate symmetrical ground reaction force (GRF) distribution.

Neural impairments, such as stroke, cerebral palsy (CP) or spinal cord injury (SCI) damage motor cells and center nervous system (CNS) pathways in an individual. These damages limit one's ability to voluntarily contract muscles to normal amplitudes. Muscle spasticity and inappropriately timed muscle activity have also been reported in individuals with these impairments. These abnormalities therefore affect one's ability to walk. For example, individuals with hemiparesis demonstrate decreased hip and knee flexion during the swing phase, and reduced weight bearing with shorter stance time on the affected side. This leads to slow walking speed and asymmetric gait. Asymmetric gait patterns are further associated with higher energetics, increased risk of falling and serious injuries that limit patients' independence. Therefore, improving functional walking is a major goal in a gait rehabilitation program.

The cyclic activations of the lower limb muscles during walking generate torques at the joints that cause the movement of the limbs. In general, these torques are exerted in reaction to the external forces on the individual, such as gravity and ground reaction force (GRF). Therefore, in the gait rehabilitation community, methods have been developed to reduce the amount of joint torques required during walking. One such widely adopted strategy involves treadmill walking with patient's weight partly supported by a body-weight support system. In recent years, robotic exoskeletons have also been developed to provide assistance to the lower limb joints while walking. These devices can be programmed to test novel motor adaptation paradigms that allow active patient participation in the learning process. For example, in an assist-as-needed paradigm was implemented using an Active Leg Exoskeleton (ALEX), where the amount of external assistance was based on how closely a subject followed a target foot trajectory. Improvements in the subject's gait performance were reported as a result of this training.

Human nervous system is capable of anticipating upcoming movement requirements and accordingly modifying the motor commands. Another gait rehabilitation strategy is to develop interventions that modify the walking conditions to induce movement errors. These interventions drive the human CNS to make corrections to minimize the induced errors by modifying the motor commands. Such recalibrations of established motor commands during walking hold great potential in the rehabilitation process. For example, in, an error augmentation paradigm was implemented using a split-belt treadmill to further increase the gait asymmetry of stroke patients'. Improvements in the gait symmetry were reported as a result of the applied intervention. Similarly, in unilateral resistance was applied on stroke patients' lower limb by attaching weights during the swing phase. It was reported that mild to moderate hemiparetic stroke patients were able to achieve improved gait symmetry temporarily post training.

In most of these gait rehabilitation interventions, the primary goal was to correct either the swing phase gait measures, such as the hip and knee flexion, or the spatio-temporal gait measures, such as the step length symmetry. Very few studies, mostly during standing tasks, have targeted the weight bearing capability. During walking, the inability to bear weight during the stance phase affects the overall gait performance. Notably, it has been reported recently that the use of body-weight support system to partly reduce the patient's weight during training does not generalize to overground walking post-training and this method does not yield superior results when compared to the home-based physical therapy. In the current work, the locomotor adaptation was studied in healthy individuals when an asymmetric external force vector is applied on the pelvis directed along one of the legs. The force vector has a constant magnitude, equivalent to 10% of subject's body weight (BW), and is directed along a moving vector parallel to the right leg (a vector from the right iliac crest, RILIAC, to the right ankle, RANK). The vertical component of the applied force on the pelvis acts downward and provides external vertical load during walking.

In patients with neural impairments, the inability to generate sufficient lower limb muscle power during the stance phase also limits the ability to control the center of mass (COM) over the affected limb. Further, as walking is a state of continuous imbalance, it is the body's balance that controls the duration of limb supports during walking. For example, individuals with hemiparesis demonstrate longer swing phase and shorter stance phase on the affected side. In the current work, the external force was applied on the pelvis that changes its direction with the right leg motion during walking. As a result, a forward pull is applied on the pelvis when the RANK is anterior to RILIAC, while a backward pull is applied when the RANK is posterior to RILIAC. Thus, the anterior-posterior component of the applied force on the pelvis alters the body's balance during walking and creates the need to modify the lower limb support periods.

In the current work, a novel cable-driven pelvic robot, referred to Active Tethered Pelvic Assist Device (A-TPAD), is used to apply a selected external wrench (combined force and moment) on the pelvis. An experiment with ten healthy subjects was conducted, where the asymmetric force vector was applied on the subjects' pelvis while they were walking at a constant speed. It was hypothesized that the applied force vector will induce asymmetry in the gait pattern of healthy individuals. Further, it was expected that the subjects will adapt their gait kinematics and kinetics as a result of the applied force to show longer right stance phase and higher muscle activation in the right leg.

The cable robot A-TPAD and the control strategy are briefly described. The selected external force applied on the pelvis is also described in the same section, followed by the experimental protocol and data processing sub-sections. The results of the human experiment are reported and the experimental results and present the conclusions drawn from this work.

FIG. 9 and attending discussion describe the different components of the A-TPAD. Each cable in the A-TPAD embodiment was modeled as a pure force at the cable attachment point. All cables together exert an external wrench on the pelvis. If m×1 vector T represents the tension in the cables and n×1 vector $W_e$ the external wrench on the pelvis, these are related to each other as $$AT = W_e, \quad (27)$$

where A is a n×m structure matrix, which depends on the system geometry and can be computed knowing the coordinates of the cable attachment points on the brace and the frame.

Referring to FIG. 13 (part c) A vector parallel to the right leg, $\vec{u}$, is defined from the right iliac crest (RILIAC) anatomical position on the pelvis to the right ankle (RANK). (b) The sketch shows the selected trend of the anterior-posterior and vertical force components over a gait cycle. Gait events for both legs are identified, where HS: heel strike and TO: toe off. The initial and final single support (SS) and double support (DS) periods are also defined. θ defines the right limb angle. (c) Reference baseline pelvic and foot trajectories of three healthy subjects from earlier works are used to calculate the force distribution using Eq. 4.

For an n DOFs system, at least n+1 cables are required for generating a selected n×1 $W_e$ vector. This makes Eq. (27) under-determined. The general solution can be written in terms of the minimum norm solution and the null space of the structure matrix A, assuming A to be full rank.

$$T = A^T(AA^T)^{-1}W_e + N(A)\lambda \quad (28)$$

N(A) is the null space of matrix A and λ, is an arbitrary (m−n) vector.

For T±0, i.e., each element of T is positive, Eq. (28) defines a convex region in the space of tension values at a configuration of the system. Therefore, an optimization problem can be formulated to find the best solution of tensions within the feasible set. In the current work, a quadratic programming based optimization scheme with a lower and an upper bound on the cable tension values is implemented.

$$\min[½(T-T_p)^T(T-T_p)]$$

$$\text{s.t. } AT=W_e, \text{ and } T_{min} \circ T \circ T_{max} \quad (29)$$

where $T_p$ is a positive constant, which is added to the objective function to ensure non-zero cable tension values. $T_{min}$ and $T_{max}$ are the lower and upper bounds on the cable tension values.

A cable configuration, as shown in the FIG. 9, where four cables connect the hip belt to the lower part of the frame was used for this work. This configuration reduces the possibility of cable interference with the hand motion during walking.

A force vector was applied on the pelvis that follows the right leg motion during walking. Therefore, a vector from the right iliac crest (RILIAC) anatomical position on the pelvis to the right ankle (RANK) is selected, $\vec{u}$=RANK−RILIAC. The selected external wrench is expressed as, $$\vec{F}_d = \|F\|\hat{u} \quad (30)$$

$$|M_{X,Y,Z}| \circ 6Nm$$

$$5 \circ T \circ 60N$$

where û denotes the unit vector, refer to FIG. 13 (part a). The net magnitude of the selected force is constant ($\|F\|$=10% BW) and the force components in the medial-lateral (X), anterior-posterior (Y) and vertical (Z) directions depend on the RANK position with respect to RILIAC. External moments resolved at the pelvic center are kept under ±6 Nm, where the pelvic center is calculated as the centroid of the three pelvic anatomical markers.

FIG. 13 (part a) shows a stick diagram of the selected force variation in the sagittal plane during a gait cycle. Reference baseline pelvic and foot trajectories of three healthy subjects from earlier works are used here to calculate the force distribution using Eq. 30, which is shown in FIG. 13 (part b).

For healthy individuals, the foot movements in the medial-lateral direction are typically small over a gait cycle. The $F_X$ values calculated from the reference data show only a 1% BW variation, refer to FIG. 13 (part b). A negative $F_X$ value implies a force on the pelvis directed inwards to the treadmill.

The $F_Y$ values over a gait cycle are either positive or negative depending on whether RANK is anterior or posterior to RILIAC at that instance, refer to FIG. 13 (part c). A positive $F_Y$ value implies a forward pull on the pelvis. The $F_Y$ values calculated using the reference data have a maximum at the right heel strike (RHS: 1 and 100% of the gait cycle) and minimum at the right toe-off (RTO: around 63% of the gait cycle). The $F_Y$ values vary from 4% BW to –4% BW during a gait cycle and the rate of change is higher during the right swing phase compare to the right stance phase, refer to FIG. 13 (part b). Thus, in the current experiment a significant change was expected in the pelvic anterior-posterior movement during a gait cycle. In addition, it is expected that subjects will adapt their limb support periods as a result.

The $F_Z$ component is directed downward over the complete gait cycle, refer to FIG. 13 (part a). The $F_Z$ component has maximum peaks of almost 10% BW twice during a gait cycle, around each leg's mid swing phase (single support phase). The lowest values of $F_Z$ are at RHS and RTO, refer to FIG. 13 (part b). Even though the variation in the $F_Z$ values during a gait cycle is under 1% BW, the rate of change during the right swing phase is quite large compared to the right stance phase. In the current experiment, the subjects will experience a downward force throughout the training session and will adapt their gait kinetics as a result.

The reference baseline data of healthy subjects show that the selected force vector is mainly distributed in the sagittal plane and therefore the selection of $\vec{u}$ to decide the direction of selected force is reasonable.

The A-TPAD applies a selected external wrench on the pelvis during walking. Refer to Eq. 30. This is achieved in two steps: (i) selected cable tension calculation, and (ii) selected cable tension implementation. The controller architecture is shown in FIG. 16B.

The high level controller is implemented at 200 Hz. A real-time motion capture system (ten Bonita-10 series cameras from Vicon, Denver) is used to track the retro-reflective markers placed at cable attachment locations and various human anatomical positions. These marker data are accessed on a host computer running a Vicon Nexus software, where three markers define a rigid body kinematically and a single marker defines a point in the global coordinate system. Using a .NET assembly reference to the Vicon data software development kit (SDK), selective marker locations are sent to a remote Labview PXI system (National Instrument, Austin). The pelvis and foot markers are used to calculate vector $\vec{u}$ and the $\vec{F}_d$ values using Eq. 30. The tension planner, as described herein, uses the cable attachment locations to calculate the structure matrix, A, which is then used to calculate the selected cable tension values, $T_d$, required to apply the selected wrench, $W_{ed}$. During the experiment, the values of $T_p$ in Eq. 29 were taken to be the cable tension values calculated in the previous step, to keep smoother cable tension profile. For those instances, when the optimization problem did not yield the solution or when the markers got occluded, tension values calculated in the previous step were used.

FIG. 16B shows the controller: The control architecture, as before, is divided into two parts. The high level controller tracks the human motion and cable attachment locations. It uses an online optimization scheme to calculate the selected cable tension values, $T_d$, necessary to apply selected external wrench, $W_{ed}$. The low level controller implements the $T_d$ values using a unit gain feed-forward (FF) and PID based feedback (FB) terms. A wire pull compensation is added to resolve the cable slackening and improve the controller performance.

The low level controller part is implemented at 1000 Hz. An open loop reference feed-forward (FF) term with a unit gain and a closed loop PID based feedback (FB) term are used, refer to FIG. 16B. The net commanded voltage to a motor, $V_T$, is given by the following expression.

$$V_T = M_c(T_{FB} \pm T_{FF}) \qquad (31)$$

where $T_{FB}$ and $T_{FF}$ are the outputs of the FB and FF terms. $M_c$ is a positive constant for each motor, called motor constant, which relates the commanded voltage to the cable tension values linearly.

Each cable in a cable-driven system can only be actuated unilaterally. The sign and magnitude of FB output depends on the tension error, $T_d-T_c$, and therefore the commanded motor voltage, $V_T$, can have both positive and negative values, refer to Eq. 31 and FIG. 13. A negative value of $V_T$ rotates the cable reel to unwrap the cable. During the experiment, this cable slackening can result in cable coming off the reel if the subject is not moving or if the cable unwraps at a faster rate. Therefore, cable velocity as a measure of subject's motion is used and a wire pull compensation term is added in parallel to the FB term. This term updates the minimum FB output limit for each motor as a function of the cable velocity, and is given by the following expression.

$$(T_{FB})_{min} = -T_{FF} - L\left(1 - e^{\frac{-\|v(t)\|}{v_{max}}}\right) \qquad (32)$$

where $T_{FF}$ is the FF term output, $v(t)$ is the cable velocity, L and $v_{max}$ are two positive parameters. These parameters are tuned during a human walking test to achieve a responsive controller that does not result in cable slackening. The second term on the left side is zero when the subject is not moving and approaches –L exponentially as the cable velocity becomes more negative.

Figure 17G:
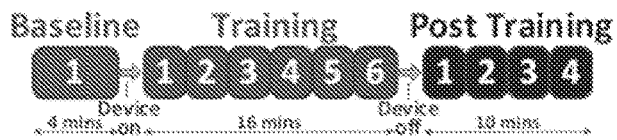
FIG. 17G shows a test protocols for tests of cable-actuated devices according to embodiments of the disclosed subject matter.

FIG. 17G shows an experimental protocol for the human experiment included baseline, training and post training sessions. The numbers in the block indicate the data collection trial number for a session. A catch trial was added in between the training trials T3 and T4.

Ten healthy male subjects, all right dominant, participated in the study and provided their written consent. The age range was 20-35 years (mean age: 26.6 yrs and SD: 3.8 yrs) and the mean weight was 71.5 kg (SD: 10.4 kg). One subject's data set was lost partly, so data of nine subjects were used for the group analysis.

The subject was suited up with retro-reflective markers to record the human motion data. The marker set was similar to the one used in. Surface EMG activity from the lower limb muscles were measured bilaterally, namely Gastrocnemius Medialis (MG), Soleus (SOL), Tibialis Anterior (TA), Vastus Lateralis (VL), Rectus Femoris (RF) and Biceps Femoris (BF) of each leg. Each electrode site was shaved and cleaned with alcohol. Surface electrodes with inter-electrode distance of 20 mm were placed on the muscles as per SENIAM guidelines. Electrodes were kept in place during the complete experiment. Single-differential signals were high-pass filtered with a first order analog filter (cut off frequency equal to 10 Hz), digitalized and received by a wireless desktop unit (DTS Desktop Receiver, Noraxon Inc., Arizona). This unit was connected to the Vicon motion capture system. A fabric hip belt with cable attachment points was also worn by the subject.

Figure 18A:
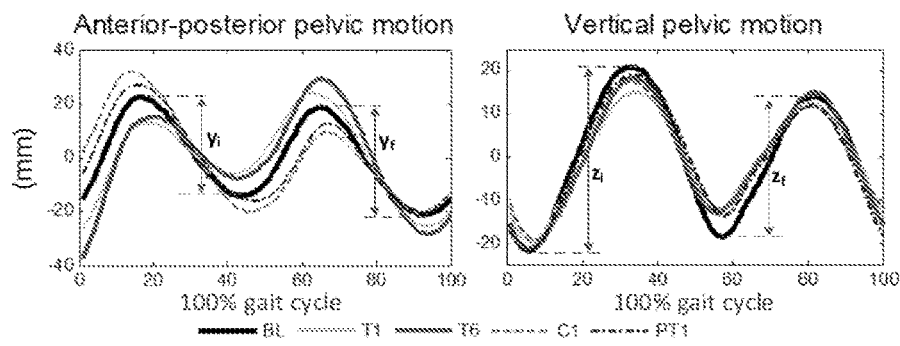
FIG. 18A, part a shows pelvic center anterior-posterior and vertical displacements during training trials for a representative subject and part b shows anterior-posterior and vertical pelvic motion asymmetric measures for the group during different trials of the experiment.
Figure 18A:
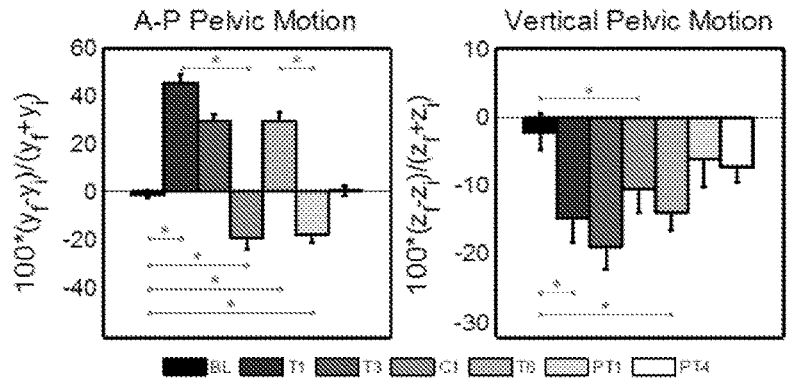

During this period, each subject walked on a treadmill for four minutes at a constant speed of 3.8 kmph. Data collected during the last minute of this session were treated as the reference data and labeled as BL for baseline. During this period, each subject walked for sixteen minutes at a fixed treadmill speed of 3.8 kmph, with all four cables attached to the hip brace to apply the selected external wrench on the pelvis. As the subject walked, the controller adjusted the tension values of each cable to continue applying the selected external wrench. Data were recorded six times for one minute duration at start, $3^{rd}$, $6^{th}$, $9^{th}$, $12^{th}$ and $15^{th}$ min. These data collection instances were referred to as T1, T2, T3, T4, T5 and T6 as shown in FIG. 18A by the numbers. To evaluate subjects' adaptation to the applied force vector, a catch trial was added at the middle of the training session (in between trials T3 and T4). During this trial, the A-TPAD was commanded not to apply the selected force on the pelvis but to maintain only a minimum tension in each cable to prevent cable slackening. Data collected during this trial were labeled as C1, as shown in FIG. 18A.

During this period, each subject walked for another ten minutes at a fixed treadmill speed of 3.8 kmph immediately after removing the cables. Data were recorded four times for one minute duration at start, $3^{rd}$, $6^{th}$ and $9^{th}$ min. These data collection instances were referred to as PT1, PT2, PT3 and PT4.

Before the baseline session, each subject was asked to stand still for a few seconds to record a static data set. During the experiment, each subject's kinematics, EMG and applied wrench data were recorded for the analysis. The time histories of all gait parameters were normalized in time to 100% of the gait cycle, where a gait cycle was defined from a right heel strike event (RHS) to subsequent right heel strike. The farthest anterior position of the heel marker with respect to the sacrum marker was used to define the heel strike (HS) event and the farthest posterior position of the toe marker with respect to the sacrum marker was used to define the toe-off (TO) event. These events were used to estimate the durations of double support (DS) phases, single support (SS) phases, stride time and stance time during a gait cycle. Gait cadence was defined as the number of steps per minute. Lower limb sagittal plane joint angles were estimated from the human segment marker data. EMG signals were post-processed using a band-pass filter (4th order Butterworth, 40-450 Hz) and a full-wave rectification. The signal was smoothened using a low pass filter (n=4, fc=6 Hz). For every subject, EMG data of each muscle were normalized to the peak values recorded during the baseline session. EMG root mean square (RMS) amplitudes and linear envelop peak values were computed to estimate the level of muscle activation during the different trials of the experiment.

An asymmetric measure was defined to evaluate the gait symmetry, given as $$\text{Asymmetric parameter} = 100 \times \frac{(R-L)}{(R+L)}, \text{ or} \quad (33)$$

$$\text{Asymmetric parameter} = 100 \times \frac{(f-i)}{(f+i)} \quad (34)$$

where R and L represent the values of right and left limb parameters respectively. The values of a gait measure, which are not associated with a particular limb, were divided into initial, i, (1 to 50% gait cycle) and final, f, (51 to 100% gait cycle). A zero value of the asymmetric measure implies perfect symmetry while a positive/negative value means higher/lower R (or f) value compare to L (or i) values. Eq. 33 was used to calculate the asymmetry in the stance phase and hip flexion-extension range of motion (ROM). Eq. 34 was used to calculate the asymmetry in the anterior-posterior and vertical pelvic center motion over a gait cycle. The centroid of three pelvic anatomical markers was calculated to define the position of the pelvic center. A right limb angle representing the direction of the selected force vector in the sagittal plane was also calculated from the RILIA and RANK markers, shown as θ in the FIG. 13 (part a).

To study the performance and response of the group to the applied external wrench, gait measures from the last five gait cycles for trials BL, T6 & PT4 and from the first five gait cycles for trials T1, C1 & PT1 were analyzed. The data were first checked against the sphericity violation using the Mauchly's test and the Hyund-Feldt correction was applied when the data violated the condition. One way repeated measure ANOVA was performed to determine the statistical significance (defined as p<0.05). The Bonferroni-Holm significant difference test was performed when a statistical significance was identified. Values plotted in the following section are the means±standard errors.

All subjects successfully completed all sessions of the experiment. During the experiment, very few instances were recorded with occluded markers or the optimization scheme not being able to find the feasible cable tension values. The maximum and minimum values of the three force components during a gait cycle averaged over the group during the training trials T1, T3 and T6 are reported in Table 6. The $F_X$, $F_Y$ and $F_Z$ values varied from −1.4 to 0.35% BW, −3.7 to 4.5% BW and −12.75 to −8% BW respectively during a gait cycle over the training session. The root mean square error (RMSE) between the selected and applied force values in the medial-lateral (X), anterior-posterior (Y) and vertical (Z) directions were under 0.5, 1 and 1.4% BW respectively, refer to Table 6. One way repeated measure ANOVA did not report any significant change in the force values between trials T1, T3 and T6 in the three directions except for the minimum $F_X$ values. The $F_X$ minimum values during the trial T1 were statistically different from the corresponding values during the trials T3 and T6. The maximum and minimum values of the external moment components resolved at the pelvic center averaged over the group during trials T1, T3 and T6 are also reported in Table 6. The applied external moment components were within the selected level of ±6 Nm over the training session.

TABLE 6

Applied force values during the training trials

|  |  | T1 | T3 | T6 | p-value |
|---|---|---|---|---|---|
| RMSE (% BW) | $F_X$ | 0.28 | 0.33 | 0.29 | =0.1 |
|  | $F_Y$ | 0.92 | 0.95 | 0.90 | =0.6 |
|  | $F_Z$ | 1.30 | 1.26 | 1.33 | =0.5 |
| Maximum (% BW) | $F_X$ | 0.34 | 0.19 | 0.19 | =0.1 |
|  | $F_Y$ | 4.25 | 4.38 | 4.47 | =0.1 |
|  | $F_Z$ | −8.35 | −8.20 | −8.03 | =0.1 |
| Minimum (% BW) | $F_X$ | −1.02 | −1.36 | −1.28 | =0.001 |
|  | $F_Y$ | −3.44 | −3.57 | −3.68 | =0.3 |
|  | $F_Z$ | −12.55 | −12.72 | −12.71 | =0.6 |
| Maximum (Nm) | $M_X$ | 4.81 | 4.41 | 4.65 | =0.4 |
|  | $M_Y$ | −1.46 | −1.52 | −1.46 | =0.8 |
|  | $M_Z$ | −8.35 | −8.20 | −8.03 | =0.4 |
| Minimum (Nm) | $M_X$ | −2.68 | −3.35 | −3.36 | =0.04 |
|  | $M_Y$ | −3.42 | −3.95 | −3.8 | =0.06 |
|  | $M_Z$ | −1.32 | −1.62 | −1.51 | =0.02 |

The pelvic center anterior-posterior and vertical displacements are plotted in FIG. 18A during different experimental trials for a representative subject. Asymmetric changes were observed in the anterior-posterior pelvic motion over a gait cycle during the trials T1, T6, C1 and PT1. As seen in FIG. 18A, the $y_f$ values were larger during the trials T1 and T6, while the $y_i$ values were larger during the trials C1 and PT1. Here, $y_i$ and $y_f$ represent pelvic center range of motion (ROM) during the left and right swing phases respectively. A significant effect of the training with the applied force vector was reported in the values of anterior-posterior pelvic motion asymmetric measure, $$\frac{y_f - y_i}{y_f + y_i},$$

(p≤0.05), refer to FIG. 18A part b. The post-hoc pairwise analysis reported that the asymmetric measure values were significantly positive in the presence of the applied force vector (T1 and T6) and significantly negative when the applied force vector was removed (C1 and PT1) compared to the baseline (BL) values.

The pelvic center motion in the vertical direction was asymmetric during the trials T1, T6, C1 and PT1, with reduced pelvic motion range in the final part of the gait cycle, $z_f$, refer to FIG. 18A. Significant asymmetric changes were reported in the vertical pelvic motion (p≤0.05), refer to FIG. 18A. The asymmetric measure in the vertical direction, $$\frac{z_f - z_i}{z_f + z_i},$$

had significant negative values during the training trials (T1 and T6) and catch trial (C1) compared to the baseline values. Negative values of the asymmetric measure were also reported during the post-training sessions, but these values were not statistically different from the baseline values. The pelvic center ROM in the medial-lateral direction, $P_X$ ROM, values are reported in Table 7. The $P_X$ ROM values reduced during the training and post-training trials compared to baseline values. The significant difference was observed between pairs C1-BL and C1-T1.

TABLE 7

Changes in the gait parameter values during the experiment.

|  | (T1-BL)/BL | (C1-BL)/BL | (T6-BL)/BL | (PT1-BL)/BL | (C1-T1)/T1 | (PT1-T6)/T6 | p-value |
|---|---|---|---|---|---|---|---|
| Px ROM | 0.0606 | −0.1793 | −0.091 | −0.0817 | −0.2262 | 0.0101 | 0.001 |
| Right Stance | −0.0044 | 0.0122 | 0.005 | 0.0159 | 0.0166 | 0.0108 | 0.001 |
| Left Stance | 0.0096 | −0.0141 | 0.0069 | −0.0017 | −0.0235 | −0.0087 | 0.001 |
| Cadence | 0.0384 | 0.0221 | 0.0096 | −0.0216 | −0.0156 | −0.0309 | 0.05 |
| Right limb ROM | −0.0345 | −0.0216 | 0.0232 | −0.0165 | 0.0133 | −0.0388 | 0.05 |
| LMG RMS | 0.1412 | 0.0699 | 0.0531 | −0.0043 | −0.0624 | −0.0545 | 0.07 |
| LSOL RMS | 0.1257 | −0.0891 | 0.0903 | 0.0621 | −0.1909 | −0.0258 | 0.24 |
| LTA RMS | 0.0413 | −0.0806 | 0.0033 | −0.1321 | −0.1171 | −0.1349 | 0.05 |
| LVL RMS | 0.294 | −0.0207 | 0.1538 | −0.1918 | −0.2432 | −0.2995 | 0.001 |
| LRF RMS | 0.3714 | 0.0686 | 0.0773 | −0.2722 | −0.2208 | −0.3245 | 0.001 |
| LBF RMS | 0.0569 | 0.0211 | −0.0384 | −0.1386 | −0.0339 | −0.1042 | 0.12 |
| RMG RMS | 0.1029 | 0.1406 | −0.0539 | −0.0049 | 0.0341 | 0.0518 | 0.05 |
| RSOL RMS | 0.174 | 0.1599 | 0.0667 | 0.0319 | −0.0119 | −0.0325 | 0.05 |
| RTA RMS | −0.0322 | 0.232 | −0.0051 | 0.0427 | 0.273 | 0.0481 | 0.05 |
| RVL RMS | 0.0693 | 0.5228 | 0.3477 | 0.0128 | 0.4241 | −0.2485 | 0.001 |
| RRF RMS | 0.0833 | 0.6189 | 0.2799 | 0.0582 | 0.4945 | −0.1732 | 0.001 |
| RBF RMS | 0.0766 | 0.1749 | 0.2235 | 0.0296 | 0.0913 | −0.1584 | 0.37 |

* represent the pairwise comparisons reaching significance.

FIG. 18A (part a) shows pelvic center anterior-posterior and vertical displacements during different training trials for a representative subject. A gait cycle was defined from RHS to subsequent RHS. FIG. 18A (part b) shows anterior-posterior and vertical pelvic motion asymmetric measures for the group during different trials of the experiment. Significant changes were reported between BL-T1, BL-C1, BL-T6, BL-PT1, T1-C1 and T6-PT1 for the anterior-posterior asymmetric measure values. Significant changes were also reported between BL-T1, BL-C1 and BL-T6 for the vertical asymmetric measure values.

Figure 18B:
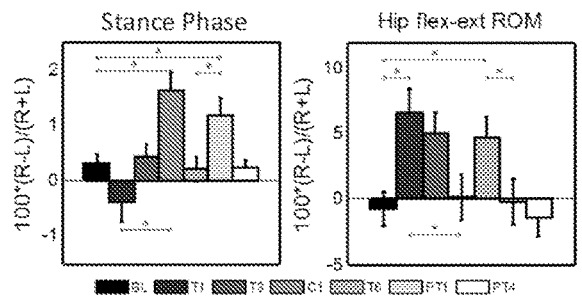
FIG. 18B shows stance phase asymmetric measure for a group during trials of an experiment.

FIG. 18B shows stance phase asymmetric measure for the group during different trials of the experiment. Significant changes were reported between BL-C1, BL-PT1, T1-C1 and T6-PT1 for the stance phase asymmetric measure values. Hip flexion-extension range of motion (ROM) asymmetric measure changed significantly during the training session. Significant changes were reported between BL-T1, BL-T6, T1-C1 and T6-PT1 for the hip flexion-extension ROM asymmetric measure values.

Figure 18C:
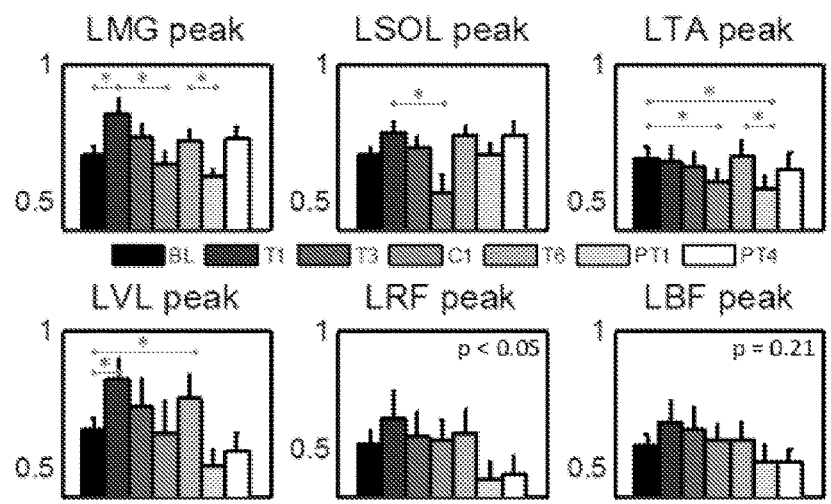
FIG. 18C part a shows left limb muscles peak values during different trials of the experiment. '*' represent the pairwise comparisons reaching significance and part b shows right limb muscles peak values during different trials of the experiment.
Figure 18C:
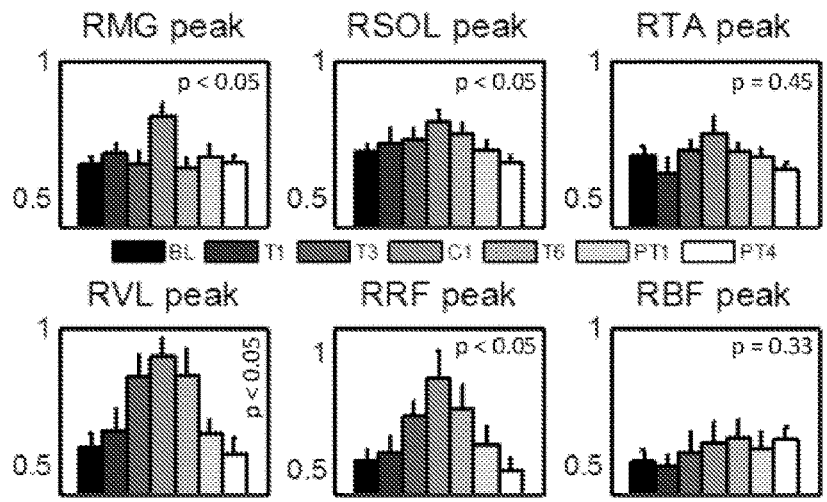

FIG. 18C (part a) shows left limb muscles peak values during different trials of the experiment. '*' represent the pairwise comparisons reaching significance. FIG. 18D (part b) shows right limb muscles peak values during different trials of the experiment. No pairwise significance was reported in the chosen pairs.

Significant changes were reported in the values of stance phase asymmetric measure, $$\frac{R-L}{R+L}$$

where R and L denote the right and left stance phase durations as a percentage of gait cycle, ($p \leq 0.05$), refer to FIG. 18B. The stance phase asymmetric measure values were negative during T1 and positive during T6. However, the asymmetric measure values during the training session were not statistically different from the baseline values. The post-hoc pairwise analysis reported that the asymmetric measure values during the catch and post-training trials (C1 and PT1) were significantly different from the baseline values. The changes in the left and right stance phase durations are reported in Table 7. The left stance values during the training trials (T1 and T6) were significantly higher than the baseline values. Longer right stance durations were reported in the absence of the applied force, such that significant difference was reported between trials BL and PT1. Further, subjects walked with higher cadence values during the training session ($p \leq 0.05$), such that cadence values during T1 were significantly higher than BL, refer to Table 7. Cadence values decreased during trials C1 and PT1 but were not statistically different from the trial BL.

The hip flexion-extension range of motion (ROM) asymmetric measure values, $$\frac{R-L}{R+L}$$

where R and L denote the right and left hip flexion-extension ROM, changed significantly during the experiment ($p \leq 0.05$), refer to FIG. 18B. These values were significantly positive during the training trials (T1 and T6) compared to the baseline values, mainly due to larger right hip flexion-extension ROM values. However, values during the catch and post-training trials were close to the baseline level. The changes in the values of right limb angle ROM during the experiment were also statistically significant ($p \leq 0.05$), refer to Table 7. These values reduced during T1 and then increased with progression of the training session, though the only statistical significance was reported between values of trials T6 and PT1.

Left lower limb peak muscles values are plotted in FIG. 18A and the changes in the RMS values are reported in Table 7. Significant changes were reported in various muscles peaks and RMS values ($p \leq 0.05$). The post-hoc pairwise analysis reported that the LTA peak values and the LRF RMS values during BL were significantly higher than the corresponding values during PT1. Further, the peak values during BL were significantly lower than T1 for LMG and significantly lower than T1 and T6 for LVL. Additionally, the peak values during C1 were significantly lower than BL for LTA and significantly lower than T1 for LMG and LSOL. Peak values from the right lower limb muscles are plotted in FIG. 18C (part b) and the changes in the RMS values are reported in Table 7. One way repeated measure ANOVA reported significant changes in various muscles peaks and RMS values ($p \leq 0.05$) but the pairwise analysis did not report significant changes in the chosen pairs. In general, the peak values of the right limb muscles RSOL, RVL and RRF increased gradually with the progression of the training session. These values were higher than the baseline values also during the catch trial. Similarly, the RMS values of right limb muscles RRF and RVL increased with the training session and were also higher during the catch trial.

In this work, an external force vector with a magnitude of 10% BW was applied on the human pelvis. This force was directed along a vector parallel to the unit vector û, from the right iliac crest (RILIAC) to the right ankle (RANK). During the experiment, the average magnitude of the applied force in the vertical direction, $F_Z$, varied from −8 to −12.75% BW over a gait cycle. Thus, the $F_Z$ component was directed downward on the pelvis and provided external vertical load during walking. Since the anterior-posterior component of the vector û changes its direction with the motion of right leg during a gait cycle, the average magnitude of the anterior-posterior force component, $F_Y$, varied from 4.5% BW at RHS to −3.7% BW at RTO. Thus, the $F_Y$ component provided an external forward pull on the pelvis for a part of a gait cycle and an external backward pull for the rest of the gait cycle. In the medial-lateral direction, the force component variations were small, −1.4 to 0.35% BW. Therefore, the applied force vector was mainly confined in the sagittal plane of walking.

The applied force values were calculated based on the position of RANK with respect to RILIAC, therefore any adaptation in the right foot trajectory during a gait cycle would be reflected in the measured force values. During the training session, no significant changes were reported in the measured force values along the anterior-posterior and vertical directions. In addition, the changes in the right limb angle values were also not significant during the training session. Thus, the subjects did not adapt the position of RANK (or right foot) with respect to RILIAC (or pelvis) in the sagittal plane. Interestingly, the immediate response of the subjects to the applied force vector was to modify the pelvic motion in the sagittal plane. Asymmetric changes were observed in both the anterior-posterior and vertical directions. This was perhaps because the force vector was applied on the pelvis and adapting a distal segment's kinematics, right foot motion, might be complex to achieve.

For a healthy individual, the pelvic anterior-posterior motion has almost twice the gait frequency and is fairly symmetrical during a gait cycle. The $F_Y$ component during the current experiment applied a backward pull on the pelvis at the beginning of the right swing phase and applied a forward pull at the end of the right swing phase. The $F_Y$ values changed smoothly during this period but at a rate proportional to the right swing phase duration. Thus, the pelvic range of motion (ROM) in this direction increased during the right swing phase. Since the treadmill speed was constant during the experiment, the subjects reduced the pelvic ROM during the left swing phase. The asymmetry in the anterior-posterior pelvic motion reduced as the training session progressed but remained significantly different compared to the baseline values.

In the vertical direction, the pelvic motion of healthy individual has almost twice the gait frequency and is substantially symmetrical as well. In the current experiment, the $F_Z$ component of the force was directed downward on the pelvis, which reached the maximum magnitude around each leg's mid swing phase. Moreover, at RTO there was a backward $F_Y$ component on the pelvis while at LTO there was a forward $F_Y$ component. The net effect of $F_Z$ and $F_Y$ at RTO would therefore require an extra push-off effort. Since subjects use pelvis in transferring forces from the lower extremity to the trunk during the forward propulsion of the body, subjects reduced the pelvic vertical motion during this phase. Thus, the reduced pelvic vertical ROM during the final part of the gait cycle (50-100% gait cycle) was observed over the complete training session.

The effect of the applied force was also reported in other gait parameters. For example, asymmetry was reported in the hip flexion-extension ROM during the training session. This change was mainly due to larger right hip flexion-extension values, which would have been a compensatory response to the reduced pelvic vertical motion during the right swing phase. The applied force vector also modified the limb support periods during a gait cycle. The left stance phase durations increased significantly during the training trials, though the changes in the stance phase asymmetric measure were not significant. As the training session progressed, small reduction in the left stance duration was observed. The changes in the left stance duration were in response to the anterior-posterior force component, which modified the pelvic anterior-posterior motion and created the need to modify the limb support periods. In the current experiment, subjects adaptation to the applied force was evaluated during the catch and post-training trials. Negative aftereffects were reported in the pelvic anterior-posterior motion during both the catch and post-training trials. The absence of external force on the pelvis led to larger pelvic anterior-posterior ROM during the left swing phase and reduced ROM during the right swing phase. This change in the pelvic anterior-posterior motion resulted in asymmetric change in the limb support phases. Notably, the subjects spend significantly longer part of the gait cycle in the right stance phase. Unlike the negative aftereffects in the anterior-posterior direction, the reduced pelvic motion in the vertical direction during the final part of the gait cycle was retained. All these changes show subject adaptation to the applied force vector, which indicate recalibration of the existing motor commands. Since the applied force was removed at the middle of the training session without the subjects' knowledge during the catch trial, stronger aftereffects were observed compared to the post-training trials.

Lower limb muscles activity pattern also show subjects' adaptation to the applied asymmetric force vector. The shank muscles, Gastrocnemius (MG) and Soleus (SOL), contribute to the body support during a gait cycle. Additionally, the SOL also contributes to the forward propulsion of the body. In the current experiment, higher activities of the left shank muscles, LSOL and LMG, at the start of the training session were in response to the $F_Y$ force component, which essentially modified the body's balance. With the progression of the training session, decrease in the left shank muscles activity and increase in right shank muscles activity were observed. Notably, these changes in the shank muscle activity were in accordance with the reported changes in the limb support periods. Moreover, the increase in RSOL activity during the training session represents subject adaptation to the applied force, which required extra push-off effort at RTO. Due to this adaptation, subjects kept the high RSOL activity even when the external force was removed, which affected the body's balance and was seen as an aftereffect to the applied force.

During a gait cycle, the thigh muscles, Vastus Lateralis (VL) and Rectus Femoris (RF), contribute towards lower leg extension and allow body to rise against the body weight. In the current experiment, there was an external downward force on the pelvis in addition to the subjects' weight. Therefore, the increase in the RF and VL activation levels in both limbs during the training was to balance the external weight bearing provided by the $F_Z$ force component on the pelvis. The increased activation of RRF and RVL when the applied force was removed was to balance the effect of higher pelvic acceleration caused by higher RSOL activities and pelvic motion aftereffects.

The asymmetric external force used in this work provides a motor adaptation approach to gait rehabilitation. This is so because the applied force vector modifies the gait requirements while walking and drive the human CNS to make corrections to minimize the induced errors by modifying the motor commands. The vertical component of the force vector increased the weight bearing during walking. In contrast, the anterior-posterior component altered the body's balance during walking. Both these requirements are very critical during gait and are very effectively accomplished during a healthy individual's walking. However, due to lack of muscle power and control, individuals with neural impairments are significantly limited. Such inability does not affect one specific gait measure but affects the overall gait performance.

Unlike many interventions which apply forces at the lower limbs, where the goal is typically to correct either the swing phase gait measures or the spatio-temporal gait measures during walking, the methods and system presented herein for gait intervention apply forces at the human pelvic level to target critical stance phase parameters, weight bearing and limb support period. The results show that the strategies for adaptation to the external forces on the pelvis have the potential to influence the stance and swing phases of both legs.

As a result of the applied force, healthy subjects developed asymmetric gait kinematics, such as pelvic displacement in the sagittal plane, hip flexion-extension ROM and stance phase duration, and kinetics, such as lower limb muscle activity. Subjects adapted to the applied force during the training session to show aftereffects in the gait kinematics and kinetics, such as longer right stance phase and higher right leg muscle activity, when the applied force was removed. These results indicate recalibration of the motor commands.

This paradigm when extended to individuals with hemiparesis is believed to be very useful. Training with such force vector, where magnitude can be regulated, when done in multiple sessions can show improvements in weight bearing capability with positive effects on gait symmetry and walking speed. In gait rehabilitation literature on stroke survivors, it has been shown that despite compromised nervous system these patients are able to adapt their gait pattern in response to the applied intervention. Gait adaptation in patients with hemiparesis may be treated using the current paradigm.

A methodology was developed and demonstrated to apply a subject specific gait intervention using the Active Tethered Pelvic Assist Device (A-TPAD). During walking with the A-TPAD, the human motion is monitored in real-time using a motion capture system to calculate the selected external wrench values. An online optimization scheme is used to compute the selected cable tension values to be applied. The direction of the applied force in the current experiment was calculated using the pelvis and foot markers in real-time. Indeed, the A-TPAD can be used to provide other subject's gait specific interventions as well.

Other advantages of A-TPAD include the flexibility to choose the number of motors and their placements to achieve different cable configurations to apply any selected external wrench on the pelvis. Being a cable-driven system, the A-TPAD does not add undesirable mass/inertia on the subject and does not undesirably constrain the human mobility. In contrast, the robotic exoskeletons using rigid link members for actuation can affect human walking dynamics, as they don't actuate all the lower limb degrees-of-freedom (DOFs) and also add external mass/inertia on the human. In addition, the A-TPAD can be used to apply external interventions both during the swing phase and stance phase of the gait cycle as opposed to robotic exoskeletons, which typically apply external forces on the legs only during the swing phase.

These experiments showed successful implementation of a novel asymmetric force vector directed along the right leg on the pelvis using a cable-driven A-TPAD. In addition to providing external weight bearing, the applied force vector also modified the body's balance during walking to induce limb support period adaptation. Healthy subjects adapted the kinematics and kinetics to show asymmetric walking pattern in the presence of the force vector. Aftereffects were reported when the applied force was removed showing motor adaptation. The observed changes in the stance phase duration and lower limb muscle activity of healthy individuals can be extended to individuals with hemiparesis to improve their gait performance.

Perturbation-based training programs can be more effective in reducing the risk of falling than traditional ones. This is because adaptation mechanisms to repeated unexpected perturbations can modify both reactive and proactive strategies to control dynamical gait stability. Despite the fact that perturbations leading to falls occur prevalently during walking in unlimited directions, more can be learned about adaptive changes emerge outside the plane of progression after lateral perturbations. A version of the A-TPAD applies unpredictable or random force-controlled multidirectional waist-pull perturbations while subjects walk. In tests, healthy young subjects were divided into two groups and exposed to a single training session. One group received perturbations along the Medio-Lateral (ML) direction while the other along the Antero-Posterior (AP) direction. Motor adaptation in reactive strategies was observed only in the AP component of the Base of Support (BoS) and the Margin of Stability (MoS). The outcomes of adaptation in proactive strategies depend on the direction of the applied perturbations. If perturbed in the AP direction, subjects increased their step length and AP MoS while if perturbed in the ML direction, subjects decreased their step width without modifying their ML MoS.

In everyday life, perturbations leading to falls occur in any direction and prevalently during walking. Lateral balance deficits are risk factors for falls in older adults and the majority of hip fractures results from side falls. Despite this, very few studies have analyzed subject reactions to lateral perturbations applied while walking.

During locomotion, dynamical stability is achieved through reactive and proactive strategies to control the motion of the Center of Mass (CoM) with respect to the formation of the next Base of Support (BoS). Reactive strategies are applied rapidly to correct for unexpected disturbances to balance. These involve automatic postural responses and are regulated by feedback mechanisms. Proactive strategies take place before the body encounters a potential threat to stability. The selection and planning of the appropriate movements are regulated by feedforward mechanisms that involve higher executive functions. Adaptation mechanisms to repeated unexpected perturbations can modify both the reactive and proactive strategies to control dynamical stability. Indeed, exposing subjects to repeated perturbations can result in a better correction of imbalance during the recovery phase and a modification of the gait pattern during unperturbed walking. These adaptive changes are very fast, such that the greater changes in subjects' reactions happen after the first exposure to the perturbation and can be generalized to different motor tasks and perturbations.

This phenomenon is relevant to fall-prevention. Antero-Posterior (AP) perturbations as well as Medio-Lateral (ML) perturbations are relevant to training to prevent falls. Balance control during unperturbed walking in the AP and ML directions differs in many ways. In the plane of progression, stability is principally achieved by passive mechanisms and performed by lower-level propriospinal somatosensory feedback. In the frontal plane, an adjustment of lateral foot placement at each step is necessary to achieve stability. This is believed to be performed by active mechanisms regulated by higher centers such as the brain stem and cerebellum, that integrate inputs from visual, vestibular, proprioceptive, and other sensory feedback.

In tests a modified version A-TPAD was used to apply unexpected force-controlled multidirectional waist-pull perturbations while subjects are walking on a treadmill. Cables were attached to a hip brace worn by the subject and gait events are monitored in real-time by the system. The A-TPAD applied suitable cable tension values at each motor such that a resultant force is applied to the pelvis in the selected direction. Its design provides flexibility to rapidly change the amplitude, the direction, the duration, the trigger time point, and the waveform (force temporal profile) of the perturbation.

Experiments recorded adaptations in reactive and proactive strategies for control of gait stability differ based on the direction of the applied unexpected perturbations. Healthy young subjects were divided into two groups and were exposed to a single perturbation training session. One group received perturbations of different amplitudes along the Medio-Lateral (ML) direction while the other along the Antero-Posterior (AP) direction. Eighteen healthy adults participated in the study and were assigned to either the AP group (9 males, 24.2±4.7 years old, 71.1±8.5 kg, 1.74±0.07 m) or ML group (9 males, 23.6±3.6 years old, 69.4±7.7 kg, 1.75±0.08 m). All subjects had no musculoskeletal or neurological problems.

Figure 19A:
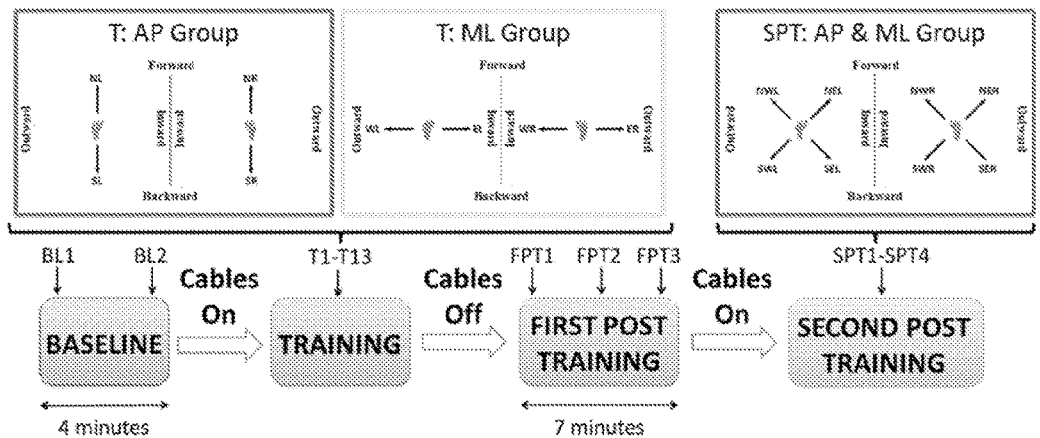
FIG. 19A shows an experimental protocol including Baseline (BL), Training (T), First Post Training (FPT) and Second Post Training (SPT) sessions.

FIG. 19A shows the experimental protocol. It includes Baseline (BL), Training (T), First Post Training (FPT) and Second Post Training (SPT) sessions. Referring to FIG. 19A, experimental sessions were carried out using A-TPAD. The heights of the pulleys were changed for each subject such that during standing each cable was parallel to the floor. A ten-camera motion capture system (Bonita-10 series from Vicon) and two Force Sensitive Resistor (FSR) pressure pads with 440 N limit (FlexiForce® from Tekscan, Massachusetts) were used as a part of the controller. The motion capture system was used to track the cable attachment locations during a calibration trial, while the FSR pressure pads were mounted on subject's shoe insoles at the calcaneus level to detect in real-time heel strike events during the experiment. The controller was implemented on a Labview, PXI real-time system (National Instrument, Austin).

When cables were attached to the subject, before giving the actual perturbation, a constant force of 14 N was applied by each motor to prevent cable slackening. Perturbations were delivered while walking at constant speed when the Left (L) or the Right (R) heel strike was detected and consisted of a trapezoidal force temporal profile (rise, hold and fall times of 150 ms duration each) with a peak force of 10%, 15% or 20% of the subject's body weight (BW). Perturbations were provided along the Antero-Posterior (AP), Medio-Lateral (ML) or Diagonal (D) directions applying a transient pulse on two (AP and ML) or one (D) of the four cables.

In order to apply a resultant force of selected magnitude and direction, a suitable cable tension value should be applied at each motor when imposing perturbations in the AP or ML directions. To do this, a calibration trial was performed before the start of the experiment. A 30 seconds walking trial was performed and cables attachment locations (on the subject and on the fixed reference frame) at each time point of interest (i.e., right and left heel strikes) were recorded and averaged between steps. The selected tension value to be applied in each motor to apply a force in the ML or AP direction was derived based on the angle each cable forms with respect to the fixed frame.

Trajectories of 40 reflective markers attached to the participants were collected at 250 Hz using a 10-camera Vicon motion capture system (Oxford metrics, Oxford, UK). Also EMG data were collected, but these will be reported elsewhere. During the BL, each subject walked on the treadmill for 4 minutes. Data collected during the last minute was used as reference in the analysis and labeled as BL2. During the T, the four cables were attached to the hip brace and both groups were exposed to perturbations applied to the pelvis at right (i.e., R) or left (i.e., L) heel strike. The AP Group was trained with forward and backward perturbations (i.e., North—N and South—S directions). Perturbations were named (i.e., NR, NL, SR, and SL) based on the foot (i.e., R or L) that contacted the ground at the time of perturbation (see top left of FIG. 19A). The ML Group was trained with rightward and leftward perturbations (i.e., East—E and West—W directions). Similarly, the perturbations were named (i.e., WR, WL, ER, and EL) based on the foot (i.e., R or L) that contacted the ground at the time of perturbation (see top center of FIG. 19A). The T session was composed of 13 blocks. In each block, 10 repetitions of the same perturbation were applied to the subject: 3 amplitudes (10%, 15% and 20% of the Body Weight—BW), 2 directions (forward and backward for the AP group—rightward and leftward for the ML group), and 2 events (R and L heel strikes) were used. In total, 12 types of different perturbations (12 blocks) were used. The 13th block was identical to the first one. The order of the perturbations was chosen randomly. During the FPT, the cables were removed and each subject walked for another 7 minutes. Data collected during the first and last minutes were used in the analysis and labeled as FPT1 and FPT3. During the SPT, the four cables were reattached to the hip brace. Both groups underwent perturbations along the D directions (i.e., North West—NW, North East—NE, South West—SW and South East—SE). The perturbations were named (i.e., NWR, NER, SWR, SER, NWL, NEL, SWL, and SEL) based on the foot (i.e., R or L) that contacted the ground at the time of perturbation (see top right of FIG. 19A). The SPT was composed of 4 repetitions of identical blocks. In each block, 8 different perturbations were applied to the subject: 1 amplitude (20% BW), 4 directions (i.e., NW, NE, SW, SE) and 2 events (R and L heel strikes) were used. The order of the perturbations was chosen randomly. In the subsequent analysis perturbations with a lateral component were distinguished between outward and inward perturbations. If perturbations were applied at right/left heel strikes and have a rightward/leftward component they were referred to as outward perturbations (i.e., ER and WL for the T session; NER, SER, NWL and SWL for the SPT session). Instead, if perturbations were applied at right/left heel strikes and have a leftward/rightward component they were referred to as inward perturbations (i.e., WR and EL for the T session; NEL, SEL, NWR and SWR for the SPT session). Basically, during inward perturbations the force applied on the pelvis was in the direction of the free leg while during outward perturbations the force applied was in the direction of the leg that last contacted the ground.

Walking speed (v) was normalized for each subject in accordance with the principle of dynamic similarity and was kept the same for the duration of the experiment such that:

$$v=\sqrt{0.15 \times g \times l}. \tag{35}$$

where g is the gravitational acceleration and l is the subject's leg length. Subjects wore a safety harness during T and SPT sessions to prevent them from falling but without restricting their movements. The subjects were aware that they would be perturbed at the waist when the cables were attached, but were not informed about the magnitude, the direction or the timing of the perturbations. The number of steps between perturbations was randomized (4-15 steps between perturbations). Noticeably, the subjects were aware they would not be perturbed during sessions BL and FPT because the cables weren't attached to the hip belt.

Marker paths were low-pass filtered at a cut-off frequency of 7 Hz using a fourth-order, zero-lag Butterworth filter. Timing of foot dynamic phase (i.e., heel strike and toe off) was derived from heel and toe markers' position as illustrated in. A 16-segment biomechanical model was developed. Whole body Centre of Mass (CoM) position was calculated as the weighted sum of the 16-segment model.

Dynamical stability was quantified both during unperturbed walking (sessions BL and FPT) and balance recovery (sessions T and SPT) using the Margin of Stability (MoS). The MoS is given by the difference between the Base of Support (BoS) and the Extrapolated Centre of Mass position (XCoM).

The XCoM is an estimate of the position at which the body center of mass can be brought to rest given its current position and velocity. Both the AP and ML components of the MoS were assessed at right and left heel strikes in sessions BL and FPT, and at the end of the compensatory step (i.e., first heel strike after the onset of the perturbation) in sessions T and SPT.

Figure 19B:
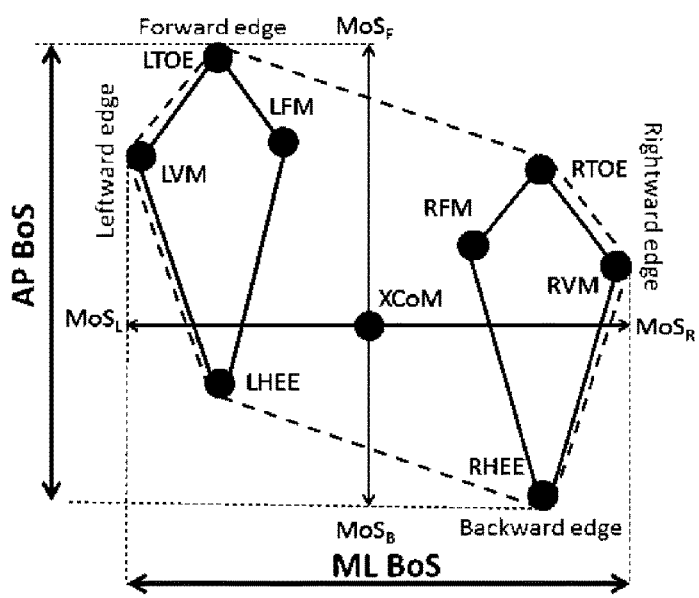
FIG. 19B is a schematic illustration of outcome parameters of tests.

FIG. 19B shows a schematic illustration of the outcome parameters. The BoS was estimated at right (i.e., R) or left (i.e., L) heel strike or at the end of the compensatory step (in both cases in a double support configuration) using the markers from both feet. More in detail, the foot markers on heels (LHEE and RHEE), toes (LTOE and RTE), 1th (LFM and RFM) and 5th (LVM and RVM) metatarsal heads were used to estimate the edges of the BoS (see FIG. 19B). The AP position of the most backward/forward marker was used as backward/forward edge of the BoS. Similarly, the ML position of the most leftward/rightward marker was used as leftward/rightward edge of the BoS. AP BoS was defined as the distance between the forward and backward edges of the BoS. ML BoS was defined as the distance between the rightward and leftward edges of the BoS. The AP and ML components of the XCoM were computed as:

$$XCoM_{AP,ML}=CoM_{AP,ML}+CoM_{AP,ML}/\sqrt{g/h_{CoM}} \tag{36}$$

where $CoM_{AP,ML}$ and $CoM_{AP,ML}$ are the AP and ML position and velocity of the CoM, $h_{CoM}$ is the estimated pendulum length based on the height of the CoM during standing and g is the gravitational acceleration.

As a first step, both the backward ($MoS_B$) and forward ($MoS_F$) component of the AP MoS were estimated using the backward or the forward edges of the BoS and $XCoM_{AP}$. Similarly, for the ML direction, both the leftward ($MoS_L$) and rightward ($MoS_R$) component of the ML MoS were estimated using the leftward or the rightward edges of the BoS and $XCoM_{ML}$. The MoS was defined based on the direction of movement of the XCoM. Accordingly, during unperturbed walking trials (BL and FPT sessions), the MoS was defined with respect to the last foot to contact the ground. The AP MoS was defined by the $MoS_F$ while the ML MoS was defined by the MoSR or the MoSL if calculated at right or left heel strike. Both components of the MoS and BoS were calculated for the first 40 left and right heel strikes. For each subject and trial, the mean MoSs and BoSs were calculated as the average value between all the accounted steps. During the compensatory step (T and SPT sessions), the MoS was defined based on the direction of the applied perturbation. Hence, the AP MoS was defined by the $MoS_B$ if the perturbation had a backward component (i.e., SR, SL, SWR, SWL, SER and SEL, see FIG. 19A), otherwise it was defined by the $MoS_F$ (i.e., NR, NL, NWR, NWL, NER and NEL). If the perturbation had no forward or backward component the AP MoS was defined as in unperturbed gait by the $MoS_F$ (i.e., WL, WR, EL and ER). The ML MoS was defined by the $MoS_L$ if the perturbation had a leftward component (i.e., WR, WL, NWR, NWL, SWR, SWL) or by the $MoS_R$ if the perturbation had a rightward component (i.e., ER, EL, NER, NEL, SER, SEL). If the perturbation had no lateral component the ML MoS was defined as in unperturbed gait by the $MoS_R$ or the $MoS_L$ if calculated at right (i.e., NL, SL) or left (i.e., NR, SR) heel strike, respectively.

For each session, both components of the MoS and BoS were used as dependent measures. During the T session, a three-way repeated measures ANOVA was performed independently in each group to determine the main and simple interaction effects of amplitude (3 levels: 10% BW, 15% BW and 20% BW), repetition (10 levels: R1-R10) and type (2 levels: forward (i.e., NR and NL) and backward (i.e., SL and SR) for the AP Group; outward (i.e., ER and WL) and inward (i.e., EL and WR) for the ML Group) of the perturbations. During unperturbed walking trials (BL and FPT), a one-way repeated measures ANOVA was performed independently on each group to determine the main effect of trial (3 levels: BL2, FPT1 and FPT3). During the SPT session, a mixed design repeated measures ANOVA was used: AP type (2 levels: forward (i.e., NER, NEL, NWR and NWL) and backward (i.e., SER, SEL, SWR and SWL), ML types (2 levels: outward (i.e., NER, NWL, SWL and SER) and inward (i.e., NEL, NWR, SWR and SEL), repetitions (4 levels: R1-R4) served as within-subjects factors and subject group (ML group and AP group) served as the between-subject factor. For each dependent measure, the Lilliefors and the Mauchly's Tests were performed to check the normality assumption of the data and the sphericity assumption violation, respectively. The Huynd-Feldt correction was applied when the data violated the condition of sphericity. The main and simple interaction effects of these analyses were followed up with planned comparisons using Student's paired t-tests. Statistical significance was set at $p<0.05$.

Regardless of the group, all subjects completed the experiment without difficulty. Subjects in the AP and ML groups walked at an average speed of 1.09±0.04 m/s and 1.09±0.03 m/s, respectively. After the perturbation, all participants were able to recover their balance without falling.

Figure 20A:
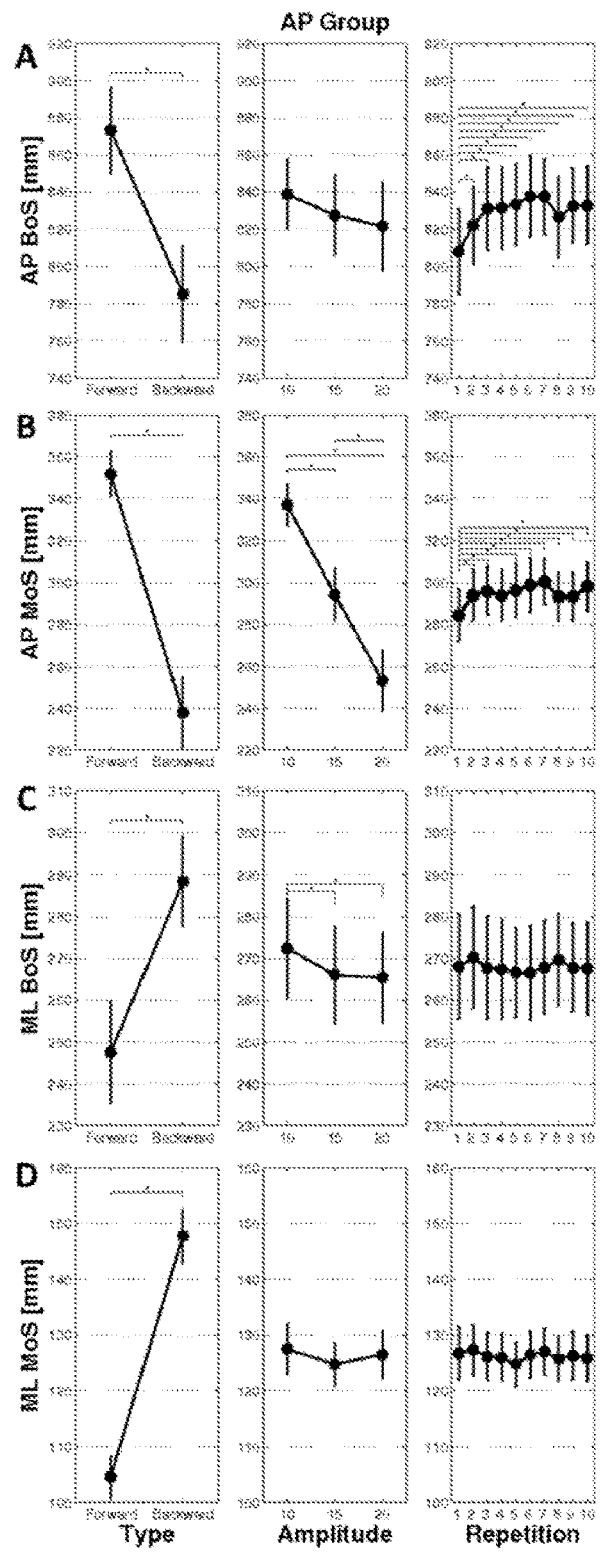
FIG. 20A show results obtained during the T session by the AP group.

FIG. 20A show results obtained during the T session by the AP group. FIG. 20A parts A and B report the AP component of the BoS and the MoS, respectively. Significant main effects of the type (AP BoS: p=0.006; AP MoS: p<0.001) and repetition (AP BoS: p<0.001; AP MoS: p=0.007) of the perturbations were observed for both metrics. More in detail, backward perturbations were characterized by lower values than forward ones. Perturbations with a backward component were more destabilizing for the subjects in the AP direction. They took shorter steps and consequently they had a smaller AP MoS, closer to instability. The values obtained during the first repetition (R1) were significantly lower (p<0.05) from all the other repetitions (R2-R10). Subjects adapted their reaction by increasing their compensatory step length with a greater AP MoS. Also if subjects slightly decreased their AP BoS with the increment of perturbations' amplitude, significant effects of the amplitude (p<0.001) were observed only for the AP MoS. As the amplitude of the perturbations increased, the AP MoS decreased in a linear fashion (p<0.01).

FIG. 20A parts C and D reports the ML component of the BoS and the MoS, respectively. Also if perturbations had only an AP component, a significant main effect of the type (ML BoS: p<0.001; ML MoS: p<0.001) of perturbations was observed for both the ML BoS and ML MoS. Backward perturbations were characterized by greater values than forward ones: subjects make a wider step if perturbed in the backward direction, resulting in a greater ML BoS and, consequently, ML MoS. A significant main effect of the amplitude (p=0.002) was found only for the ML BoS, as the amplitude of the perturbations increased subjects took a narrower step. A type×amplitude interaction (ML BoS: p<0.001; ML MoS: p<0.001) was found for both metrics. When forward perturbations were applied, greater amplitudes were related to lower values of the ML BoS (10% BW Vs. 15% BW: p=0.0014; 10% BW Vs. 20% BW: p<0.001; 15% BW Vs. 20% BW: p=0.041) and the ML MoS (10% BW Vs. 15% BW: p<0.001; 10% BW Vs. 20% BW: p<0.001) When backward perturbations were applied, greater amplitudes were related to higher values of the ML BoS (10% BW Vs. 20% BW: p=0.003) and the ML MoS (10% BW Vs. 20% BW: p=0.014; 15% BW Vs. 20% BW: p=0.05). In other words, subjects decreased their step width as the amplitude increased if perturbed forward while they increased their step width if perturbed backward. Finally a significant type×repetition interaction (p=0.042) was found for the ML BoS. Subjects decreased or increased their ML BoS with the repetition of the same perturbation when perturbed in the backward or forward direction, respectively but without a modification of the ML MoS.

Figure 20B:
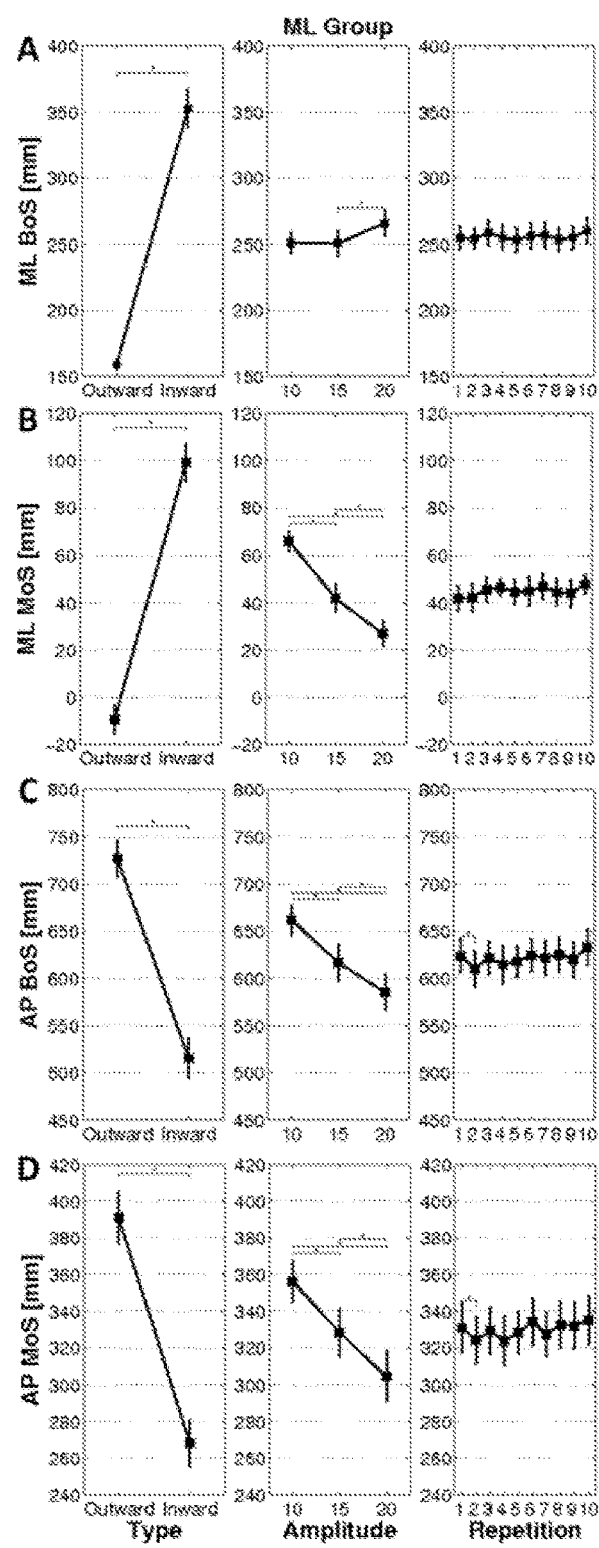
FIG. 20B shows results obtained during the T session by the ML group.

FIG. 20B shows results obtained during the T session by the ML group. FIG. 20B parts A and B report the ML component of the BoS and the MoS, respectively. Significant effects of the type (ML BoS: p<0.001; ML MoS: p<0.001) and amplitude (ML BoS: p=0.025; ML MoS: p<0.001) of the perturbations were observed for both the ML BoS and ML MoS. More in detail, outward perturbations were characterized by a lower ML MoS and ML BoS than inward ones. Greater amplitudes of the perturbations were characterized by lower ML BoS (15% BW Vs. 20% BW: p=0.0174) and ML MoS (10% BW Vs. 15% BW: p<0.001; 10% BW Vs. 20% BW: p<0.001; 15% BW Vs. 20% BW: p=0.005). Also if a type×amplitude interaction were found for the ML MoS (p=0.0132) and close to the significance for the ML BoS (p=0.0689) no distinctive differences were found between the outward and inward perturbations as amplitude varied. Outward perturbations were particularly destabilizing, especially for amplitudes greater than 10% BW. Subjects need to take a crossover step moving the compensatory leg towards the direction of the perturbation, resulting in a narrowed configuration at the end of the compensatory step. When outward perturbations of 10% BW were applied, also if the step width is narrowed (159.80±7.85 mm), subjects were still able to maintain the ML MoS on values greater than zero (20.02±5.55 mm). For 15% BW perturbations the step width was even reduced (148.88±4.95 mm), while for 20% BW it increased (168.67±6.76 mm). The magnitude of the perturbation was too high and they were not be able to maintain a ML MoS at values greater than zero (−13.70±6.2 mm for 15% BW and −34.56±9.8 mm for 20% BW), in a very unstable configuration. Also if subjects tend to slightly increase their ML BoS and MoS with the repetition of the same perturbation, no significant effect of the repetition was found (ML BoS: p=0.75; ML MoS: p=0.67).

Figure 20C:
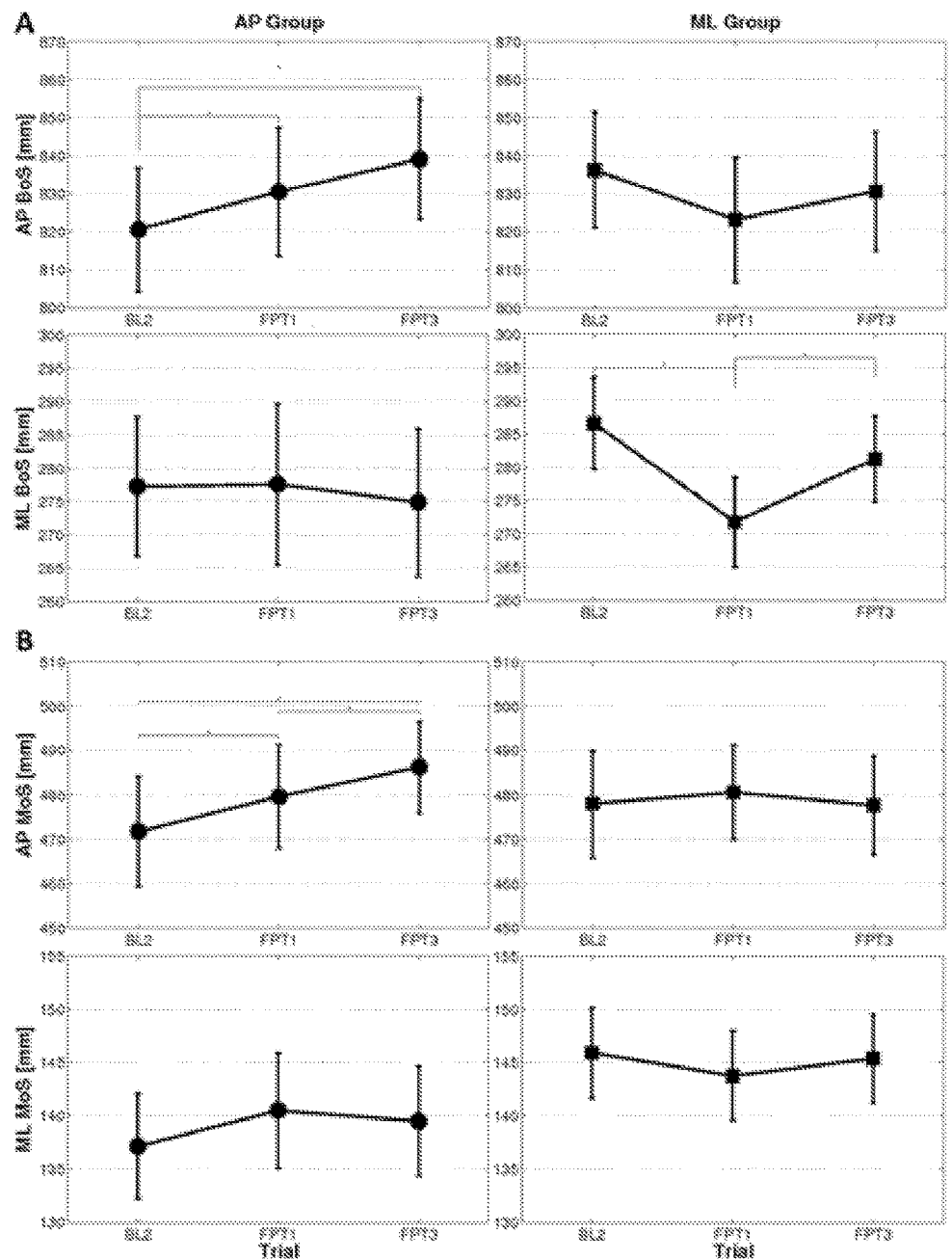
FIG. 20C relates to T sessions with parts C and D reporting the AP component of the BoS and the MoS, respectively.

FIG. 20C relates to T sessions: The outcome measures obtained by the ML group for each accounted factor are shown. From left to the right, the data reported are the Type (2 levels: Forward and Backward perturbations), Amplitude (3 levels: 10%, 15% and 20% of the BW) and Repetition (10 levels: R1-R10) factor. A. ML BoS; B. ML MoS; A. AP BoS; B. AP MoS. FIG. 20 C parts C and D report the AP component of the BoS and the MoS, respectively. Significant effects of the type (ML BoS: p<0.001; ML MoS: p<0.001), amplitude (AP BoS: p<0.001; AP MoS: p<0.001) and repetition (AP BoS: p=0.019; AP MoS: p=0.02) of the perturbations were observed for both the ML BoS and ML MoS. More in detail, outward perturbations were characterized by a greater AP MoS and AP BoS than inward ones. This is because when outward perturbations were applied subjects need to take a cross-over step, placing their recovery foot more forward than the contralateral one. On the contrary, when inward perturbations were applied, subjects rapidly step down the compensatory foot increasing their step width. Greater amplitudes of the perturbations were characterized by lower values (p<0.001). Also if perturbation were applied in the ML direction, the AP MoS was significantly affected. The values obtained during the first repetition were significantly greater than those obtained during the second one (AP BoS—R1 Vs. R2: p=0.008; AP MoS—R1 Vs. R2: p=0.035). Finally, an amplitude×repetition interaction were found for the AP BoS (p=0.029). When 10% BW and 15% BW perturbations were applied, the step length increased with the repetition of the same perturbation, while when 20% BW perturbations were applied it decreased.

Figure 20D:
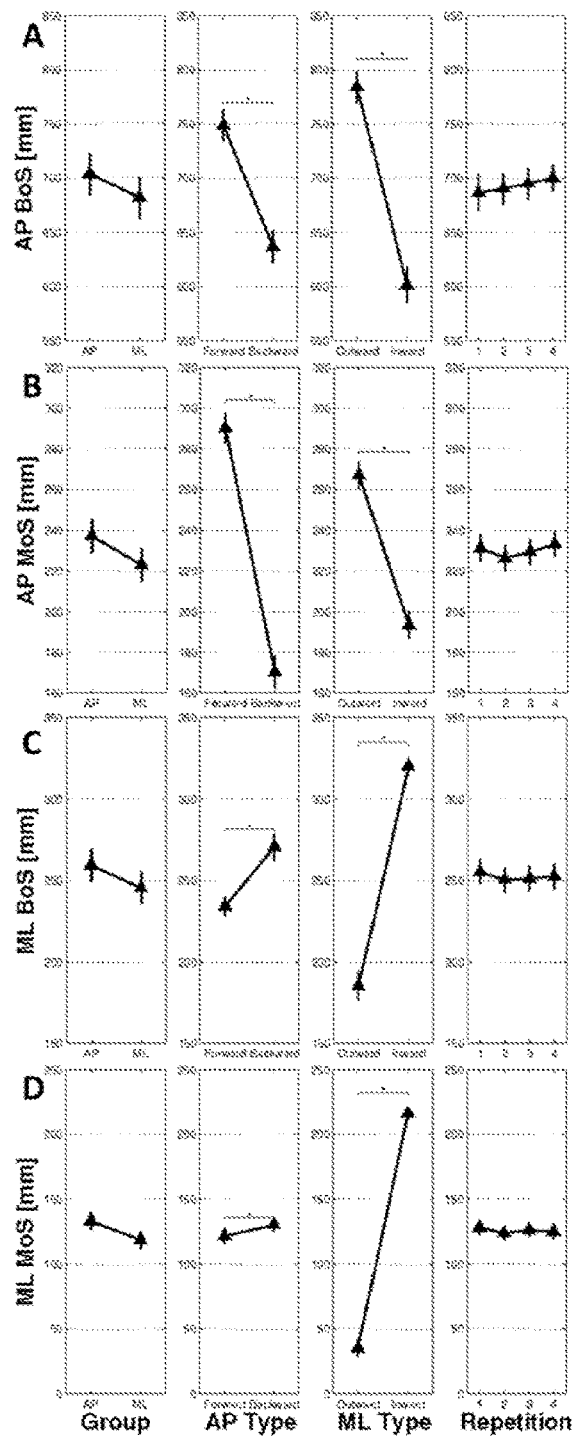
FIG. 20D show results obtained during the SPT session by the both groups.

FIG. 20D show results obtained during the SPT session by the both groups. Part A and B correspond to the AP BoS and the AP MoS, respectively. Significant effects of the AP type (AP BoS: p<0.001; AP MoS: p<0.001) and ML type (AP BoS: p<0.001; AP MoS: p<0.001) of the perturbations were observed for both the AP BoS and AP MoS. As previously found in the T session, backward and inward perturbations were characterized by lower values than forward and outward ones, respectively. No significant effect of the group or the repetition was found.

In FIG. 20D, outcome measures obtained by the AP group are shown in left part and the ML group in the right part. The effect of the training on the modification of the proactive control of stability was observed on 3 trials: BL2, FPT1 and FPT3. A. BoS (AP BoS on the top and ML BoS on the bottom); B. MoS (AP MoS on the top and ML MoS on the bottom). FIG. 20D shows results obtained during unperturbed walking trials by both groups. FIG. 20D part A shows the mean AP (top part) and ML (bottom part) BoS obtained during unperturbed walking trials by the AP (left part) and ML (right part) group. The effect of the training was to increase the step length (AP BoS) in the AP group and reduce the step width (ML BoS) in the ML group. Indeed, a significant trial effect was observed for the AP BoS in the AP group (p=0.0023) while a significant trial effect was observed for the ML BoS in the ML group (p=0.0052). Post-hoc analysis revealed that in the AP group, the AP BoS during BL2 was significantly lower than that obtained during FPT1 (AP Group—BL2 Vs. FPT1: p=0.018) and FPT3 (AP Group—BL2 Vs. FPT3: p=0.01). On the other hand, in the ML group, the ML BoS during the FPT1 was significantly lower than that obtained during BL2 (ML Group—BL2 Vs. FPT1: p=0.002) and came back towards the baseline values in FPT3 (ML Group—FPT1 Vs. FPT3: p=0.043).

These effects on the BoSs were reflected on the stability limits only in the AP group. FIG. 20D part B shows the results related to the MoS. The effect of the training was to increase the AP MoS in the AP group while no differences on the ML MoS were found in both groups. Indeed, a significant trial effect was observed for the AP MoS in the AP group (p=0.015). Post-hoc analysis revealed that in the AP group the AP MoS during BL2 was significantly lower than that obtained during FPT1 (AP Group—BL2 Vs. FPT1: p=0.022) and FPT3 (AP Group—BL2 Vs. FPT3: p=0.018). Moreover, the AP MoS continued to increase in the FPT session, with values obtained during FPT1 significantly lower than those obtained during FPT3 (AP Group—BL2 Vs. FPT1: p=0.032)

FIG. 20D shows the SPT session outcome measures for each accounted factor. From left to the right, the data reported are the group (2 levels: AP group and ML group), AP type (2 levels: forward and backward perturbations), ML type (2 levels: outward and inward perturbations) and repetition (4 levels: R1-R4) factors. A. AP BoS; B. AP MoS; A. ML BoS; B. ML MoS.

A significant AP type×repetition (p=0.019) and ML type Vs. repetition (p=0.002) interactions were found for the AP BoS. If the perturbation had a backward or an outward component the AP BoS increased with the repetitions while decreased with repetitions if the perturbation had a forward or an inward component. A significant group×repetition (p=0.01) interaction was found for the AP MoS. Post-hoc analysis revealed that the AP group showed a greater AP MoS during the first repetition (R1) of the perturbation (R1-AP group Vs. ML group: p=0.05). With the repetition of the perturbations the ML group increased the AP MoS (R1 Vs. R4 p=0.024). Also if a significant AP type×ML type (p<0.001) interaction was found for both the AP BoS and AP MoS, no distinctive changes were found in the main effect of one factor over levels of the other one.

FIG. 20D parts C and D show the ML BoS and the ML MoS, respectively. Significant effects of the AP type (ML BoS: p<0.001; ML MoS: p=0.01) and ML type (ML BoS: p<0.001; ML MoS: p<0.001) of the perturbations were observed for both the ML BoS and MoS. Backward and inward perturbations were characterized by a higher values than forward and outward ones, respectively.

A significant ML type×repetition (p=0.011) interaction was found for the ML MoS. With the repetition of the perturbations, both groups decreased their ML MoS during inward perturbations (R1 Vs. R2 p=0.003; R1 Vs. R4 p=0.001). Also if a significant AP type×ML type (p<0.001) interaction was found for both the AP BoS and AP MoS, no distinctive changes were found in the main effect of one factor over levels of the other one.

The present study investigated how adaptations of both reactive and proactive control of stability after a single training session differs in healthy young subjects based on the direction of the applied perturbations in terms of variations of both components of the BoS and the MoS. Results showed (i) a scaling effect of perturbation direction and amplitude on the reactive control of stability; (ii) an adaptation of the reactive control of stability at the end of the compensatory step in the T session only in the AP direction; (iii) an adaptation in the proactive control of stability in both groups during the FPT session, the type and extent depends on the direction of the applied perturbations delivered during the training session; (iv) no significant differences between the two groups during the SPT session.

The CNS is able to interpret multiple sensory inputs in order to produce context-dependent reactive responses. Results obtained in the present study pinpoint the distinct biomechanical affordance and demand of the neuro-musculoskeletal system due to the direction of the perturbation and these are in accordance with previous findings on multidirectional slipping-like perturbations.

Overall, when subjects were exposed to perturbations with a backward component, they make a wider and shorter step, while when exposed to perturbations with a forward component they make a narrowed and longer step than normal walking Since the ML movement of the CoM due to AP perturbations was negligible, ML MoS increased during backward and decreased during forward perturbations, respectively, with respect to normal walking. On the other hand, since AP perturbations involved an AP displacement of the CoM, the longer step implemented during forward perturbations was not enough to completely recapture the CoM such that both during forward and backward perturbations the AP MoS was still lower than during normal walking. Previous studies already showed that backward perturbations are associated with a greater postural threat associated with the selection of a more robust balance control strategy.

Overall, when subjects were exposed to perturbations with an outward component, they make a narrowed step while when exposed to inward perturbations they make a wider step than normal walking. The narrowed step during outward perturbations is needed because, especially for greater amplitudes, subjects did a crossover step. Both types of perturbations decreased the step length with respect to normal walking, but the reduction during inward perturbations was greater than for the outward perturbations. Given the concomitant reduction of the step length and the ML acceleration of the CoM due to the perturbations, both the AP and ML MoS decreased. The ML MoS decreased more for outward than inward perturbations with respect to normal walking. On the other hand, the AP MoS decreased more for inward than outward perturbations with respect to normal walking. Outward perturbations were very challenging for balance, since they involve an instable lateral configuration in the double support at the end of the compensatory step. Negative values of the ML MoS require an additional step to avoid a fall.

As expected, the perturbation effects increased with perturbation amplitude. This effect was consistent and almost linear in both directions. This was especially true for AP perturbations where the slightly non-significant reduction in the AP BoS with increasing amplitudes of the perturbations involved a linear reduction of the AP MoS. During ML perturbations, the increase of the ML BoS from 15% to 20% BW perturbations causes a slight reduction in the slope of the ML MoS curve.

The scaling effect of perturbation amplitudes during mechanical perturbations during gait has received little attention. Previous research analyzed the walking variability during continuous pseudo-random perturbations (ML oscillation of the treadmill) at multiple amplitudes. Results showed that variability increased significantly with amplitude for all subjects. Better knowledge of amplitude effects could be useful for protocol development and provide insights into the characteristic responses produced by different stimuli.

With stimulus repetition, motor adaptation mechanisms bring to a gradually diminishing of amplitude reactions with a concomitant improvement in the outcome of performance. The greatest difference across trials occurs between the first perturbation and the second identical one. This phenomenon is called "first trial effect". Whenever the perturbation direction is changed, the first trial effect immediately reemerged. Adopting a random mix of different directions and amplitudes of the perturbations can reduce stimulus predictability and reduce the effect of habituation.

In the present experiment perturbations were repeated in the T session to maximize the effect of habituation while were changed in each of the four blocks during the SPT session.

For the AP group, regardless of the type of perturbation, subjects' AP MoS was significantly lower following the first repetition compared with the consecutive disturbances within that block. Subjects adapted their reactive response by increasing their step length (AP BoS) and thereby achieving a more stable configuration (i.e., greater AP MoS) at the end of the compensatory step. During different kinds of perturbations, step length regulation appears to be important to achieve a stable configuration and elderly subjects shortened their step length during the onset of the perturbations, whereas young adults did not. If the modification of the step length found in young subjects can be extended also in elders this could be an effective strategy to improve balance reactions.

This effect was not seen in the ML group. Indeed, results did not show any form of adaptation of the reactive response for both the ML BoS and ML MoS at the end of the compensatory step. From the first to the last repetition, subjects were unable to modify their reaction and obtain a better performance in terms of stability at the end of the compensatory step.

The adaptation showed by both groups in the AP direction was transferred and rapidly lost when perturbed with diagonal perturbations. The direction-dependent effect of the training on the novel kind of perturbations delivered in the diagonal directions was to increase the AP MoS in the AP group during the first block of perturbations while had no effect on the ML MoS. As expected, since no adaptations were observed during the training in the ML direction, no group differences were observed.

Due to the training, both groups of subjects showed aftereffects. This is a distinctive characteristic of adaptation to a novel environment introduced by the repeated perturbations. If aftereffects are present, a generalized change in an internal model for planning movement is induced from the perturbation-originated sensorimotor feedback. During walking, the aftereffects implemented by the subjects are direction-dependent.

Subjects increased their average step length (AP BoS) if perturbed in the AP direction or decrease their average step width (ML BoS) if perturbed in the ML direction. Decreased step length and increased step width are common characteristics of elderly walking pattern. Both of these are associated with increased fear of falling. An increased stride width is also associated with an increased risk of falling while walking even if it is commonly assumed it increases stability due to the fact that the center of mass is recaptured more easily as it falls sideways during single leg support. The increment of risk of falling while walking with wider steps could be explained by the more lateral foot placement that actually acts to exacerbate lateral instability by increasing lateral acceleration of the center of mass. Also results from a frontal plane model stabilized by delayed feedback during standing showing that mechanical stability due to external perturbations decreases as stance width increases. If the present results can be confirmed on elderly subjects, both modifications of stride length and width can ideally improve their BoS characteristics during walking.

The modification in the step characteristic was reflected in a modification of the control of stability such that subjects in the AP Group at the end of the Training session walked with a greater AP MoS while subjects involved in the ML group reduced the lateral oscillation of their CoM such that they did not modify their ML MoS. The fact that subjects can maintain a constant ML MoS in the presence of a reduction of the ML BoS is in accordance with the theory proposed by Hof. For good control of balance, the ML BoS should be placed at a fixed position relative to the projection of the XCoM otherwise the produced error needs to be corrected at the following step. It is apparent that lateral balance is implemented by active mechanisms.

The experiment was performed by healthy young subjects. It is well know that elderly people have a gait and falling dynamics different from young subjects due to their residual physical/cognitive capabilities. Future experiments are required to verify if the present results can be extended to subjects with neuromusculoskeletal disorders with a higher risk of falling (e.g., elderly subjects, amputees, etc.).

Results showed that after a single training session both types of training protocols were associated with a modification of both the reactive (along the AP direction) and the proactive (in the direction of the applied perturbations) control of stability. Further training paradigm should may involve perturbations both in the AP and ML directions and vector sums of these. Further, z-direction impulses may be applied as well to simulate the effect of a change in terrain. These may make the effects as generalizable as possible and mimic the fact that, in everyday life, perturbations leading to falls can occur in any direction.

The A-TPAD was demonstrated to be useful for applying unexpected force-controlled multidirectional waist-pull perturbations while subjects were walking. In foregoing studies, its utility was demonstrated in applying vertical forces. A generalized configuration may apply ML, AP, and superior-inferior (SI) and combinations thereof to the human body to build stabilization competence and to simulate various conditions that may cause falls. The A-TPAD configuration using cable tension control is well-suited to this type of treatment because of the low inertial interference and concomitant ability to generate a transparent engagement with the system.

The adaptations of reactive and proactive strategies to control gait stability in terms of variations of both components of the BoS and the MoS at foot contact differed based on the direction of the applied perturbations. Distinct biomechanical affordance and demand of the neuro-musculoskeletal system due to the direction and amplitude of the perturbation were observed during the recovery responses. Motor adaptation in reactive strategies was observed only for AP balance control while no adaptation was observed for the ML balance control. The outcomes of adaptation in proactive strategies depend on the direction of the applied perturbations. If perturbed in the AP direction, subjects increased their AP BoS and MoS while if perturbed in the ML direction, subjects decreased their step width (ML BoS) without modifying their ML MoS. Results confirm that during walking balance control in the ML and AP directions is achieved in different ways.

Embodiments with CDPW and A-TPAD Features

As indicated above, other embodiments of CDRR include CDPW devices. A function of the CDPW may be, to an extent, to mimics a parent's hands which support the pelvis of the child. As does a parent, the CDPW "observes" movements and reacts to them to assist in learning how to walk. In walker embodiments, CDPW may be configured to exert gentle forces/torques on the child's pelvis responsively to sensor signals indicating their posture and balance. Sensors may measure child's position, posture, and forces of interaction between the child and the machine during their intended motion, e.g., forward movement, rotation, standing, etc. Also, sensors detect the posture of the children and appropriate assist forces are applied by the cable-actuated brace worn by the child.

In embodiments, a CDPW includes a mobile base, a cable-actuation support system, and a control box. The mobile base may employ ordinary and caster wheels to move on a floor. Wheels may be powered by motors so that the walker can follow along with the child. The mobile base may have an open front to promote interaction with a caregiver or peers. The cable actuation is the interface between the walker and the child, attached to the child's pelvis using an adapter, for example a belt with cable connectors and closed with Velcro. The cables are configured to apply assist-forces on the child's body. The adapter may also be connected to tension sensors in order to indicate interaction forces between the adapter and a frame of the CDPW. The controller may be housed in a module attached to the frame and may include power, electronics for actuators, computations, real-time data acquisition and control. The CDPW may employ multiple cables, each connected to a cable actuator, for example a motorized winch, attached to frame. The frame may be configured to allow the number and the locations of cable routing points to be altered for each application. The cable-actuation is able to apply traction and torque forces on the pelvis, in any combination of dimensions and about any combination of axes, by employing a suitable number and positioning of the routing points and cables, to assist in balance during gait.

Cables may also be used to move the legs by means of thigh and/or shank adapters, for example to propel the leg forward. Embodiments can exert selected forces and torques on the pelvis to generate perturbations, thereby to facilitate learning or study additional paradigms such as weight suspension/augmentation to help train a child. An advantage of a cable driven system is it's the low moving inertia which may increase the transparency of interaction between the human and robotic device. Transparency refers to the responsiveness of the system which depends on the system's ability to overcome frictional and inertial resistance. A test of transparency would be to set a controller in a mode where it merely tracks the voluntary movements of an attached subject, neither hindering nor assisting such that the subject feels as if there is nothing attached to the adapters at all. A control module may be mounted on the frame. The control module may contain electronics for data acquisition and control. Motor drive, emergency switches, computer, NI PXI box and sensor amplifiers may also be included in this control module. Certain functions of the control module may be made wireless to reduce weight of the frame and enhance usability, cost, or other aspects by incorporating in application software running in standard or custom host computer. Such a host may communicate wirelessly with a module on the frame.

This CDPW can help a child to learn how to walk. Using disclosed embodiments, a caregiver may choose a training mode according to the unique characteristics of the child being assisted. The parameters of the training mode can be chosen by a caregiver to facilitate assistance or training, depending on a child's physical status and performance. The latter may be stored in a treatment profile and updated based on a treatment log. With the DCPW, a child can practice over-ground walking and interact with the environment and peers. The device is also compatible with a treadmill. The CDPW frame may be sized to allow it to pass through standard doorways.

In a tested embodiment the system was configured to exert active six degrees-of-freedom force and torque on the pelvis. The same system made it possible to apply perturbations to the subject's body or weight compensation and/or augmentation. The configuration may be used for over ground training and also on treadmills. The tested configuration can provide body weight suspension, augmentation or support to the pelvis of a child needing rehabilitation or assistance. The tested configuration may permit a child to move around other children in the environment and interact with others in walker arrangements.

Figure 23A:
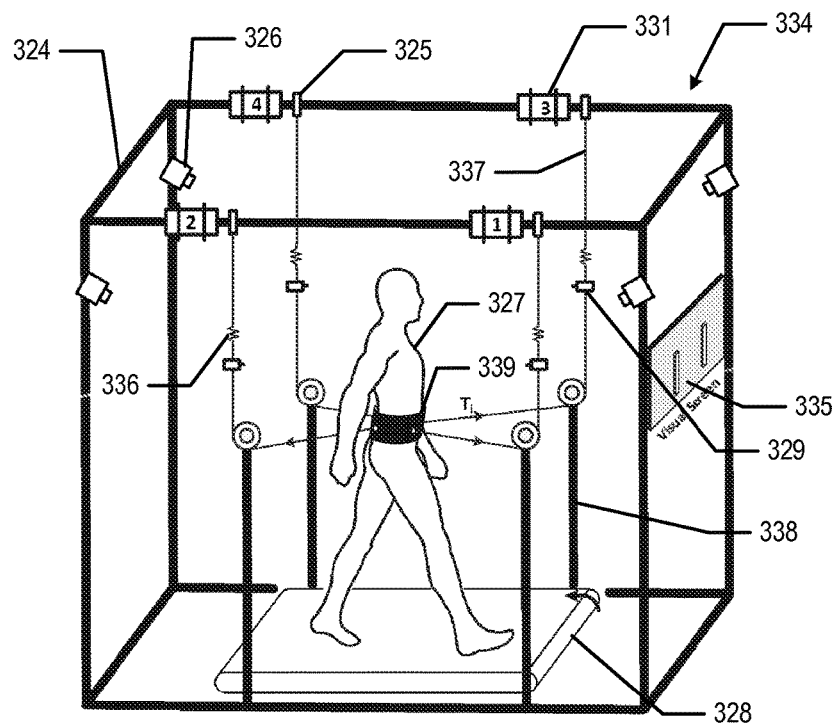
FIG. 23A shows an embodiment of an A-TPAD type apparatus according to embodiments of the disclosed subject matter which was used for certain tests of features for a pediatric walker CWPD embodiment.

Referring now to FIG. 23A, a test platform for testing the CDPW features includes a treadmill-based platform using a treadmill 328 on which a test subject 327 walks. A single phase servo motors with gearboxes, one of which is indicated at 331 (other motors with gearboxes, collectively, drives, are apparent from the drawing) are mounted on a fixed frame 324. Cables (one indicated at 337 but others are apparent from the drawing) were routed from the drives 331 via pulleys 325 and connected to a pelvis adapter 339 (a hip belt) worn by a test subject 327. Along each cable 337, a load cell 329 and a spring 336 (for example, of stiffness 2.5 N/mm) are arranged in series. Cameras 326 may be positioned on the frame 324 and video signals applied to a motion capture system with a classifier to indicate, in real time, subject body position/orientation, adapter position/orientation, sudden events such as a stumble, and other events or conditions. Four cables 337 with respective springs 336 and load cells 329 are illustrated. Not all elements are labeled with reference numerals, to avoid clutter, however they each should be apparent from the drawing and discussion.

Each cable 337 may apply a maximum continuous tension of 157 N. To track the cable attachment points and the human motion, a motion capture system was used during experiments. A real-time controller with Labview® (PXI 1082 from National Instrument, Austin) was used to implement the control strategy. A monitor 335 may be provided to give visual feedback to the subject 327, for example, it may graphically illustrate an error between a target position, orientation, velocity, and/or applied force during a current gait cycle in real time to help the subject follow the target gait characteristics. Cable guides 338 may be provided as needed to direct tension forces of the cables 337 along the directions required. The cable guides 338 may be adjustable.

Figure 21A:
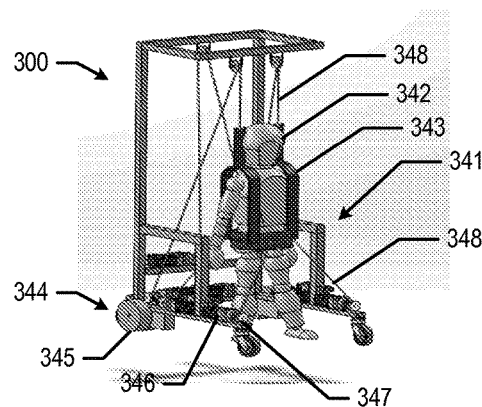
FIG. 21A shows a walking frame based embodiment which may, as illustrated, be suitable in size and power level for use by a child.

FIG. 21A shows a walking frame based CDPW embodiment which may, as illustrated, be suitable in size and power level for use by a child. In the illustration of FIG. 21A, an open frame 341 allows the child 342 to interact with people and things in the environment. In the configuration shown, a harness 343 supports the child 342 and transmits moment, traction, support, and/or downward forces and perturbations (applied through cables 348) during controlled sessions according to programmed instructions stored in one or more control modules 344. Passive or motorized wheels that are also controlled by the control module 345 may be provided. Cable tension may be controlled by respective winches including motors 346 and pulleys 347 (in combination, drives). Note that not all like-elements are labeled with reference numerals to avoid clutter, but it is clear from the description and drawing that multiple instances of these elements are present. Note that in-use, the harness 343 will be tightened around the body to ensure against backlash and to provide good feedback to the controller which receives the signals from the sensors (including force sensors). Although not shown in this drawing, cameras (e.g., as 326) and motion and event capture and classification may be provided through the control module 345.

FIG. 15B shows a controller 350 for the movement training apparatus 299 that may be used for the leg actuators 300 and the trolley platform 102 as well as any the A-TPAD and CDPW embodiments. The controller 360 has a processor 410 with data storage that may include non-volatile data storage and random access memory elements (Stor.). Further it may have a data acquisition portion (DAQ) that interfaces to sensors for receiving signals from the various sensors of the described embodiments. It may have output components such as audio and video adapters as well as input interfaces to support interaction with one or more subject interface (UI) elements 354. It may have a digital to analog converters (D-A) for output signals to final controllers 358 that drive motors. It may have a processing unit (CPU) for numerical computation and execution of programmatic instructions. Apart from the data storage, it may be connected to data sources including databases, for example a patient database 356 with patient profiles such as the patient's particular limb lengths, diameters, strength and weakness parameters, etc. that are useful for fitting and controlling rehabilitation using the movement training apparatus 299.

Figure 23B:
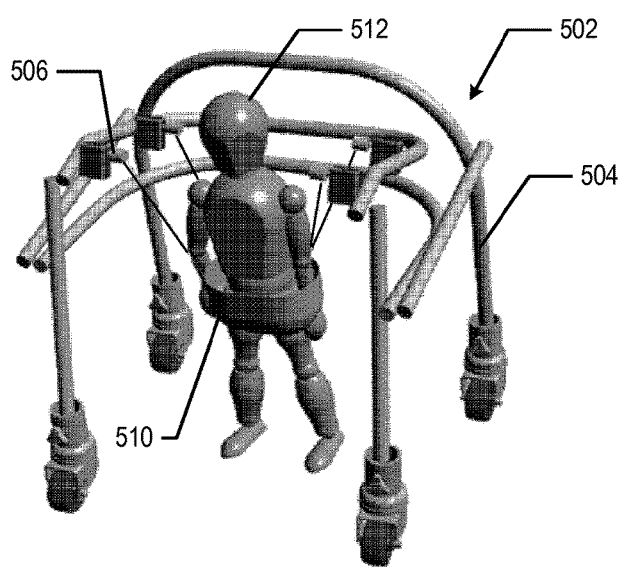
FIG. 23B shows an embodiment of a CPWD apparatus according to embodiments of the disclosed subject matter.

FIG. 23B shows a figurative embodiment of a CPWD apparatus 502. Such devices may be configured by affixing winches 506 to available pediatric walker frames 504 as illustrated in FIG. 12B since passive walkers are readily available and inexpensive. The winches 56 may then be attached to a harness or belt 510 for supporting, challenging (e.g. perturbing), and or assisting a pediatric subject 512. FIG. 24 is a processed photograph of a tested embodiment of a CPWD showing an adult test subject in position with respect to it, according to embodiments of the disclosed subject matter. It is much larger than a pediatric walker based system as it was used for evaluation by adult test subjects.

Figure 23C:
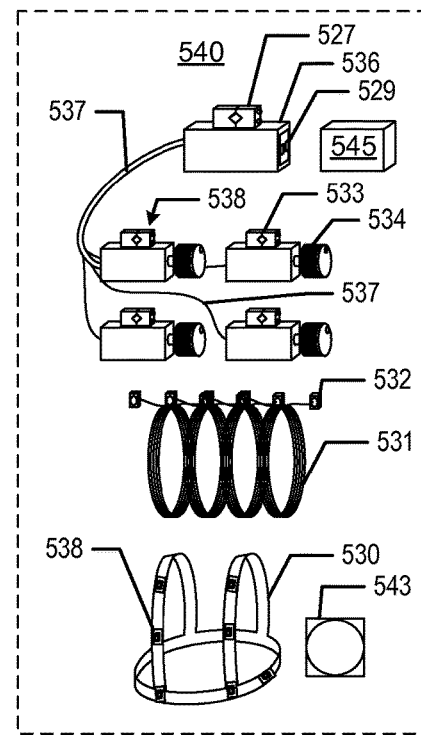
FIG. 23C shows a kit for adapting an off-the-shelf pediatric walker to an active system according to various A-TPAD embodiments and further embodiments according to the disclosed subject matter.

FIG. 23C shows a kit 540 for adapting an off-the-shelf pediatric walker (e.g., 502) to an active system according to various A-TPAD embodiments and further embodiments according to the disclosed subject matter. A controller 536 has an adjustable universal mounting bracket 527 for securing the controller 536 to a tube of a pediatric walker. The controller has a wiring loom 537 with multiconductor quick connectors (not shown) to connect the loom 537 with the controller 536 and winches 538 for supply of power and transmission of control and feedback signals from encoders incorporated in the motors (e.g, if the motors are servo motors). The winches 538 may also have adjustable universal mounting brackets 533. The controller 536 may also have a battery 545 to drive the motors and power the controller itself. The battery 545 may be connectable and interchangeable with the controller 536 through an electrical and mechanical interface 529. The pulleys 534 of the winches 538 may have securements for respective cables 531. The cables 531 may have fasteners 532 to connection to selectable connectors 538 on a harness 530. Software for a separate host processor that communicates with the controller 536 may be provided on a computer readable medium 543 along with instruction for setting up a CPWD according to the embodiments.

Figure 21B:
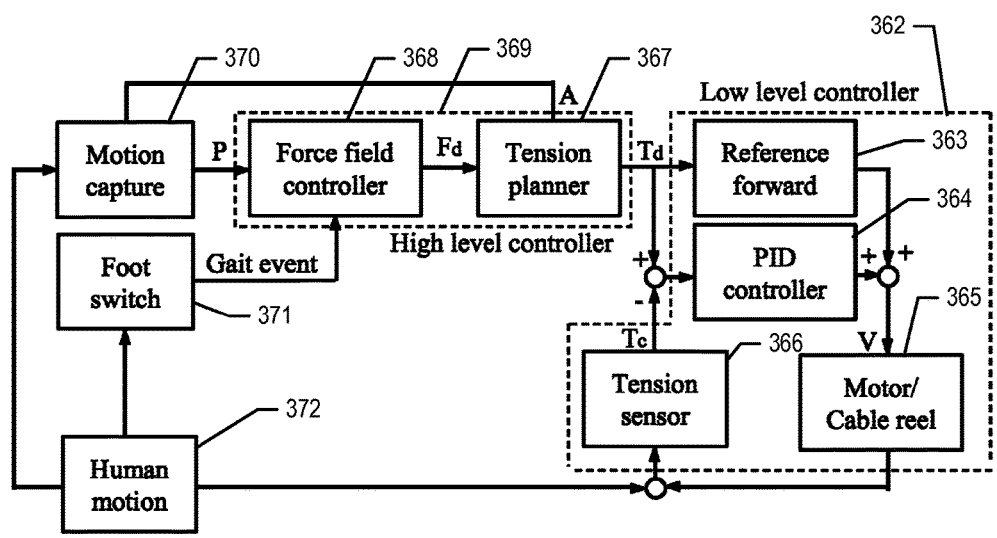
FIG. 21B shows functional aspects of a controller for the apparatus of FIG. 21A and similar devices.

FIG. 21B shows functional aspects of a controller embodied at least partly by software and firmware in the controller to form, in embodiments, an assist-as-needed (AAN) controller. A low level controller 362 includes a closed loop PID controller based feedback term 364 and a feed-forward term 363 proportional to the selected tension provided by a tension planner 367. This part of the controller may operate at 1000 Hz as an embodiment that was tested. Output of the feedforward and feedback control are applied to final controllers that regulate tension in the winches (motor/cable reel) 365. Tension feedback is applied to the feedback controller 364 from tension sensors 366. The high level controller 369 includes the AAN controller to follow a selected pelvic trajectory generated by force field controller 368 in response to inputs from motion capture component 370 and signals from a gait event detector 371, in the tested embodiment, a foot switch that is actuated by human motion. In embodiments, the motion capture can classify the gait events alternatively, or probabilistically in combination with a motion gait event detector 371. All components of the high level controller were executed at 200 Hz and are further described in the following sections.

Force field controller 368 may create a virtual force tunnel along the target trajectory in transverse plane based on the pelvic center. A pelvic center may be derived from the motion capture system by computing the centroid of left and right iliac crest markers which may be integrated on the hip adapter or harness. The markers need not be separate depending on the motion capture software being used, for example, a single marker that indicates angle may be used in combination with markers or features that an image classifier could use to estimate the separation distance and positions of the iliac crests or other anatomical features. The controller may be configured such that if the pelvic center is outside the force tunnel, forces are applied on the pelvic center to provide guidance toward the target trajectory. This force $F_d$ may be taken a combination of normal force ($F_n$) to the target trajectory and a damping force ($F_c$) in the transverse plane.

$$F_d = F_n \pm F_c \quad (37)$$

Let P be the current position of the pelvic center and N be the closest point to P on the target trajectory (see FIG. 3). The direction of the normal force, denoted as $\vec{n}$, is a vector from P to N which is normal to the target trajectory. The magnitude of this force is obtained by the distance d between current position of pelvic center (P) and its nearest point (N) on the target trajectory. As the subject deviates further away normal to the tunnel, a larger guidance force $F_n$ is exerted on the pelvis.

$$F_n = K_n \left( 1 - e^{\left(\frac{d}{D}\right)^2} \right) \vec{n} \quad (38)$$

The damping force $F_c$ is added in the force field to avoid oscillations inside the tunnel. The direction of this damping force is also along the normal vector $\vec{n}$ and its magnitude is proportional to the velocity of the pelvic center $\vec{v}$.

$$F_c = -K_c (\vec{v} \cdot \vec{n}) \vec{n} \quad (39)$$

In experiments, the parameters used in the controller were: $K_n$=30 N, D=0.125 m, and $K_c$=3. During the experiment, the force field was gradually increased for the first one minute to avoid instability of subjects at the start of training. Pelvic movement is characterized as a combination of global translational movement and local periodic movement. As this force field changes periodic pelvic movement while global movement of the pelvis was compensated by refreshing the force field at every right heel strike, detected in the experiment by a foot switch.

In the current work, four cables were connected to the hip belt to apply the selected force profile in the transverse plane, as shown in FIG. 1. If $T \in \Re^{4 \times 1}$ represents the tension in each cable, then the force-moment vector $F \in \Re^{6 \times 1}$ applied at the pelvic center can be obtained using the following expression.

$$AT = F$$

$$\text{for } F = [F_x F_y F_z M_x M_y M_z]^T \quad (40)$$

A is 6×4 structure matrix, which is a function of the system geometry and can be computed from the coordinates of the cable attachment points. $F_x$ and $F_y$ are the guidance force $F_d = [F_{dx} F_{dy}]^T$ in the transverse plane computed by the force field controller. For the human experiment, a limit was placed on the three moment and vertical force components ($M_x$, $M_y$, $M_z$ and $F_z$ respectively). A quadratic programming based optimization scheme was implemented to solve Eq. (4).

$$\min f \quad (41)$$

$$f = \frac{1}{2}((T - T_p)^T(T - T_p))$$

$$\text{s.t. } F_x = F_{dx}; F_y = F_{dy}$$

$$-10 < F_z < 10(N)$$

$$-5 < M_{x,y,z} < 5(Nm)$$

$$T_{min} < T < T_{max}$$

In the above equation, $T_p$ is a positive constant added to the objective function to ensure non-zero cable tension values. $T_{min}$ (10 N) and $T_{max}$ (50 N) are the lower and upper bounds on the cable tension values.

Figure 22A:
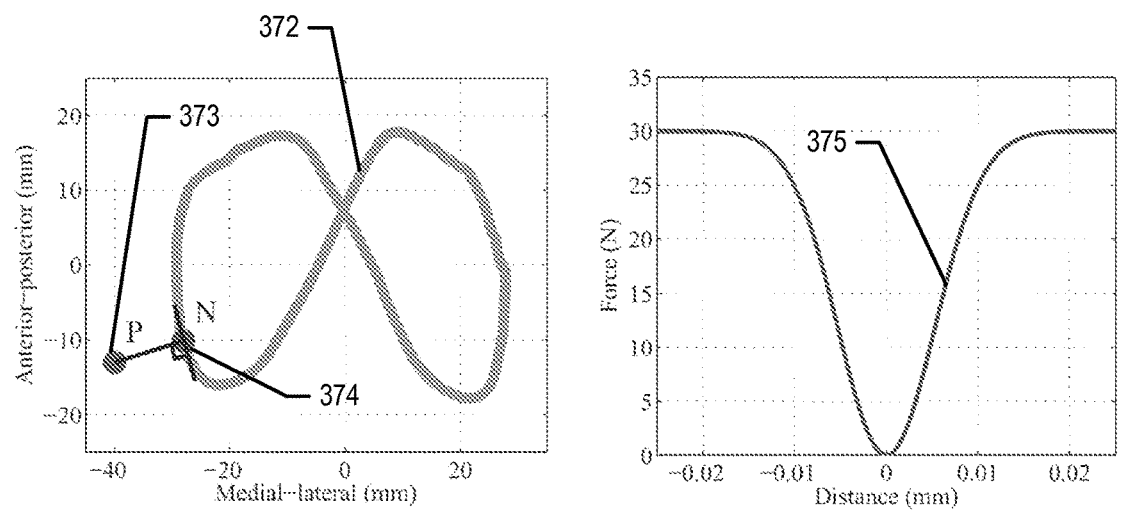
FIG. 22A presents a scheme for visual feedback according to embodiments of the disclosed subject matter.

FIG. 22A presents a scheme for visual feedback according to embodiments of the disclosed subject matter. On the left side, a target trajectory 372 is shown with a current pelvic center point (P) 373 and a nearest point (N) 374. A force profile of normal force $F_n$ is indicated at 375. The constant parameters used for the force field were $K_n$=30 N and D=0.125 m.

The experimental methods and results are described presently. Seven healthy male subjects (age range: 25-34 yrs; mean weight: 72 kg) participated in the study. Each subject wore a hip belt with cable attachment points, reflective markers and shoes with pressure pads. To provide the force and visual feedback, a target pelvic trajectory in the transverse plane was created from the baseline pelvic motion data of each subject. For the target trajectory, the pelvic range of motion in the medial-lateral direction was extended by 40%, and the pelvic range of motion in the anterior-posterior direction was kept the same as baseline.

The baseline pelvic data was high pass filtered, at a cut off frequency of 0.4 Hz, to remove the low frequency components, such as body translation over the treadmill platform. The filtered data was divided into gait cycles and the average of ten gait cycles was used to generate the target trajectory. In addition, as shown in FIG. 22A, visual feedback was provided to each subject, where the target pelvic trajectory 372 was displayed as a green solid line on a monitor with a red dot 373 showing the current pelvic position of the subject. The closest point 374 on the target trajectory with respect to the current pelvic center was also displayed using a blue dot. Subjects were instructed to follow the target pelvic trajectory and were made aware of the applied force feedback at their pelvis.

During the experiment, all subjects walked at constant treadmill speed of 3.8 km/h. The experimental protocol consisted of three sessions: Baseline (BL), Training (TR) and Post-training (PT).

During the BL session, subjects were asked to walk for four minutes to record the subjects' walking pattern. Data collected in the last minute of this session was used as reference in the analysis. During the TR session, cables were attached to the hip belt to provide the force feedback while the subjects walked on the treadmill for twenty five minutes. Visual feedback that showed the current pelvic position with respect to the modified pelvic trajectory was provided throughout the training session. Subjects were instructed to follow the modified pelvic trajectory. During the PT session, the cables were detached from the hip belt and subjects were asked to walk for another nine minutes. Visual feedback was also switched off during this session. Data were collected at the start, 2nd, 6th, 8th minute and are referred to PT1, PT2, PT3, PT4.

The data from markers were analyzed offline to extract the spatiotemporal gait parameters. Gait events, such as heel strike and toe off, were calculated from the sacrum, heel, and toe markers of each leg. A gait cycle was defined from a right heel strike to the following right heel strike. All data sets were divided in gait cycles using the gait events and time normalized to 100% gait cycle.

Range of motion (ROM) of the pelvic center was calculated for each gait cycle in both the anterior-posterior (Y axis) and medial-lateral (X axis) directions. Step width was defined as the maximum medial-lateral distance between the right and left fifth metatarsal foot markers during the double support period after right heel strike. Step length for a leg was defined as the anterior-posterior distance between the heel markers of two legs at that leg's heel strike instant. These values were normalized with each subject's height. Lower limb joint angles such as hip, knee, and ankle rotations were also calculated from the marker data. To verify whether the subjects can adapt to extended target pelvic trajectory, difference between the target and actual pelvic lateral ROM was calculated during each gait cycle, and is referred to error of lateral motion in the following sections.

For each subject, the last 10 gait cycles of trials BL, PT2, PT3, and PT4 were used to evaluate the subjects' performance. Post-training PT1 is not included, as PT1 was measured before the subject's gait reached steady-state after the initiation of gait cycles. All data sets were averaged across these gait cycle to calculate the representative value for each trial. For the statistical analysis, non-parametric repeated measure using the Friedman's ANOVA was performed on the group data. The significance level was defined at 0.05. In case of significant difference, Wilcoxon signed rank test with Bonferroni corrections was used for the pairwise comparison.

Figure 22B:
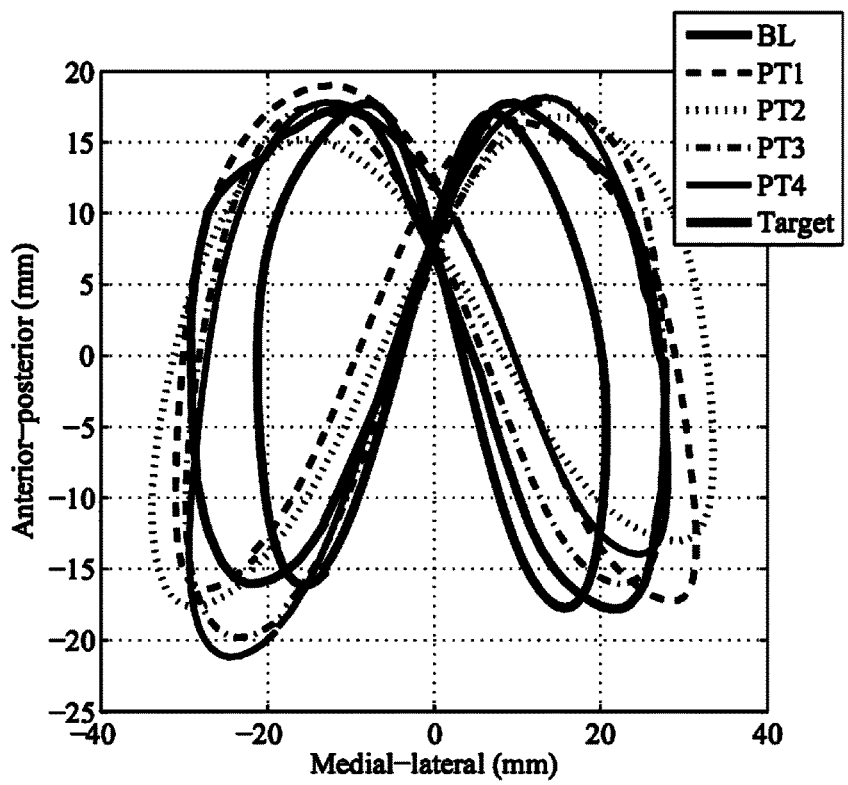
FIG. 22B shows the pelvic trajectory of baseline (BL) and post-trainings (PT) in transverse plane for a representative subject.

FIG. 22B shows the pelvic trajectory of baseline (BL) and post-trainings (PT) in transverse plane for a representative subject. The target pelvic trajectory used during the training session, shown by the solid line, has 40% longer medial-lateral span (about 1.6 cm) than the baseline pelvic trajectory. It was observed that the subject retained the extended pelvic motion during the post-training trials. The error between the target and actual pelvic trajectory lateral range of motion is presented in FIG. 22C. The non-parametric repeated measure test reported significant changes in the error values (p 0.005). The post-hoc pairwise analysis reported significant changes in the error values between the baseline (BL) values and the post-training values (PT2, PT3 and PT4). Subjects were able to retain the extended pelvic motion during 9 minutes after training. Error is computed as the difference between the target and actual pelvic trajectory lateral ROM. PT2, PT3, and PT4 values were significantly decreased compared to BL values. This shows that subjects modified their pelvic trajectory to adapt the target trajectory.

Figure 22C:
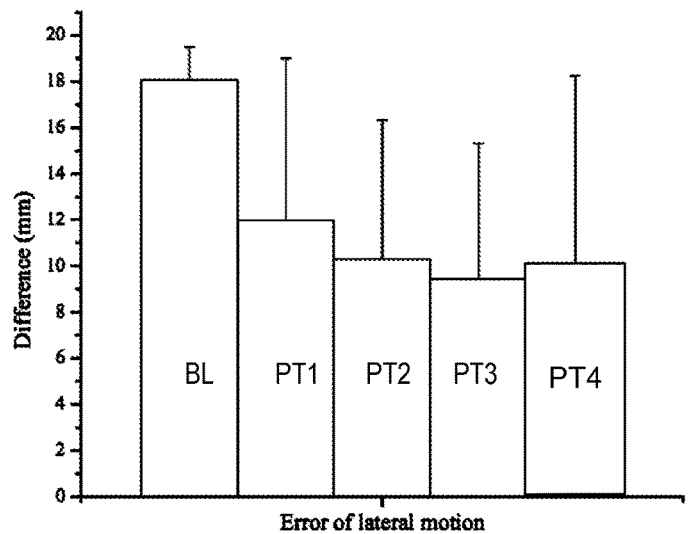
FIG. 22C shows error of lateral motion for baseline (BL) and post-training (PT) in tests of embodiments of the disclosed subject matter.

Anterior-posterior values were significantly higher than the BL values during PT3 and PT4 trails. To observe how subjects adapt to the target trajectory, gait parameters and lower limb kinematics were also analyzed. Same statistical analysis was run for all these parameters. FIG. 22C shows the medial-lateral and the anterior-posterior pelvic range of motion for baseline (BL) and post-training (PT). Medial-lateral range of motion was significantly higher during the post-training trials. A significant effect of the training was observed in the medial-lateral values (p 0.000). The medial-lateral pelvic range of motion values were significantly higher during the post-training trials (PT2 to PT4) compared to the baseline values. In addition, significant changes in the anterior-posterior pelvic range of motion values were also reported over the group (p 0.005). The post-hoc analysis reported significantly larger anterior-posterior pelvic range of motion values during the trials PT3 and PT4 compared to the BL values. However, the increase of anterior-posterior pelvic range of motion was not always observed in all subjects' pelvic trajectory.

Figure 22D:
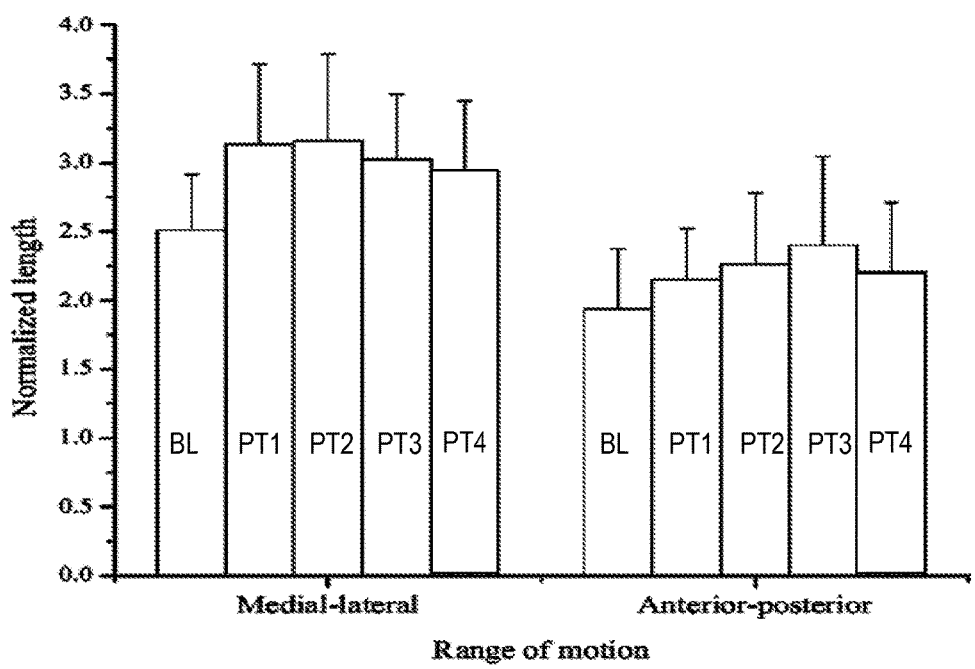
FIG. 22D shows medial-lateral and anterior-posterior pelvic range of motion for baseline (BL) and post-training (PT) resulting in tests of embodiments of the disclosed subject matter.
Figure 22E:
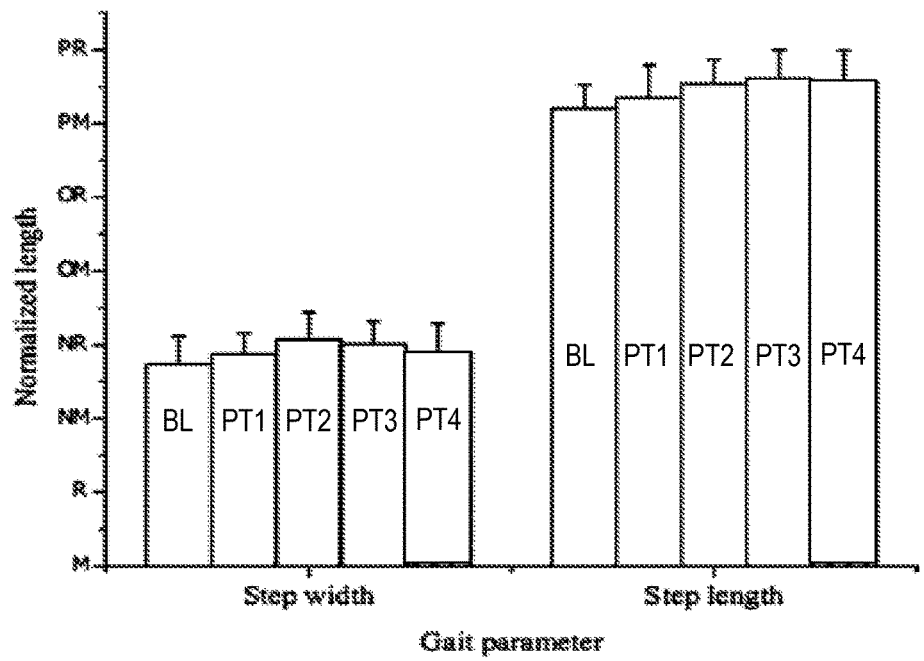
FIG. 22E shows average step width and length values in tests of embodiments of the disclosed subject matter.
Figure 22F:
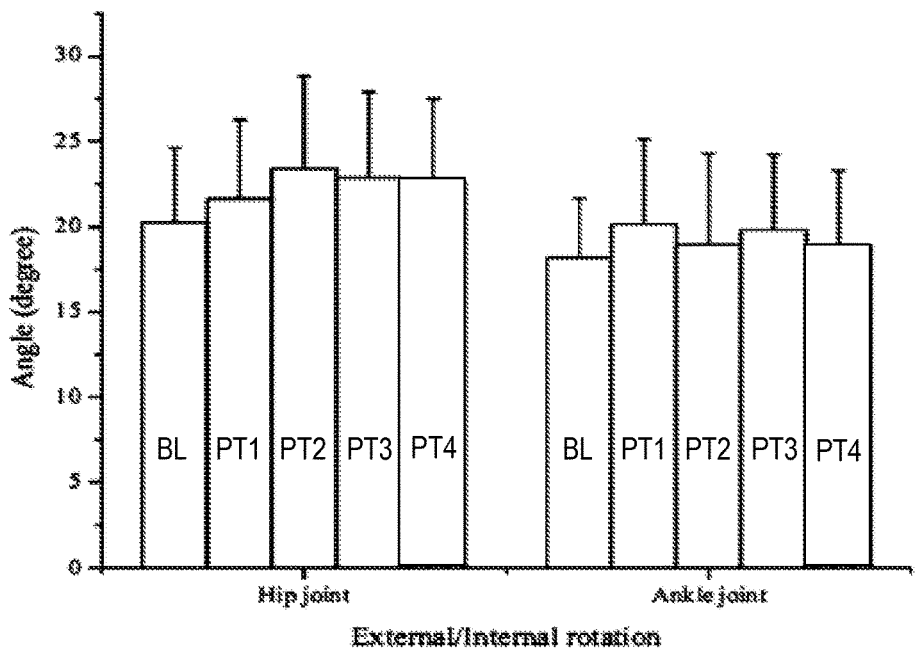
FIG. 22F shows range of motion for internal-external rotation of the hip joint and the ankle joint in tests of embodiments of the disclosed subject matter.

The average step width and step length values are shown in FIG. 22D for the group during the baseline and post-training trials. The Friedman's test reported significant effect of the training on the group's step width values (p 0.05), but the pairwise analyses did not report any significant changes in the selected pairs. In addition, significant changes were also reported in the step length values for the subject group (p 0.005). The step length was reported to be significantly higher during the post-training trials (PT3 and PT4) compared to the BL values. Range of motion for the hip and ankle joints for post-training trials increased compared with the baseline data (FIG. 22E). Hip joint did not show significant change, but ankle joint indicated significant changes from Friedman's test (p 0.05). No significance was found in the pairwise comparisons for the hip and ankle rotation. Step width showed significant changes but no pairwise significance was reported. The step length values were reported to be significantly higher than the baseline values during the post-training trials (PT3 and PT4).

FIG. 22E shows range of motion for internal-external rotation of the hip joint and the ankle joint. Both hip and ankle joint values reported increasing trends, but significant changes were observed only for ankle values. For pairwise comparison, no significance was observed. In this experiment, a target trajectory was created with extended lateral motion to demonstrate this. Experimental results showed that the error between the target and actual pelvic trajectory reduced after the training. Subjects adapted and retained the target trajectory nine minutes after the training. Additionally, subjects also changed the lower limb kinematics to adapt to the new target trajectory.

To be able to walk with the changed pelvic trajectory, subjects changed the foot placement. In order to extend the pelvic trajectory, subjects widened their feet to increase base of support. To achieve stability, the vertical projection of the center of mass should be within the base of support. Laterally extended pelvic trajectory resulted in the increased step width to maintain stability. In addition to the step width, interior-exterior ankle and hip rotations increased. By this change, it is likely that subjects further extended the lateral base of support to adapt to the new pelvic trajectory. Some subjects increased the step length to enlarge the base of support in anterior-posterior direction.

The goal of the assist-as-needed control strategy for the pelvic trajectory is to train patients who have abnormal pelvic motion. Stroke patients with abnormal lateral pelvic range of motion are reported to consume higher metabolic cost than age matched control group. Training to reduce excessive pelvic motion is expected to restore energy-efficient gait cycle. In addition, elderly or stroke patients with high variability in lateral pelvic displacement can also benefit from this control strategy. High variability in lateral pelvic displacement causes falls and injuries when the center of mass deviates outside the base of support. This control strategy can train subjects to keep their pelvic trajectory within the base of support for stable and balanced gait.

One limitation of the proposed control strategy is that the forces were only exerted to correct the transverse plane pelvic motion. Vertical pelvic motion also plays an important role, as 50% of the total work for walking is required for lifting the body to reach maximum vertical motion during single limb support. Especially, cerebral palsy children have been observed with 60% greater vertical excursion due to spastic response in triceps surae muscles and tight hamstring muscles. Thus, three dimensional assist-as-needed controller can be beneficial to patients who need guidance in either horizontal or vertical pelvic trajectory. In the near future, this proposed controller will be extended to provide three dimensional guidance force by creating a fully spatial force field tunnel.

The disclosed embodiments include an assist-as-needed force control strategy to guide and change the pelvic trajectory in the transverse plane. Preliminary study of seven subjects showed the following results: Subjects adapted to a new pelvic trajectory and retained it for nine minutes after the training. Subjects were also able to walk with the guidance forces applied on the pelvis without losing balance. Kinematics of lower limb changed according to the altered pelvis trajectory to keep balance while walking. This proposed assist-as-needed control strategy is able to guide and change pelvic trajectory. Also, this result suggests that such a strategy can be investigated to correct abnormal pelvic trajectory in patient population to achieve energy efficient and balanced gait. In future, studies will be conducted to verify this with patient groups with abnormal pelvic movement.

In any of the embodiments, including those defined by the claims, instead of cables, the embodiments may be actuated with belts, chains, or other similar types of elements. Further, any sliding connections may be replaced with rolling mechanisms such as idler pulleys to function as guides for cables, belts, etc.

Figure 26A:
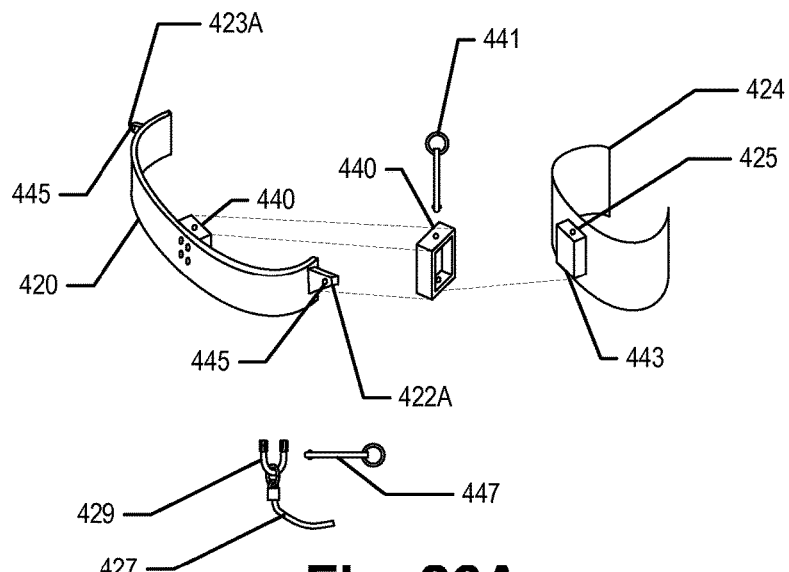
FIG. 26A shows a quick-connectable limb adapter for use with any of the embodiments of the disclosed subject matter.

FIG. 26A shows a quick-connectable limb adapter for use with any of the embodiments of the disclosed subject matter. A lever mount 420 may be for a thigh or shank adapter (or for any other limbs or body parts such as upper and lower arm). A quick release capture well 440 receives a boss 443 integrated or attached to a cuff 424 and locks it into place with a grenade pin 442. The capture well 440 is secured to the lever mount 420. Cable 427 ends can be releasably shackled by means of shackles 429 and grenade pins 447 to extensions 422A and 423A which have holes 445 for receiving the grenade pins 447. A method of using the components of FIG. 26A with any of the embodiments herein is to secure a custom cuff 424 to a subject before connecting the subject to the cable-actuated system. After the subject has been secured to the cuffs, the cuffs can be quickly connected to the lever mounts 420, thereby saving down time between subjects. In addition, the cuffs 424 may be custom-made by an orthosis specialist for each subject. Note that a closure (such as a Velcro belt) for the cuff 424 is omitted but may be provided as in other embodiments.

Figure 26B:
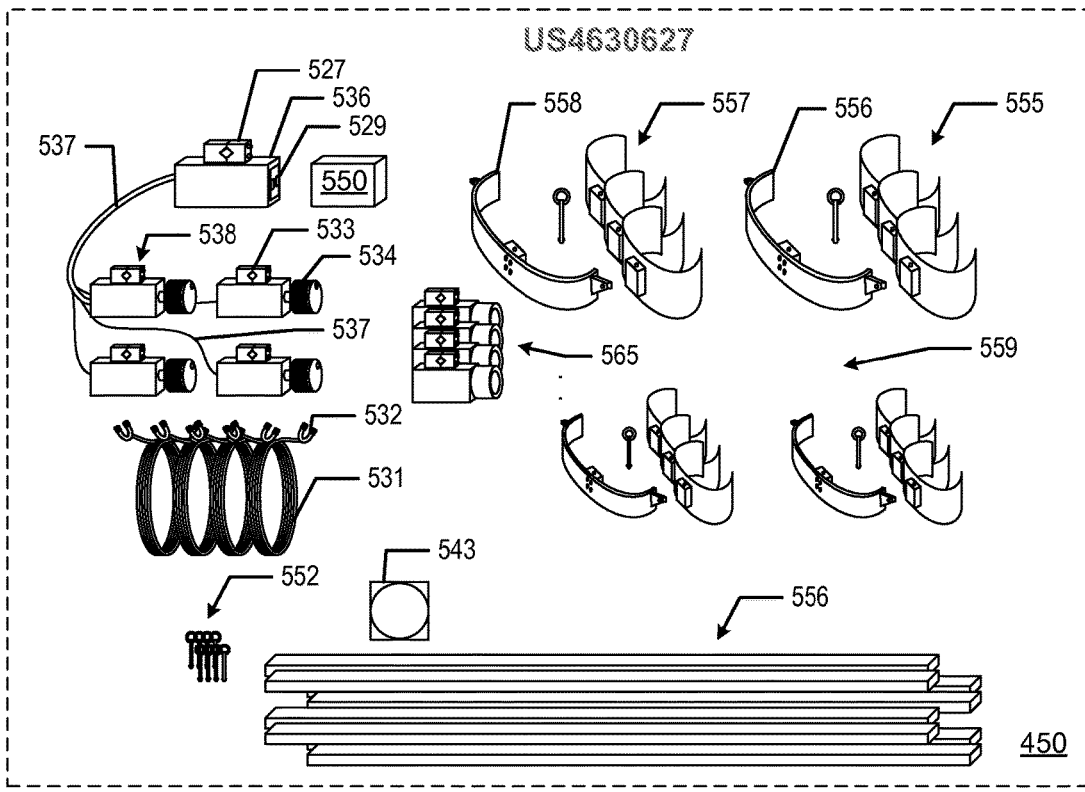
FIG. 26B shows a shippable package to allow a cable-actuated system to be transported and set up for use in homes, clinics, or other locations for implementing any of the disclosed embodiments.

FIG. 26B shows a shippable package 450 to allow the set up and use of a cable-actuated system in desired locations. The package 450 can be transported and set up for use in homes, clinics, or other locations for implementing any of the disclosed embodiments. The package may include lever mounts 556, 558, various cuffs 555, 557 of different sizes or customizable by an orthotist with suitable quick connector hardware as described with reference to FIG. 26A. Additional limb adapters 559 may be provided for arms, legs, hips, or other body parts (e.g., child harness). Cables 531 may be provided of suitable length and connectable to winches 538 as described with reference to FIG. 23C. Grenade pins may be provided for shackling the cables to the lever mounts as also described above. Modular frame elements 556 such as extruded channels with locking hardware that can be used to erect a frame to support the winches and cameras 565 (for a motion capture) and the controller 536 may be provided. Other elements described with reference to FIG. 23C are as previously described. The controller 536 may have motion capture processor with a suitable wiring loom and relevant connectors for rapid deployment. Although the foregoing embodiments were described with certain kinds of connectors such as grenade pins, shackles, etc., it is understood that these can be replaced with any type of suitable connector to provide alternative embodiments. Also, instead of a set of module frame elements 556, a collapsible pre-connected frame may be provided that can be set up like a pop-up or collapsible tent frame, for example as described in U.S. Pat. No. 4,630,627, hereby incorporated by reference as if fully set forth in its entirety herein.

Figure 27A:
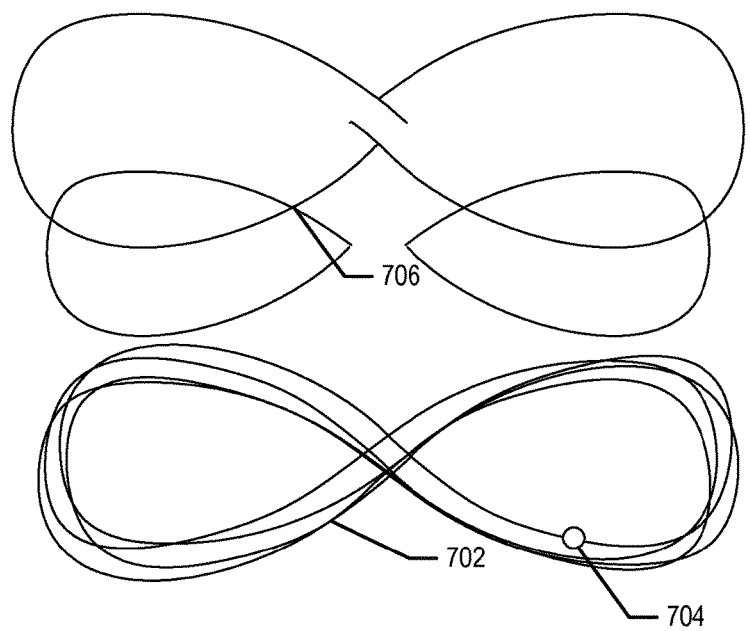
FIGS. 27A and 27B shows visual feedback animations for gait training systems that provide feedback relating to hip motion or other centers of motion, according to embodiments of the disclosed subject matter.
Figure 27B:
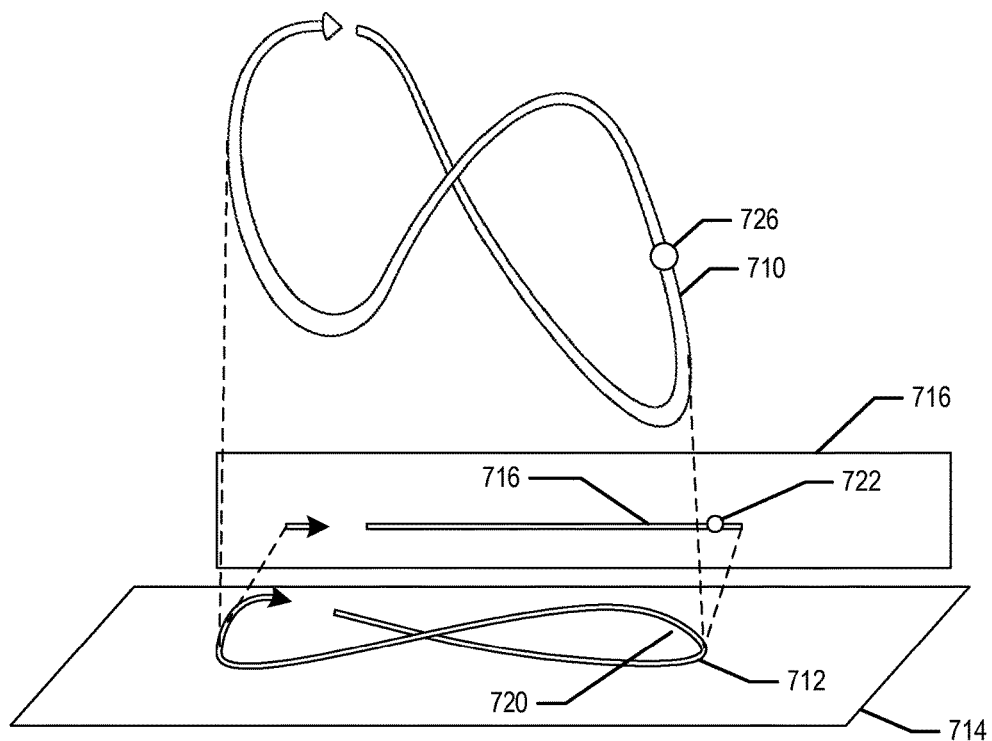

FIGS. 27A and 27B shows visual feedback animations for gait training systems that provide feedback relating to hip motion or other centers of motion, according to embodiments of the disclosed subject matter. A monitor may be placed in front of a user of A-TPAD and CPDW embodiments and used for showing hip motion-related feedback to the user as indicated in connection with the embodiments disclosed. A control method may provide a force tunnel approach described herein for urging a subject to follow a target hip trajectory stored in the controller that controls the cable actuators of the embodiments. The force tunnel may be displayed as two-dimensional projection on a plane as indicated at 706. The force tunnel is progressive, so a color or luminance gradient may used to show the force-ramp. Alternatively, a center line may be shown as opposed to a defined error-band as indicated at 706. Superimposed on the projection of the force tunnel may be a trace 702 of the actual measured hip trajectory as captured by a motion capture system such as the camera-based systems identified herein. A current tracer 704 may be shown on the screen as part of an animation. The tail end of the trace 702 may disappear after a certain length. Multiple cycles of the trace 702 may be shown to provide positive feedback to the subject when the subject is successful at staying with in the force tunnel but may be shortened or elongated responsively to the degree of success staying inside the force tunnel.

Figure 28:
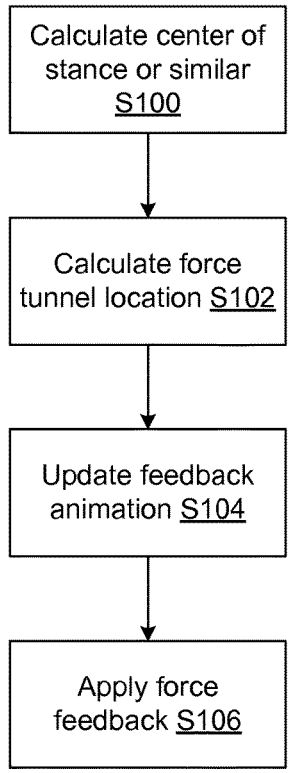
FIG. 28 shows a flow diagram for a process for maintaining the feedback animation and controlling a force tunnel according to embodiments of the disclosed subject matter.
Figure 29:
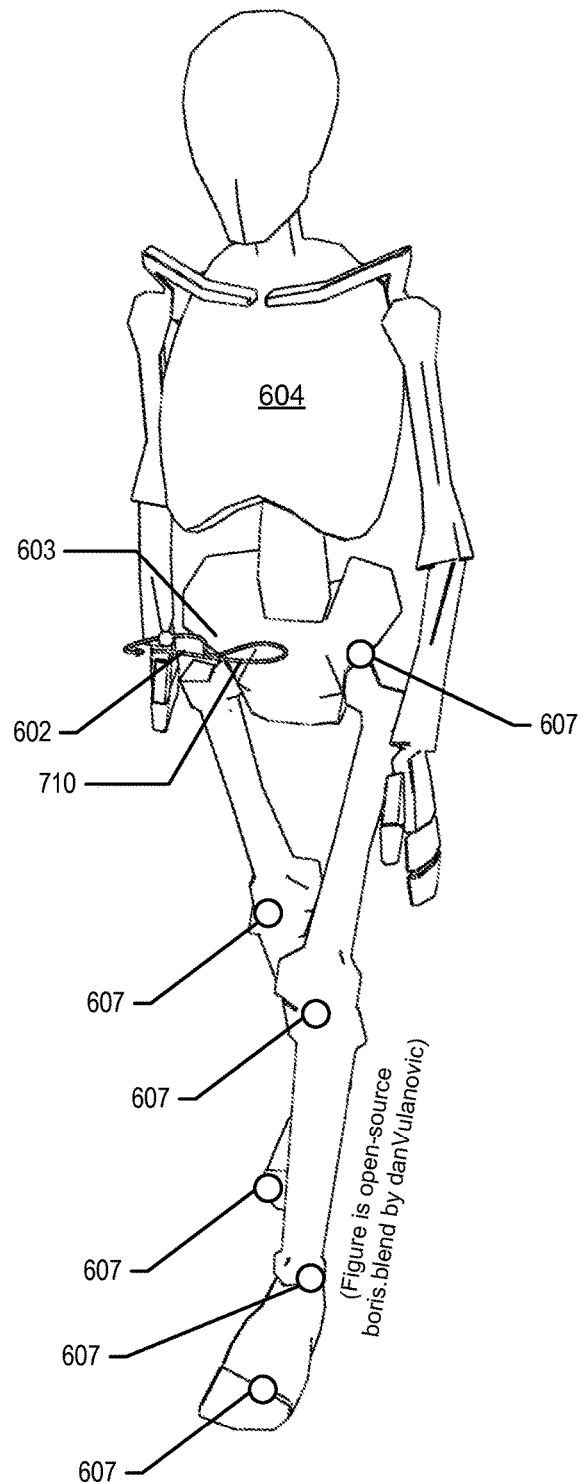
FIG. 29 is a perspective figurative view of a hip trajectory and motion capture markers on a simplified walking skeleton for discussing control and feedback animations in relation to hip control features of the embodiments.

FIG. 28 shows a flow diagram for a process for maintaining the feedback animation and controlling a force tunnel according to embodiments of the disclosed subject matter. The motion of the legs and/or parts thereof (e.g., joints) can provide the cable controller with sufficient information to determine the extent to which motion in the tracked point of the hip is due to the gait or caused by the general course of the walking subject. For example, treadmill walkers tend to wander from side to side as well as slow down and speed up causing the center of their stance to wander around. These motions may be subtracted as background movement so that the tracking of the hip, and the synthesis of the force tunnel, does not include this part of the overall position signal of the tracked body part. FIG. 29 is a perspective figurative view of a hip trajectory and motion capture markers on a simplified walking skeleton for discussing control and feedback animations in relation to hip control features of the embodiments. Motion capture marker 603 may correspond to a marked point on the hip that is tracked by the controller and subjected to force tunnel guidance. The point that is tracked may also be the trace point that is shown in the feedback animation. The point for force tunnel guidance and for feedback trace may alternatively be a virtual point whose position is extracted from the positions of multiple markers. A three-dimensional trace 602 of the tracked point 603 is shown in 3-space adjacent a walking subject (shown as a modified skeleton) in the drawing, although its size may be exaggerated for clarity. At S100 a location of the pelvis with respect to which the force tunnel and animation are based is extracted from the motion tracking system. At S102 and S104, the force tunnel position and feedback animation position base are compensated responsively to output from S100. The feedback and force tunnel are generated based on the compensated data. These steps may be carried out on a host computer or an embedded processor connected to or incorporated in the controller. The feedback components can be bundled with the package 450 or 540. The three dimensional trace of a point 726 on the hip may take the form of a warped figure-8 as indicated in FIG. 27B at 710. The planar projection of the trace 712 may provide the basis for the animation 714 of FIG. 27A. A projection of the planar projection may form the basis of an alternative or additional display 716 which shows a wandering point 722 on a linear trace 716. Different planes may be added to show different traces or alternatives. For example, a projection onto a plane normal to the Z axis may be shown with a projection onto a plane normal to the Y and X axes, or an oblique plane.

According to first embodiments, the disclosed subject matter includes a cable driven exoskeleton system. A cable drive mechanism is connected to drive a plurality of cables. A shank adapter is configured to be positioned on the shank of the leg of a subject, the shank adapter having extensions for attachment of respective ones of the plurality of cables therefrom, the shank adapter extensions holding the cables in a position away from a knee so that the cables are not in contact with the knee or other parts of the leg and such that selective moments are applied to the shank responsively to tension in the respective ones of the plurality of cables. Tensions applied to the plurality of cables are determined by a cable tension controller configured to control the cable drive mechanism. A thigh adapter is configured to be positioned on the thigh of the subject, the shank adapter having extensions for attachment of respective ones of the plurality of cables therefrom, the thigh adapter extensions holding the cables in a position away from a knee so that the cables are not in contact with the knee or other parts of the leg and such that selective moments are applied to the thigh responsively to tension applied by the cable tension controller. Tension sensors are configured to generate sensor data indicating angles of movement of the thighs and shanks of the subject during walking. The cable tension controller is configured to compute a computed gait trajectory responsive to the sensor data. The cable tension controller is further configured to the computed gait trajectory with a predefined trajectory and to calculate command data for commanding selected respective tensions in the plurality of cables responsive to the comparison. The cable tension controller is programmed to control the plurality of cables to achieve the selected tension in each cable to generate torques in the shank and thigh toward the predefined trajectory. the tension of the plurality of cables is converted to moments by the joints of the subject without support of external joints.

The first embodiments can be modified to form further first embodiments in which the cable tension controller further calculates a level of assistance to be applied to the body part. The first embodiments can be modified to form further first embodiments in which the thigh adapter has extensions for sliding engagement ones of the plurality of cables such that tension in the ones generates a moment about the joint to flex or extend the knee. The first embodiments can be modified to form further first embodiments in which the cable drive mechanism includes motorized winches, each of which controls an angular position of a pulley to control the tension in a respective one of the plurality of cables. The first embodiments can be modified to form further first embodiments in which the motorized winches are attached to a hip adapter that is supported on the hips of the subject. The first embodiments can be modified to form further first embodiments in which the hip adapter wraps about the subject hip and waist and closes as a belt. The first embodiments can be modified to form further first embodiments in which the hip adapter is connected to other ones of the cables and the cable tension controller is programmed to apply predefined wrenches to the hip adapter. The first embodiments can be modified to form further first embodiments in which the predefined trajectory is based on a characteristic of a human gait. The first embodiments can be modified to form further first embodiments in which the thigh and shank adapters include cuffs that wrap around the respective body part. The first embodiments can be modified to form further first embodiments in which the adapter extensions position each of the plurality of cables such that the cables clear the arms and legs during walking. The first embodiments can be modified to form further first embodiments in which the adapters are configured and positioned to permit free armswing of the subject. The first embodiments can be modified to form further first embodiments in which the computed gait trajectory includes a path of an ankle in space. The first embodiments can be modified to form further first embodiments in which the controller is configured to generate a graphic animation in real time showing the subject the error between the gait trajectory and the predefined trajectory. The first embodiments can be modified to form further first embodiments in which ones of the plurality of cables terminate at the shank adapter extensions. The first embodiments can be modified to form further first embodiments in which the controller is programmed simultaneously to apply tensions that tend to generate oppositely-directed torques in the first adapter. The first embodiments can be modified to form further first embodiments in which the first and second adapters portions that wrap around the thigh and shank, respectively. The first embodiments can be modified to form further first embodiments in which cable portions extending between the first and second adapters run straight therebetween with no intervening support. The first embodiments can be modified to form further first embodiments in which cable tension controller is programmed to generate an assist-as-needed type of control effect, generating forces to restore the target gait trajectory responsively to an error between the gait trajectory and the predefined trajectory. The first embodiments can be modified to form further first embodiments in which cable tension controller is programmed to generate an assist-as-needed type of control effect, generating forces to restore the target gait trajectory progressively with an error between the gait trajectory and the predefined trajectory. The first embodiments can be modified to form further first embodiments in which the cable tension controller may be placed selectively in a transparent mode in which it drives cable tensions to minimize forces on the voluntary movement of the subject and collects and stores data from the resulting driving of cable tensions to capture the movement of the subject.

According to second embodiments, the disclosed subject matter includes a leg manipulation system with a cable driven mechanism with a first adapter configured to be positioned on a body part of the subject, the first adapter having extensions for attachment of a plurality of cables therefrom, the extensions holding the cables in a position away from a joint of the body part so that the cables are not in contact with the joint of a remainder of the body part and such that selective moments are applied to the body part responsively to tension applied by a cable tension controller configured to control the tension in each of the plurality of cables. A plurality of sensors is configured to generate sensor data indicating angles of movement of different segments of the body part during a target movement thereof. wherein the cable tension controller is configured to compute a computed body part trajectory responsive to the sensor data. The cable tension controller is further configured to the computed body part trajectory with a predefined trajectory and to calculate command data for commanding selected respective tensions in the plurality of cables responsive to the comparison. The cable tension controller is programmed to control the plurality of cables to achieve the selected tension in each cable to generate torques in the body part to urge the body part toward the predefined trajectory. The tensions of the plurality of cables are converted to moments by the joints of the subject without support of external joints.

The second embodiments can be modified to form further second embodiments in which the body part includes at least one of the leg, pelvis, thigh, and/or shank of the subject. The second embodiments can be modified to form further second embodiments in which the cable tension controller further calculates a level of assistance to be applied to the body part. The second embodiments can be modified to form further second embodiments that include a second adapter configured to be positioned on the body part at a location remote, and separated by the joint, from a position of the first adapter. The second embodiments can be modified to form further second embodiments in which the second adapter has extensions for sliding engagement ones of the plurality of cables such that tension in the ones generates a moment about the joint to flex or extend the body part about the joint. The second embodiments can be modified to form further second embodiments in which the second adapter extensions hold the cables in a position away from the joint of the body part so that the cables are not in contact with the joint of a remainder of the body part. The second embodiments can be modified to form further second embodiments in which the cable drive mechanism includes motorized winches, each of which controls an angular position of a pulley to control the tension in a respective one of the plurality of cables. The second embodiments can be modified to form further second embodiments in which the motorized winches are attached to a fixed frame. The second embodiments can be modified to form further second embodiments in which the frame includes a hip adapter that restricts the motion of the pelvis of a subject, of whose body the body part is apart. The second embodiments can be modified to form further second embodiments in which the hip adapter wraps about the subject hip and waist and closes as a belt. The second embodiments can be modified to form further second embodiments in which the hip adapter is connected to other ones of the cables and the cable tension controller is programmed to apply predefined wrenches to the hip adapter. The second embodiments can be modified to form further second embodiments in which the predefined trajectory is based on a characteristic of a human gait. The second embodiments can be modified to form further second embodiments in which the adapters include cuffs that wrap around the body part. The second embodiments can be modified to form further second embodiments in which the adapter extensions position each of the plurality of cables such that the cables clear the body part. The second embodiments can be modified to form further second embodiments in which the adapters are configured and positioned to permit free armswing of the subject. The second embodiments can be modified to form further second embodiments in which the computed body part trajectory includes a path of an ankle in space. The second embodiments can be modified to form further second embodiments in which the controller is configured to generate a graphic animation in real time showing the subject the error between the body part trajectory and the predefined trajectory. The second embodiments can be modified to form further second embodiments that include a second adapter configured to be positioned on the body part at a location remote, and separated by the joint, from a position of the first adapter, at least one of the cables exerting torques on both the first and second adapters at least partly determined by a tension in the at least one of the cables. The second embodiments can be modified to form further second embodiments in which the second adapter has extensions for sliding engagement ones of the plurality of cables such that tension in the ones generates a moment about the joint to flex or extend the body part about the joint. The second embodiments can be modified to form further second embodiments in which the ones terminate at the first adapter extensions. The second embodiments can be modified to form further second embodiments in which the controller is programmed simultaneously to apply tensions that tend to generate oppositely-directed torques in the first adapter. The second embodiments can be modified to form further second embodiments in which the first and second adapters portions that wrap around the thigh and shank, respectively. The second embodiments can be modified to form further second embodiments in which cable portions extending between the first and second adapters run straight therebetween with no intervening support. The second embodiments can be modified to form further second embodiments in which the body part includes the leg of the subject. The second embodiments can be modified to form further second embodiments in which cable-driven mechanisms are provided for two legs of the subject. The second embodiments can be modified to form further second embodiments in which cable tension controller is programmed to generate an assist-as-needed type of control effect, generating forces to restore the target body part trajectory responsively to an error between the body part trajectory and the predefined trajectory. The second embodiments can be modified to form further second embodiments in which cable tension controller is programmed to generate an assist-as-needed type of control effect, generating forces to restore the target body part trajectory progressively with an error between the body part trajectory and the predefined trajectory. The second embodiments can be modified to form further second embodiments in which the cable tension controller may be placed selectively in a transparent mode in which it drives cable tensions to minimize forces on the voluntary movement of the subject and collects and stores data from the resulting driving of cable tensions to capture the movement of the subject.

According to third embodiments, the disclosed subject matter includes a method of gait training. The method includes pulling a forward shank cable to generate a first torque on a thigh and second torque on a shank, the first torque are generated through a first lever attached to the thigh, the forward shank cable are connected by a sliding joint to an end of the first lever. The method further includes pulling a forward thigh cable to generate a second torque on the thigh, the torque are generated by a second lever attached to the thigh, the forward thigh cable terminated at and affixed to the second lever. The method further includes using a controller and motorized drivers, controlling tensions in the forward shank cable and the forward thigh cable to generated guiding forces throughout a gait cycle of a walking subject.

The third embodiments can be modified to form additional third embodiments in which the pulling includes drawing a cable by means of a winch or linear drive attached to an external frame. The third embodiments can be modified to form additional third embodiments in which the first and second levers are of substantially the same length. The third embodiments can be modified to form additional third embodiments in which the first and second levers extend perpendicularly of the axis and from a middle of the thigh. The third embodiments can be modified to form additional third embodiments that include pulling a rear shank cable to generate a third torque on the thigh and fourth torque on the shank, the first torque are generated through a third lever attached to the thigh, the rear shank cable are connected by a sliding joint to an end of the third lever; pulling a rear thigh cable to generate a fourth torque on the thigh, the torque are generated by a fourth lever attached to the thigh, the rear thigh cable terminated at and affixed to the fourth lever; and using the controller and motorized drivers, controlling tensions in the rear shank cable and the rear thigh cable to generated guiding forces throughout a gait cycle of a walking subject.

The third embodiments can be modified to form additional third embodiments in which the forward and rear shank cables are terminated at and affixed to fifth and sixth levers attached to a shank of a leg. The third embodiments can be modified to form additional third embodiments that include pulling the forward and rear shank cables to generate fifth and sixth torques on the shank. The third embodiments can be modified to form additional third embodiments in which the generating torques includes generating moments by resisting cable tension imbalance using the knees and hips of a subject exclusively, without relying on external support of the hips or knee of the subject. The third embodiments can be modified to form additional third embodiments in which the guiding forces define a force tunnel such that the subject feels no forces when tracking a target gait path and the magnitude of guiding force varies smoothly with the magnitude of the error between an actual path and the target gait path. The third embodiments can be modified to form additional third embodiments in which the lever arms are all at least 35 percent longer than a local radius of the connected limb, whereby the cable is supported remotely from the subject's body. The third embodiments can be modified to form additional third embodiments in which wherein the cable, at points between the levers, is unsupported and runs along a straight path between the levers in space. The local radius of the limb may be taken as half the average diameter or the circumference divided by $2\pi$ at the axial midpoint of the adapter. For example, the point where the adapter is affixed to the thigh, the axial (lengthwise) midpoint of the adapter is the point along the thigh where the local radius is measured.

According to fourth embodiments, the disclosed subject matter includes a method for manipulating a leg. The method includes detecting angles of movement of different segments of a body part during movement thereof and generating sensor data based on the detecting. responsive to the sensor data, determining a trajectory of the body part. The method further includes comparing calculated trajectory with a selected trajectory for the body part. controlling tension in one or more cables attached to an adapter positioned on the body part so as to exert a torque on the body part responsively to the comparing.

The fourth embodiments can be modified to form additional fourth embodiments in which the controlling tension is such that a deviation between the calculated trajectory and the selected trajectory of the body part is reduced. The fourth embodiments can be modified to form additional fourth embodiments in which the body part is one of the leg, pelvis, thigh, and/or shank of the subject. The fourth embodiments can be modified to form additional fourth embodiments that include determining a level of assistance to be applied to the body part.

According to fifth embodiments, the disclosed subject matter includes a gait training system for a subject. An adapter is configured to be worn about the pelvis of the subject, a plurality of cables attached to the adapter. A treadmill is configured to support the subject while walking. A frame is arranged over the treadmill, the frame supporting multiple cable actuators, connected to the plurality of cables, to control tension in the plurality of cables responsively to control commands applied by a controller. A sensor detects gait patterns, the controller is programmed to generate data responsive to a phase of the gait of a subject wearing the adapter. the controller is programmed to temporarily perturb the adapter at predefined points in a gait cycle in predefined directions by controlling tension in the plurality of cables.

The fifth embodiments can be modified to for additional fifth embodiments in which a spring is provided in series with each of the plurality of cables. The fifth embodiments can be modified to for additional fifth embodiments in which a load cell is provided in series with each of the plurality of cables. The fifth embodiments can be modified to for additional fifth embodiments that include at least one imaging device supported on the frame and configured to image markers on the adapter and/or on the subject, the imaging device applying image signals in real time to a motion capture computer. The fifth embodiments can be modified to for additional fifth embodiments in which the motion capture computer is programmed to measure and quantify responses of the subject. The fifth embodiments can be modified to for additional fifth embodiments in which the motion capture computer is connected to the controller to apply motion capture data, the magnitude and type of the perturbations are responsive to the motion capture data. The fifth embodiments can be modified to for additional fifth embodiments in which the controller is programmed to apply greater perturbation forces and/or excursions when the motion capture indicates more competent recovery and lesser perturbation forces and/or excursions when the motion capture indicates less competent recovery. The fifth embodiments can be modified to for additional fifth embodiments in which the competence of the recovery is indicated by a length of time or number of steps it takes for the subject to return to a baseline gait pattern. The fifth embodiments can be modified to for additional fifth embodiments that include a display arranged with respect to the treadmill and connected to the motion capture computer, the motion capture computer are programmed to generate a feedback display indicating gait recovery. The fifth embodiments can be modified to for additional fifth embodiments in which the controller is programmed to perturb the adapter at random times such that the subject cannot predict when the perturbation will be applied. The fifth embodiments can be modified to for additional fifth embodiments in which the predefined direction has medial-lateral, antero-posterior, and superior-inferior components. The fifth embodiments can be modified to for additional fifth embodiments in which the predefined direction has medial-lateral, antero-posterior, or superior-inferior components. The fifth embodiments can be modified to for additional fifth embodiments in which the predefined direction has at least two of medial-lateral, antero-posterior, and superior-inferior components.

According to sixth embodiments, the disclosed subject matter includes a gait training system for a subject. An adapter is configured to be worn about the pelvis of the subject, a plurality of cables attached to the adapter. A treadmill is configured to support the subject while walking. A frame is arranged over the treadmill, the frame supporting multiple cable actuators, connected to the plurality of cables, to control tension in the plurality of cables responsively to control commands applied by a controller. A sensor detects gait patterns, the controller is programmed to generate data responsive to a phase of the gait of a subject wearing the adapter. the controller is programmed to apply a force with a majority vertical component to the adapter at predefined points in a gait cycle by controlling tension in the plurality of cables.

The sixth embodiments can be modified for form additional sixth embodiments in which a spring is provided in series with each of the plurality of cables. The sixth embodiments can be modified for form additional sixth embodiments in which a load cell is provided in series with each of the plurality of cables. The sixth embodiments can be modified for form additional sixth embodiments that include at least one imaging device supported on the frame and configured to image markers on the adapter and/or on the subject, the imaging device applying image signals in real time to a motion capture computer. The sixth embodiments can be modified for form additional sixth embodiments in which the motion capture computer is programmed to measure and quantify responses of the subject to the force. The sixth embodiments can be modified for form additional sixth embodiments in which the motion capture computer is connected to the controller to apply motion capture data, the magnitude and type of the force are responsive to the motion capture data. The sixth embodiments can be modified for form additional sixth embodiments that include a display arranged with respect to the treadmill and connected to the motion capture computer, the motion capture computer are programmed to generate a feedback display indicating gait recovery. The sixth embodiments can be modified for form additional sixth embodiments in which the force is asymmetric. The sixth embodiments can be modified for form additional sixth embodiments in which the force is along one leg of the subject. The sixth embodiments can be modified for form additional sixth embodiments in which the force is varied according to a phase of the gait cycle, the phase are derived by the controller from a signal originating from a shoe sensor, the motion capture, or tension signals detected by load sensors in the cables. The sixth embodiments can be modified for form additional sixth embodiments in which the display indicates symmetry of the gait of the subject. The sixth embodiments can be modified for form additional sixth embodiments in which the cables have inline springs. The sixth embodiments can be modified for form additional sixth embodiments that include shoe pressure sensors wearable by the user and configured for applying ground reaction forces to the controller. The sixth embodiments can be modified for form additional sixth embodiments in which the controller is programmed to derive a phase of the gait cycle from signals from the shoe pressure sensors. The sixth embodiments can be modified for form additional sixth embodiments in which the maximum of the force is between 5 and 20% of the subject's body weight. The sixth embodiments can be modified for form additional sixth embodiments in which the maximum of the force is between 5 and 15% of the subject's body weight. The sixth embodiments can be modified for form additional sixth embodiments in which the maximum of the force is about 10% of the subject's body weight. The sixth embodiments can be modified for form additional sixth embodiments in which the force includes an anterior-posterior component that varies throughout the gait cycle. The sixth embodiments can be modified for form additional sixth embodiments in which the force includes an medial-lateral component that varies throughout the gait cycle. The sixth embodiments can be modified for form additional sixth embodiments in which the force includes an anterior-posterior component that varies throughout the gait cycle and is lower in peak magnitude than the vertical component. The sixth embodiments can be modified for form additional sixth embodiments in which the force includes an medial-lateral component that varies throughout the gait cycle and is lower in peak magnitude than the vertical component. The sixth embodiments can be modified for form additional sixth embodiments in which the magnitude of vertical component of the force is always higher than anterior-posterior or medial lateral over a gait cycle.

According to seventh embodiments, the disclosed subject matter includes a method of treating a gait abnormality using the system of any of the first through sixth embodiments that includes selecting a subject responsively to a gait abnormality that includes weaker than a predefined force of pushing off as indicated by a force applied using a shoe sensor at a predefined point in the gait cycle.

According to eighth embodiments, the disclosed subject matter includes a cable actuated system to assist in balance and gait training of a subject. A mobile support includes a plurality of cables attached to a harness adapted for supporting a human subject in an upright position with the subject's legs in contact with a surface, the mobile support are configured to roll on the surface to permit a subject in the harness to traverse the surface. Tensions in the cables are controlled by cable actuators under control of a controller. One or more tension sensors are connected between the harness and the mobile support to detect interactive forces applied to the cables. The controller is programmed to detect a phase of gait of the subject. The harness is configured and the controller is programmed to apply a wrench through the harness to the pelvis of the subject responsively to the detected phase and responsively to the tensions. the wrench includes a torque resulting from a combination of tensions in the cables actuating the plurality of cables.

The eighth embodiments can be modified to form additional eighth embodiment that include a computer processing device to allow for the human-robot interaction. The eighth embodiments can be modified to form additional eighth embodiment in which the force and/or torque is applied to the pelvis of the subject. The eighth embodiments can be modified to form additional eighth embodiment in which the force and/or torque is a three-dimensional force and/or torque. The eighth embodiments can be modified to form additional eighth embodiment in which the computer processing device includes a low level controller to provide friction compensation, and a high level controller to provide movement classification data and to compute balance force and holding device velocity data. The eighth embodiments can be modified to form additional eighth embodiment in which the sensor data acquisition and response thereto is in real-time. The eighth embodiments can be modified to form additional eighth embodiment in which the wrench is applied in proportion to a degree to which a subject's hip trajectory exceeds a predefined trajectory. The eighth embodiments can be modified to form additional eighth embodiment in which the wrench is implemented as a force tunnel. The eighth embodiments can be modified to form additional eighth embodiment that include a feedback display indicating a hip trajectory shown as a point and a trace superimposed on the target hip trajectory. The eighth embodiments can be modified to form additional eighth embodiment in which the feedback display shows a planar projection of a three dimensional motion. The eighth embodiments can be modified to form additional eighth embodiment in which the feedback display shows a linear projection of a planar projection of a three dimensional motion. The eighth embodiments can be modified to form additional eighth embodiment in which the predefined trajectory is a three-dimensional curve. The eighth embodiments can be modified to form additional eighth embodiment in which the feedback display shows the force tunnel as a gradient indicating the magnitude of the restoring force as a function of displacement from the target trajectory.

According to ninth embodiments, the disclosed subject matter includes a method for assisting in balance and gait training. The method includes exerting a force or a torque on a body part of a subject positioned in a cable actuated system includes a plurality of cables attached to a harness-like mechanism to hold the subject in an upright position, and a mobile base to allow the system to move in different directions, the force and/or torque exerted on the body part are based on sensor data received from one or more sensors attached to one or more of the plurality of cables to detect interactive forces between the subject and the cable actuated system. The sensor data may include data relating to the posture and balance of the subject. The sensor data and response thereto may be in real-time.

The ninth embodiments can be modified to form additional ninth embodiment in which the wrench is applied in proportion to a degree to which a subject's hip trajectory exceeds a predefined trajectory. The ninth embodiments can be modified to form additional ninth embodiment in which the wrench is implemented as a force tunnel. The ninth embodiments can be modified to form additional ninth embodiment that include a feedback display indicating a hip trajectory shown as a point and a trace superimposed on the target hip trajectory. The ninth embodiments can be modified to form additional ninth embodiment in which the feedback display shows a planar projection of a three dimensional motion. The ninth embodiments can be modified to form additional ninth embodiment in which the feedback display shows a linear projection of a planar projection of a three dimensional motion. The ninth embodiments can be modified to form additional ninth embodiment in which the predefined trajectory is a three-dimensional curve.

It will be appreciated that the disclosed modules, processes, or systems associated with control or use of the disclosed devices may be implemented in hardware, hardware programmed by software, software instruction stored on a non-transitory computer readable medium or a combination of the above. For example, any of the methods or processes disclosed herein can be implemented, for example, using a processor configured to execute a sequence of programmed instructions stored on a non-transitory computer readable medium, which processor and/or computer readable medium may be part of a system configured to control or use of the active tethered pelvic assist device. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, any of the methods or processes disclosed herein can be implemented as a single processor or as a distributed processor, which single or distributed processor may be part of a system configured to control or use the active tethered pelvic assist device. Further, it should be appreciated that the steps mentioned herein may be performed on a single or distributed processor (single and/or multi-core). Also, any of the methods or processes described in the various Figures of and for embodiments herein may be distributed across multiple computers or systems or may be co-located in a single processor or system. Exemplary structural embodiment alternatives suitable for implementing any of the methods or processes described herein are provided below.

Any of the methods or processes described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example, any of which may be part of a system configured to control or use the active tethered pelvic assist device.

Embodiments of the methods, processes, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or computer program products (i.e., software program stored on a non-transitory computer readable medium).

Furthermore, embodiments of the disclosed methods, processes, or systems may be readily implemented, fully or partially, in software using, for example, object or object-oriented software development environments that provide portable source code that can be used on a variety of computer platforms. Alternatively, embodiments of the disclosed methods, processes, or systems can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the disclosed methods, processes, or systems can be implemented in hardware and/or software using any known or later developed systems or structures, devices and/or software by those of ordinary skill in the art from the function description provided herein and with knowledge of computer programming arts.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific materials have been disclosed herein, other materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for human movement research, therapy, and diagnosis. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. A cable driven exoskeleton system, comprising:
one or more motorized drives connected to control tension in a plurality of cables;
a shank adapter configured to be positioned on the shank of a leg of a subject, the shank adapter having extensions for attachment of respective ones of the plurality of cables therefrom, the shank adapter extensions holding the cables in a position away from a knee so that the cables are not in contact with the knee or other parts of the leg and such that selective moments are applied to the shank responsively to tension in the respective ones of the plurality of cables;
tensions applied to the plurality of cables being determined by a cable tension controller configured to control the one or more motorized drives;
a thigh adapter with extensions configured to be positioned on the thigh of the subject, the shank adapter having extensions for attachment of respective ones of the plurality of cables therefrom, the thigh adapter extensions holding the cables in a position away from a knee so that the cables are not in contact with the knee or other parts of the leg and such that selective moments are applied to the thigh responsively to tension applied by the cable tension controller; and
tension sensors configured to generate sensor data indicating angles of movement of the thighs and shanks of the subject during walking;
wherein the cable tension controller is configured to compute a computed gait trajectory responsive to the sensor data,
the cable tension controller being further configured to compare the computed gait trajectory with a predefined trajectory and to calculate command data for commanding selected respective tensions in the plurality of cables responsive to a result of the comparing, and
the cable tension controller being programmed to control the plurality of cables to achieve the selected tension in each cable to generate torques in the shank and thigh toward the predefined trajectory;
the tension of the plurality of cables being converted to moments by a joint of the subject without support of an external joint.

2. The system of claim 1, wherein the one or more motorized drives includes motorized winches, each of which controls an angular position of a pulley to control the tension in a respective one of the plurality of cables.

3. The system of claim 2, wherein the motorized winches are attached to a hip adapter that is supported on the hips of the subject, wherein the hip adapter is configured to wrap about the subject hip and waist and close as a belt, wherein the hip adapter is connected to other ones of said cables and said cable tension controller is programmed to apply predefined wrenches to said hip adapter.

4. The system of claim 1, wherein the thigh adapter extensions are configured to permit sliding engagement of ones of the plurality of cables such that tension in the ones generates a moment about said subject joint to flex or extend the knee.

5. A leg manipulation system, comprising:
one or more motorized drives with a first adapter configured to be positioned on a body part of a subject, the first adapter having extensions for attachment of a plurality of cables therefrom, the extensions holding the cables in a position away from a joint of the body part so that the cables are not in contact with the joint of a remainder of the body part and such that selective moments are applied to the body part responsively to tension applied by a cable tension controller configured to control the tension in each of the plurality of cables; and
a plurality of sensors configured to generate sensor data indicating angles of movement of different segments of the body part during a target movement thereof;
wherein the cable tension controller is configured to compute a computed body part trajectory responsive to the sensor data,
the cable tension controller being further configured to compare the computed body part trajectory with a predefined trajectory and to calculate command data for commanding selected respective tensions in the plurality of cables responsive to a result of the comparing;
the cable tension controller being programmed to control the plurality of cables to achieve the selected tension in each cable to generate torques in the body part to urge the body part toward the predefined trajectory;
the tension of the plurality of cables being converted to moments by the joint of the subject without support of an external joint.

6. The system of claim 5, wherein the one or more motorized drives includes motorized winches, each of which controls an angular position of a pulley to control the tension in a respective one of the plurality of cables, wherein the motorized winches are attached to a fixed frame, wherein the frame includes a hip adapter that restricts the motion of a pelvis of the subject.

7. The system of claim 6, wherein the hip adapter is configured to wrap about the pelvis and a waist of the subject and close as a belt, wherein the hip adapter is connected to other ones of said cables and said cable tension controller is programmed to apply predefined wrenches to said hip adapter, wherein the motorized winches are attached to a fixed frame, wherein the hip adapter restricts a motion of pelvis of the subject, wherein the hip adapter is configured to wrap about the subject pelvis and waist and close as a belt.

8. The system of claim 5, wherein the body part includes at least one of the leg, pelvis, thigh, and/or shank of the subject.

9. A method of gait training, comprising:
pulling a forward shank cable to generate a first torque on a thigh and second torque on a shank, the first torque being generated through a sliding guide attached to the thigh;
pulling a forward thigh cable to generate a second torque on the thigh, the torque being generated through a first fixed extension attached to the thigh;
using a controller and motorized drives, controlling tensions in the forward shank cable and the forward thigh cable to generate guiding forces throughout a gait cycle of a walking subject;
pulling a rear shank cable to generate a third torque on the thigh and fourth torque on the shank, the third torque being generated through a sliding guide attached to the thigh;
pulling a rear thigh cable to generate a fifth torque on the thigh, the fifth torque being generated through a second fixed extension attached to the thigh; and
using the controller and motorized drives, controlling tensions in the rear shank cable and the rear thigh cable to generated guiding forces throughout the gait cycle of the walking subject.

10. The method of claim 9, wherein the forward and rear shank cables are terminated at and affixed to fifth and sixth extensions attached to the shank of a leg.

11. The method of claim 10, further comprising pulling the forward and rear shank cables to generate fifth and sixth torques on the shank.

12. The method of claim 11, wherein the generating torques includes generating moments by resisting cable tension imbalance using the knees and hips of the subject exclusively, without relying on external support of the hips or knee of the subject.

13. The method of claim 12, wherein the guiding forces define a force tunnel such that the subject feels no forces when tracking a target gait path and the magnitude of guiding force varies smoothly with the magnitude of an error between an actual path and the target gait path.

14. The method of claim 9, further comprising pulling the forward and rear shank cables to generate fifth and sixth torques on the shank.

15. The method of claim 14, wherein the generating torques includes generating moments by resisting cable tension imbalance using the knees and hips of the subject exclusively, without relying on external support of the hips or knee of the subject.

16. The method of claim 15, wherein the guiding forces define a force tunnel such that the subject feels no forces when tracking a target gait path and the magnitude of guiding force varies smoothly with the magnitude of an error between an actual path and the target gait path.

17. A leg manipulation system, comprising:
one or more motorized drives with a first adapter configured to be positioned on a body part of a subject, the first adapter having extensions for attachment of a plurality of cables therefrom, the extensions holding the cables in a position away from a joint of the body part so that the cables are not in contact with the joint of a remainder of the body part and such that selective moments are applied to the body part responsively to tension applied by a cable tension controller configured to control the tension in each of the plurality of cables; and
a plurality of sensors configured to generate sensor data indicating angles of movement of different segments of the body part during a target movement thereof;
wherein the cable tension controller is configured to compute a computed body part trajectory responsive to the sensor data,
the cable tension controller being further configured to compare the computed body part trajectory with a predefined trajectory and to calculate command data for commanding selected respective tensions in the plurality of cables responsive to a result of the comparing;
the cable tension controller being programmed to control the plurality of cables to achieve the selected tension in each cable to generate torques in the body part to urge the body part toward the predefined trajectory;

the tension of the plurality of cables being converted to moments by the joint of the subject without support of an external joint;

wherein each of the one or more motorized drives controls tension in a respective one of the plurality of cables, wherein at least one of the one or more motorized drives is attached by a respective at least one of the plurality of cables to a hip adapter that is configured to wrap around a hip and waist of the subject and restrict the motion of a pelvis of the subject.

18. The system of claim 17, wherein the body part includes at least one of the leg, pelvis, thigh, and/or shank of the subject.

19. The system of claim 18, wherein the hip adapter is connected to certain ones of said plurality of cables and said cable tension controller is programmed to apply predefined wrenches to said hip adapter.

20. The system of claim 19, wherein the hip adapter is configured to wrap about the subject pelvis and waist and close as a belt.

21. The system of claim 17, wherein the hip adapter is connected to certain ones of said plurality of cables and said cable tension controller is programmed to apply predefined wrenches to said hip adapter.

22. The system of claim 21, wherein the hip adapter is configured to wrap about the subject pelvis and waist and close as a belt.

* * * * *